(12) United States Patent
Tsukamoto et al.

(10) Patent No.: US 7,629,494 B2
(45) Date of Patent: Dec. 8, 2009

(54) PROCESS FOR PRODUCING CYCLOPROPYLPHENOL DERIVATIVE

(75) Inventors: Yoshihisa Tsukamoto, Shiga (JP); Hiroyuki Komai, Shiga (JP); Toshio Kaneko, Tokyo (JP); Takeshi Takada, Shiga (JP)

(73) Assignee: Mitsui Chemicals Agro, Inc., Tokyo (JP)

( * ) Notice: Subject to any disclaimer, the term of this patent is extended or adjusted under 35 U.S.C. 154(b) by 248 days.

(21) Appl. No.: 11/887,159

(22) PCT Filed: Mar. 31, 2006

(86) PCT No.: PCT/JP2006/306806

§ 371 (c)(1), (2), (4) Date: Sep. 25, 2007

(87) PCT Pub. No.: WO2006/106906

PCT Pub. Date: Oct. 12, 2006

(65) Prior Publication Data

US 2009/0054681 A1     Feb. 26, 2009

(30) Foreign Application Priority Data

Mar. 31, 2005   (JP)   ............... 2005-102820

(51) Int. Cl.
  *C07C 69/76*   (2006.01)
  *C07C 39/17*   (2006.01)
(52) U.S. Cl. ...................... 568/731; 560/103
(58) Field of Classification Search ................. 568/731; 560/103
  See application file for complete search history.

(56) References Cited

U.S. PATENT DOCUMENTS

2005/0037925 A1   2/2005  Tsukamoto et al.

FOREIGN PATENT DOCUMENTS

| JP | 2-256684 A | 10/1990 |
|---|---|---|
| JP | 2004-002263 A | 1/2004 |
| WO | WO 03/016286 A1 | 2/2003 |

OTHER PUBLICATIONS

Thomas F. Corbin et al., "Cyclopropylbenzene," *Organic Syntheses*, 1964, vol. 44, pp. 30 to 33.
Roger C. Hahn et al., "Electrical Effects of Cycloalkyl Groups[1]," *Journal of the American Chemical Society*, 1968, vol. 90, No. 13, pp. 3404 to 3415.
T.W. Greene et al., "Protection for Phenols and Catechols," *Protective Groups in Organic Synthesis*, Third Edition, 1999, pp. 276 to 287.
J.J. Talley et al., "Reaction of Lithium o-Lithiophenoxide with Carbonyl Compounds," *The Journal of Organic Chemistry*, 1984, vol. 49, No. 26, pp. 5267 to 5269.

Torsten Herbertz et al., "Oxidation of Aryl- and Diarylcyclopropanes in a Pentasil Zeolite: Ring Opening with Deprotonation or Net Hydrogen Migration," *Eur. J. Org. Chem.*, 2000, pp. 467 to 472.

(Continued)

*Primary Examiner*—Sikarl A Witherspoon
(74) *Attorney, Agent, or Firm*—Frishauf, Holtz, Goodman & Chick, P.C.

(57) ABSTRACT

A process for producing a cyclopropylphenol represented by of formula (10):

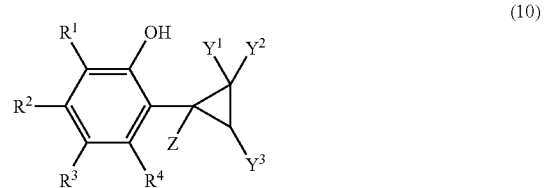

(10)

wherein $R^1$, $R^2$, $R^3$ and $R^4$ each may represent a hydrogen; Z represents a hydrogen, alkyl, alkenyl, alkynyl, cycloalkyl or phenyl; and $Y^1$, $Y^2$ and $Y^3$ each may represent a hydrogen; by reacting a compound of formula (7):

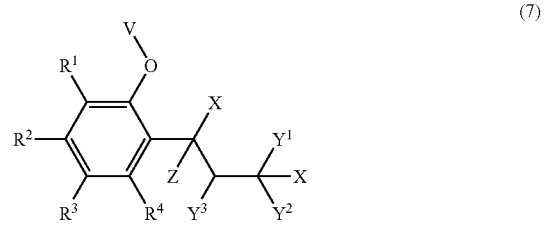

(7)

wherein X represents a halogen; and V represents a hydrogen or —W—$R^5$, with a metal, metal salt or organometallic compound of formula (8): $M^2$ to obtain a compound of formula (9):

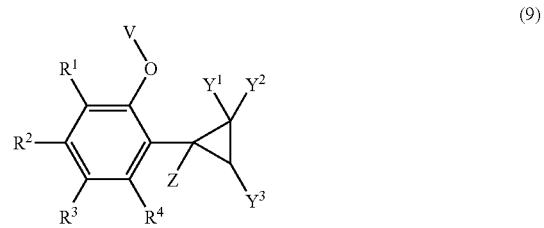

(9)

and obtaining a compound of formula (10) by hydrolysis in the case wherein V represents —W—$R^5$, wherein W is CO, SO or $SO_2$ and $R^5$ is alkyl, haloalkyl, cycloalkyl, alkenyl, alkynyl, phenyl, alkoxy or haloalkoxy.

39 Claims, No Drawings

OTHER PUBLICATIONS

S. Walia et al., "Cyclopropyl MDP Compounds as New Pyrethrum Synergists," *Agric. Biol. Chem.*, 1984, 48(11), pp. 2675 to 2679.

Tohru Kitamura et al., "Photochemical Reactions of Allylphenoxide Anions," *Tetrahedron*, 1978, vol. 34, pp. 3451 to 3457.

John A. Soderquist et al., "Aryl and Vinyl Cyclopropanes Through the In Situ Generation of B-cyclopropyl-9-BBN and its Suzuki-Miyaura Coupling," *Tetrahedron Letters*, 41, (2000), pp. 4251 to 4255.

José Barluenga et al., "Diastereo- and Enantioselective Carbolithiation of Allyl o-Lithioaryl Ethers. New Chiral cyclopropane Derivatives," *Organic Letters*, (2002), vol. 4, No. 13, pp. 2225 to 2228.

Debra J. Wallace et al., "Cyclopropylboronic Acid: Synthesis and Suzuki Cross-Coupling Reactions," *Tetrahedron Letters*, 43, (2002), pp. 6987 to 6990.

Fachuang Lu et al., "The DFRC Method for Lignin Analysis. 7. Behavior of Cinnamyl End Groups," *J. Argic. Food Chem.*, (1999), vol. 47, No. 5, pp. 1981 to 1987.

Joseph Paul Jayachandran et al., "Synthesis, Characterization, and Utility of Trialkyl(3-sulfopropyl)ammonium Betaines as New Phase Transfer Reagents," *Synthetic Communications*, (2003), vol. 33, No. 14, pp. 2463 to 2468.

Gerhard Quinkert et al., "120.Stereoselective Ring Opening of Electronically Excited cyclohexa-2,4-dienones: Cause and Effect," *Helvetica Chimica Acta*, vol. 80, (1997) pp. 1683 to 1772.

English-language International Preliminary Report on Patentability and Written Opinion of the International Searching Authority, dated Feb. 26, 2008 for International application PCT/JP2006/306806 filed Mar. 31, 2006; Applicants: Sankyo Agro Company, Limited.

PROCESS FOR PRODUCING CYCLOPROPYLPHENOL DERIVATIVE

This application is the United States national phase application of International Application PCT/JP2006/306806 filed Mar. 31, 2006.

TECHNICAL FIELD

The present invention relates to a process for producing cyclopropylphenol derivatives useful as intermediates of pharmaceuticals, agrochemicals and functional materials.

BACKGROUND ART

Cyclopropylphenol derivatives of the present invention are useful as intermediates of pharmaceuticals/agrochemicals and functional materials. For example, a 3-phenoxy-4-pyridazinol derivative having herbicidal activity is produced using a cyclopropylphenol derivative as an intermediate (Patent Document 1). Examples of known process for producing cyclopropylphenol derivatives include a process for synthesizing from styrenes by a Simmons-Smith reaction (Non-Patent Document 1), a process in which a 5-phenylpyrazoline is heated to reduce ring size (Non-Patent Document 2), a process in which an allyl phenol ether is subjected to an intramolecular ring closure by photoreaction (Non-Patent Document 3), a process for condensing a vinyl phenol ether and diazomethane using a palladium catalyst (Non-Patent Document 4), a process for coupling a hydroxy(cyclopropyl)boron complex, obtained by dihydroboronation of propagyl bromide followed by treatment with an alkaline aqueous solution, with a phenyl bromide using a palladium catalyst (Non-Patent Document 5), a process for synthesizing via an intramolecular ring closure by reacting 1-allyloxy-2-bromobenzene and t-butyl lithium (Non-Patent Document 6), a process for condensing cyclopropyl borate with a phenyl bromide in the presence of a palladium catalyst (Non-Patent Document 7), a process for synthesizing from (1,3-dibromopropyl)benzene by an intramolecular ring closure reaction using zinc (Non-Patent Document 8) and a process for reacting chloroform with a styrene in the presence of a phase transfer catalyst and sodium hydroxide (Non-Patent Document 9).

However, Simmons-Smith reagent, palladium catalyst and boron complexes are expensive reagents, and since intramolecular ring closure reactions by photoreaction or using t-butyl lithium, reactions for reducing ring size of pyrazoline using heat, cyclization reactions of dibromophenols using zinc or the like result in the formation of large amounts of by-products, the yield of the desired compound is generally low. Moreover, since Simmons-Smith reagent, diazomethane, boron complexes, t-butyl lithium and palladium catalysts and the like are unstable reagents, they have shortcomings such as problems with ease of the reaction procedure. In addition, in Non-Patent Document 8, a 4-(1,3-dibromopropyl)phenyl acetate derivative is synthesized by reacting a cinnamyl alcohol derivative and acetyl bromide, and then followed by an intramolecular ring closure reaction with zinc to synthesize a desired cyclopropylphenol derivative. However, cinnamyl alcohol is not acquired easily. In addition, in Non-Patent Document 9, dichloromethylcarbene is generated from chloroform by a styrene derivative to synthesize a dichlorocyclopropylphenol derivative. However, chloroform is highly toxic and it is difficult to acquire styrene derivatives.

[Patent Document 1] WO 03/016286 A1

[Non Patent Document 1] Herbertz, T.; Lakkaraju, Prasad S.; Blume, F.; Blume, M.; Rosht, H. D. Eur. J. Org. Chem., 2000, 3, 467-472.

[Non Patent Document 2] Walia, S.; Saxena, V. S.; Mukerjee, S. K. Agric. Biol. Chem., 1984, 48, 2675-2680.

[Non Patent Document 3] Kitamura, T.; Imagawa, T.; Kawanishi, M, Tetrahedron, 1978, 34, 3451-3457.

[Non Patent Document 4] Quinkert, G.; Scherer, S.; Reichert, D.; Nestler, H.-P.; Wennemers, H. et al. Helv. Chim. Acta, 1997, 80, 1683-1772.

[Non Patent Document 5] Soderquist, J. A.; Huertas, R.; Leon-Colon, G. Tetrahedron Lett., 2000, 41, 4251-4246.

[Non Patent Document 6] Barluenga, J.; Fananas, F. J.; Sanz, R.; Marcos, C. Org. Lett., 2002, 4, 2225-2228.

[Non Patent Document 7] Wallace, D. J.; Chen, C. Tetrahedron Lett., 2002, 43, 6987-6990.

[Non Patent Document 8] Lu, F.; Ralph, J. J. Agric. Food Chem., 1999, 47, 1981-1987.

[Non Patent Document 9] Jayachandran, J. P.; Wang, M.-L. Synth. Commun., 2003, 33, 2463-2468.

DISCLOSURE OF THE INVENTION

Problems to be Solved by the Invention

The inventors of the present invention conducted extensive studies to develop a simple synthesis process in consideration of the importance of cyclopropylphenol derivatives as synthesis intermediates of pharmaceuticals/agrochemicals and functional materials. As a result, the inventors of the present invention found that a cyclopropylphenol derivative (10) can be synthesized by using an easily acquirable phenylcarbonyl compound (1) as a raw material, reacting it with an organometallic compound (2) to obtain an alcohol derivative (3), and either reacting this with an acid halide (6) or reacting with a hydrogen halide (5) in the presence of an acid anhydride (4) to synthesize a (1,3-dihaloalkyl)phenyl ester derivative (7) as an intermediate followed by reacting with a metal or organic metal, thereby leading to completion of the present invention.

Means for Solving the Problems

The present invention relates to a process for producing a cyclopropylphenol derivative represented by general formula (10):

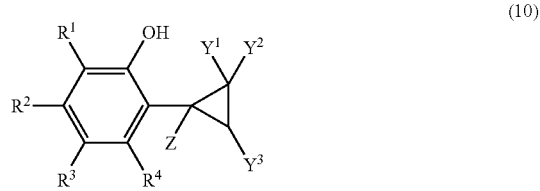

(10)

[wherein $R^1$, $R^2$, $R^3$ and $R^4$ each independently represent a hydrogen atom, halogen atom, optionally substituted $C_1$-$C_6$ alkyl group (wherein said substituent is a substituent selected from the following substituent group B), optionally substituted $C_2$-$C_6$ alkenyl group (wherein said substituent is a cyano group or nitro group), $C_2$-$C_6$ alkynyl group, optionally substituted $C_3$-$C_6$ cycloalkyl group (wherein said substituent is a substituent selected from the following substituent group C), $C_4$-$C_{10}$ bicycloalkyl group, cyano group, formyl group, $C_2$-$C_7$ alkylcarbonyl group, optionally substituted benzoyl group (wherein said substituent is a substituent selected from the following substituent group A), carboxyl group, $C_2$-$C_7$ alkoxycarbonyl group, carbamoyl group, di($C_1$-$C_6$ alkyl)carbamoyl group, optionally substituted phenyl group (wherein said substituent is a substituent selected from the following substituent group A), optionally substituted 3 to 6 membered heterocyclic group (wherein said heterocyclic ring contains one nitrogen atom, oxygen atom or sulfur atom therein, may further contain 1 to 2 nitrogen atoms, may be condensed with a benzene ring, and said substituent is a substituent selected from the following substituent group E), optionally substituted amino group (wherein said substituent is a substituent selected from the following substituent group D), nitro group, hydroxyl group, $C_1$-$C_6$ alkoxy group, $C_1$-$C_6$ haloalkoxy group, ($C_1$-$C_6$ alkoxy) $C_1$-$C_6$ alkoxy group, optionally substituted phenoxy group (wherein said substituent is a hydroxyl group or a pyridazinyloxy group substituted with a halogen atom and/or $C_1$-$C_6$ alkoxy group), optionally substituted 5 to 6 membered heterocyclooxy group (wherein said heterocyclic ring contains one nitrogen atom, oxygen atom or sulfur atom therein, may further contain 1 to 2 nitrogen atoms, and said substituent is a substituent selected from the following substituent group E), optionally substituted $C_2$-$C_7$ alkylcarbonyloxy group (wherein said substituent is a substituent selected from the following substituent group B), optionally substituted $C_2$-$C_7$ alkoxycarbonyloxy group (wherein said substituent is a substituent selected from the following substituent group B), optionally substituted benzoyloxy group (wherein said substituent is a substituent selected from the following substituent group A), optionally substituted phenylsulfonyloxy group (wherein said substituent is a substituent selected from the following substituent group A), $C_1$-$C_6$ alkylthio group, $C_1$-$C_6$ alkylsulfinyl group, $C_1$-$C_6$ alkylsulfonyl group or tri($C_1$-$C_6$ alkyl)silyl group, or two adjacent $R^1$, $R^2$, $R^3$ and $R^4$ may together with carbon atoms respectively bonded thereto form an optionally substituted 3 to 6 membered cyclic hydrocarbon group (wherein said cyclic hydrocarbon may be interrupted by 1 to 2 same or different heteroatoms selected from the group consisting of a nitrogen atom, oxygen atom and sulfur atom, said substituent is a halogen atom, $C_1$-$C_6$ alkyl group, hydroxy $C_1$-$C_6$ alkyl group, $C_1$-$C_6$ alkoxy group, oxo group, hydroxyimino group or $C_1$-$C_6$ alkoxyimino group, and in the case the cyclic hydrocarbon is substituted with a $C_1$-$C_6$ alkyl group, a new 3-membered ring may be formed by bonding with other $C_1$-$C_6$ alkyl groups or carbon atoms on the ring);

Z represents a hydrogen atom, optionally substituted $C_1$-$C_6$ alkyl group (wherein said substituent is a substituent selected from the following substituent group B), $C_2$-$C_6$ alkenyl group, $C_2$-$C_6$ alkynyl group, optionally substituted $C_3$-$C_6$ cycloalkyl group or optionally substituted phenyl group (wherein said substituent is a substituent selected from the following substituent group A);

$Y^1$, $Y^2$ and $Y^3$ each independently represent a hydrogen atom, halogen atom, optionally substituted $C_1$-$C_6$ alkyl group (wherein said substituent is a substituent selected from the following substituent group B), optionally substituted $C_2$-$C_6$ alkenyl group (wherein said substituent is a cyano group or nitro group), $C_2$-$C_6$ alkynyl group, optionally substituted $C_3$-$C_6$ cycloalkyl group (wherein said substituent is a substituent selected from the following substituent group C), optionally substituted phenyl group (wherein said substituent is a substituent selected from the following substituent group A), nitro group, $C_1$-$C_6$ alkoxy group, $C_1$-$C_6$ haloalkoxy group, ($C_1$-$C_6$ alkoxy)$C_1$-$C_6$ alkoxy group, $C_1$-$C_6$ alkylthio group, $C_1$-$C_6$ alkylsulfinyl group or $C_1$-$C_6$ alkylsulfonyl group;

substituent group A is a group consisting of a halogen atom, $C_1$-$C_6$ alkyl group, $C_1$-$C_6$ haloalkyl group, $C_3$-$C_6$ cycloalkyl group, cyano group and tri($C_1$-$C_6$ alkyl)silyl group;

substituent group B is a group consisting of a halogen atom, $C_3$-$C_6$ cycloalkyl group, cyano group, $C_2$-$C_7$ alkylcarbonyl group, $C_2$-$C_7$ alkoxycarbonyl group, phenyl group, $C_1$-$C_6$ alkoxy group, $C_1$-$C_6$ alkylthio group, $C_1$-$C_6$ alkylsulfinyl group, $C_1$-$C_6$ alkylsulfonyl group, $C_1$-$C_4$ alkylenedioxy group, hydroxyimino group and $C_1$-$C_6$ alkoxyimino group;

substituent group C is a group consisting of a halogen atom, optionally substituted $C_1$-$C_6$ alkyl group (wherein said substituent is a substituent selected from the aforementioned substituent group B), $C_3$-$C_6$ cycloalkyl group, $C_2$-$C_6$ alkenyl group, cyano group, $C_2$-$C_7$ alkylcarbonyl group, benzoyl group, carboxyl group, $C_2$-$C_7$ alkoxycarbonyl group, carbamoyl group, di($C_1$-$C_6$ alkyl)carbamoyl group, optionally substituted phenyl group (wherein said substituent is a substituent selected from the aforementioned substituent group A), 5- or 6-membered heterocyclic group (wherein said heterocyclic ring contains one nitrogen atom, oxygen atom or sulfur atom therein, and may further contain 1 to 2 nitrogen atoms), optionally substituted amino group (wherein said substituent is a substituent selected from the following substituent group D), nitro group, hydroxyl group, $C_1$-$C_6$ alkoxy group, $C_1$-$C_6$ haloalkoxy group, phenoxy group, $C_1$-$C_6$ alkylthio group, phenylthio group, $C_1$-$C_6$ alkylsulfinyl group and $C_1$-$C_6$ alkylsulfonyl group;

substituent group D is a group consisting of a $C_1$-$C_6$ alkyl group, $C_2$-$C_7$ alkylcarbonyl group, $C_2$-$C_7$ alkoxycarbonyl group, di($C_1$-$C_6$ alkyl)carbamoyl group and $C_1$-$C_6$ alkylsulfonyl group; and substituent group E is a group consisting of a halogen atom, $C_1$-$C_6$ alkyl group, $C_1$-$C_6$ haloalkyl group, hydroxyl group, optionally substituted phenylsulfonyl group (wherein said substituent is a substituent selected from the aforementioned substituent group A) and di($C_1$-$C_6$ alkyl)sulfamoyl group];

the process comprising reacting a compound represented by general formula (7):

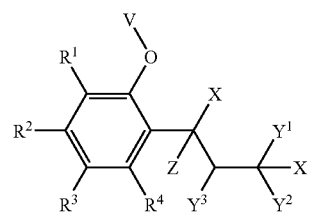

(7)

[wherein $R^1$, $R^2$, $R^3$, $R^4$, Z, $Y^1$, $Y^2$ and $Y^3$ are the same as previously defined; X represents a halogen atom; V represents a hydrogen atom or the group, —W—$R^5$, wherein $R^5$ represents a $C_1$-$C_6$ alkyl group, $C_1$-$C_6$ haloalkyl group, $C_3$-$C_6$ cycloalkyl group, $C_2$-$C_6$ alkenyl group, $C_2$-$C_6$ alkynyl group, optionally substituted phenyl group (wherein said substituent is a substituent selected from a halogen atom and $C_1$-$C_6$ alkyl group), $C_1$-$C_6$ alkoxy group or $C_1$-$C_6$ haloalkoxy group; and, W represents a CO, SO or SO$_2$ group] with a metal, metal salt or organometallic compound represented by general formula (8):

$$M^2 \quad (8)$$

to obtain a compound represented by general formula (9):

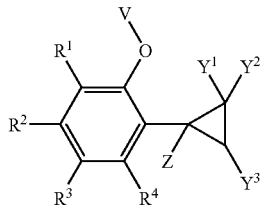
(9)

[wherein $R^1$, $R^2$, $R^3$, $R^4$, V, Z, $Y^1$, $Y^2$ and $Y^3$ are the same as previously defined] and obtaining a compound represented by general formula (10) by hydrolysis in the case V represents the group, —W—$R^5$.

In addition, the present invention also relates to a process for obtaining a compound of the aforementioned general formula (10) further comprising a step in which a compound of general formula (7) is obtained by reacting a compound represented by general formula (3):

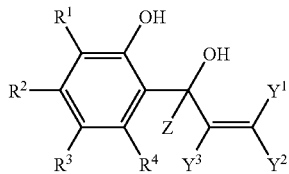
(3)

[wherein $R^1$, $R^2$, $R^3$, $R^4$, Z, $Y^1$, $Y^2$ and $Y^3$ are the same as previously defined] with a mixture of a compound represented by general formula (4):

(4)

[wherein $R^5$ and W are the same as previously defined] and a compound represented by general formula (5):

$$H—X \quad (5)$$

[wherein X is the same as previously defined], or by reacting with an acid halide represented by general formula (6):

(6)

[wherein $R^5$, W and X are the same as previously defined].

The present invention also relates to the aforementioned process further comprising a step in which a compound represented by general formula (3) is obtained by reacting a compound represented by general formula (1):

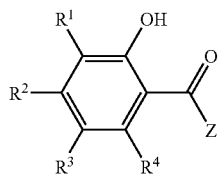
(1)

[wherein $R^1$, $R^2$, $R^3$, $R^4$ and Z are the same as previously defined], or salt thereof, with an organometallic compound represented by general formula (2):

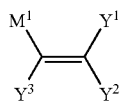
(2)

[wherein $Y^1$, $Y^2$ and $Y^3$ are the same as previously defined; and $M^1$ represents a metal residue, metal salt residue or organometallic residue].

The present invention also relates to the aforementioned process further comprising a step in which a compound represented by general formula (7) is obtained by reacting a compound represented by general formula (11):

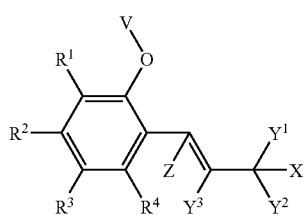
(11)

[wherein $R^1$, $R^2$, $R^3$, $R^4$, V, X, Z, $Y^1$, $Y^2$ and $Y^3$ are the same as previously defined] with a hydrogen halide represented by general formula (5):

$$H—X \quad (5)$$

[wherein X is the same as previously defined].

Moreover, the present invention also relates to a compound represented by the aforementioned general formula (3) (wherein $R^1$, $R^2$, $R^3$ and $R^4$ are the same as previously defined, and Z, $Y^1$, $Y^2$ and $Y^3$ represent hydrogen atoms provided that $R^1$ is not a hydrogen atom).

Moreover, the present invention also relates to a compound represented by general formula (7'):

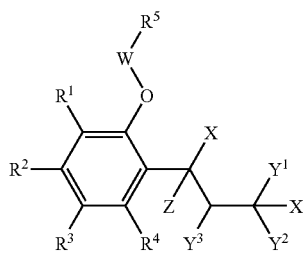
(7')

[wherein $R^1$, $R^2$, $R^3$, $R^4$, $R^5$, W, X, Z, $Y^1$, $Y^2$ and $Y^3$ are the same as previously defined, provided that $R^5$ is neither a $C_1$-$C_6$ alkoxy group nor $C_1$-$C_6$ haloalkoxy group, and X is not a fluorine atom], or salt thereof; and a compound represented by general formula (7"):

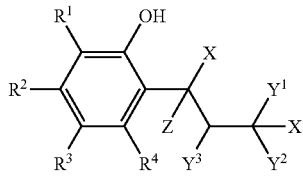
(7")

[wherein $R^1$, $R^2$, $R^3$, $R^4$, X, Z, $Y^1$, $Y^2$ and $Y^3$ are the same as previously defined, provided that X is not a fluorine atom), or salt thereof, which compose a compound represented by the aforementioned general formula (7).

In addition, the present invention also relates to a compound represented by general formula (9'):

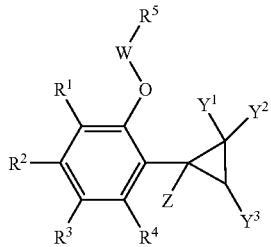
(9')

[wherein $R^1$, $R^2$, $R^3$, $R^4$, $R^5$, W, Z, $Y^1$, $Y^2$ and $Y^3$ are the same as previously defined, provided that $R^1$ is neither a hydrogen atom nor acetoxy group], or salt thereof, which composes a compound represented by the aforementioned general formula (9).

In addition, the present invention also relates to a compound represented by general formula (11'):

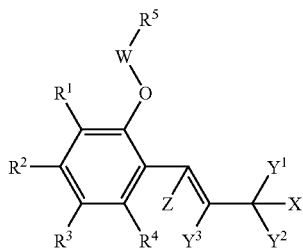
(11')

[wherein $R^1$, $R^2$, $R^3$, $R^4$, $R^5$, W, X, Z, $Y^1$, $Y^2$ and $Y^3$ are the same as previously defined, provided that $R^1$ is neither a hydrogen atom nor acetoxy group, and X is not a fluorine atom], or salt thereof, and a compound represented by general formula (11"):

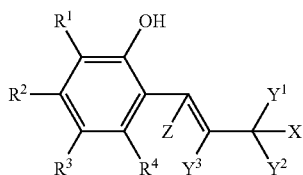
(11")

[wherein $R^1$, $R^2$, $R^3$, $R^4$, X, Z, and $Y^3$ are the same as previously defined, and $Y^1$ and $Y^2$ represent hydrogen atoms, provided that X is not a fluorine atom], or salt thereof, which compose a compound represented by the aforementioned general formula (11).

EFFECTS OF THE INVENTION

According to the process of the present invention, since cyclopropylphenol derivatives can be produced inexpensively at high yield and with stability, cyclopropylphenol derivatives useful as raw materials of pharmaceuticals/agrochemicals and functional materials can be easily produced.

BEST MODE FOR CARRYING OUT THE INVENTION

In the present invention, a "halogen atom" is a fluorine atom, chlorine atom, bromine atom or iodine atom, preferably a fluorine atom, chlorine atom or bromine atom, more preferably a chlorine atom or bromine atom, and even more preferably a chlorine atom.

In the present invention, the "$C_1$-$C_6$ alkyl group" is a linear or branched alkyl group having 1 to 6 carbon atoms, examples of which include a methyl, ethyl, propyl, isopropyl, butyl, isobutyl, s-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group, preferably a linear or branched alkyl group having 1 to 4 carbon atoms ($C_1$-$C_4$ alkyl group), more preferably a linear or branched alkyl group having 1 to 3 carbon atoms ($C_1$-$C_3$ alkyl group), even more preferably an alkyl group having 1 to 2 carbon atoms ($C_1$-$C_2$ alkyl group), and particularly preferably a methyl group.

In the present invention, the "$C_3$-$C_6$ cycloalkyl group" is a cyclopropyl, cyclobutyl, cyclopentyl or cyclohexyl group, preferably a cyclopropyl or cyclobutyl group, more preferably a cyclopropyl group.

In the present invention, the "$C_2$-$C_7$ alkylcarbonyl group" is a carbonyl group to which the aforementioned "$C_1$-$C_6$ alkyl group" is bonded, examples of which include an acetyl, propionyl, butyryl, isobutyryl, valeryl, isovaleryl, pivaloyl, hexanoyl or heptanoyl group, preferably a carbonyl group to which a linear or branched alkyl group having 1 to 4 carbon atoms are bonded ($C_2$-$C_5$ alkylcarbonyl group), even more preferably a carbonyl group to which a linear or branched alkyl group having 1 to 3 carbon atoms are bonded ($C_2$-$C_4$ alkylcarbonyl group), particularly preferably an acetyl, propionyl, valeryl or pivaloyl group, and most preferably an acetyl group.

In the present invention, the "$C_1$-$C_6$ alkoxy group" is a linear or branched alkoxy group having 1 to 6 carbon atoms, examples of which include a methoxy, ethoxy, propoxy, isopropoxy, butoxy, isobutoxy, s-butoxy, t-butoxy, pentoxy, isopentoxy, 2-methylbutoxy, neopentoxy, 1-ethylpropoxy, hexyloxy, 4-methylpentoxy, 3-methylpentoxy, 2-methylpentoxy, 1-methylpentoxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy or 2-ethylbutoxy group, preferably a linear or branched alkoxy group having 1 to 3 carbon atoms ($C_1$-$C_3$ alkoxy group), more preferably a methoxy or ethoxy group, even more preferably a methoxy group.

In the present invention, the "$C_2$-$C_7$ alkoxycarbonyl group" is a carbonyl group to which the aforementioned "$C_1$-$C_6$ alkoxy group" is bonded, examples of which include a methoxycarbonyl, ethoxycarbonyl, propoxycarbonyl, isopropoxycarbonyl, butoxycarbonyl, isobutoxycarbonyl, s-butoxycarbonyl, t-butoxycarbonyl, pentoxycarbonyl, isopentoxycarbonyl, 2-methylbutoxycarbonyl, neopentoxycarbonyl, 1-ethylpropoxycarbonyl, hexyloxycarbonyl, 4-methylpentoxycarbonyl, 3-methylpentoxycarbonyl, 2-methylpentoxycarbonyl, 1-methylpentoxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, 2,3-dimethylbutoxycarbonyl or 2-ethylbutoxycarbonyl group, preferably a carbonyl group to which a $C_1$-$C_3$ alkoxy group is bonded ($C_2$-$C_4$ alkoxycarbonyl group), more preferably a methoxycarbonyl or ethoxycarbonyl group, even more preferably a methoxycarbonyl group.

In the present invention, the "$C_1$-$C_6$ alkylthio group" is a linear or branched alkylthio group having 1 to 6 carbon atoms, examples of which include a methylthio, ethylthio, propylthio, isopropylthio, butylthio, isobutylthio, s-butylthio, t-butylthio, pentylthio, isopentylthio, 2-methylbutylthio, neopentylthio, 1-ethylpropylthio, hexylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio or 2-ethylbutylthio group, preferably a linear or branched alkylthio group having 1 to 3 carbon atoms ($C_1$-$C_3$ alkylthio group), more preferably a methylthio or ethylthio group, even more preferably a methylthio group.

In the present invention, the "$C_1$-$C_6$ alkylsulfinyl group" is a linear or branched alkylsulfinyl group having 1 to 6 carbon atoms, examples of which include a methylsulfinyl, ethylsulfinyl, propylsulfinyl, isopropylsulfinyl, butylsulfinyl, isobutylsulfinyl, s-butylsulfinyl, t-butylsulfinyl, pentylsulfinyl, isopentylsulfinyl, 2-methylbutylsulfinyl, neopentylsulfinyl, 1-ethylpropylsulfinyl, hexylsulfinyl, 4-methylpentylsulfinyl, 3-methylpentylsulfinyl, 2-methylpentylsulfinyl, 1-methylpentylsulfinyl, 3,3-dimethylbutylsulfinyl, 2,2-dimethylbutylsulfinyl, 1,1-dimethylbutylsulfinyl, 1,2-dimethylbutylsulfinyl, 1,3-dimethylbutylsulfinyl, 2,3-dimethylbutylsulfinyl or 2-ethylbutylsulfinyl group, preferably a linear or branched alkylsulfinyl group having 1 to 3 carbon atoms ($C_1$-$C_3$ alkylsulfinyl group), more preferably a methylsulfinyl or ethylsulfinyl group, even more preferably a methylsulfinyl group.

In the present invention, the "$C_1$-$C_6$ alkylsulfonyl group" is a linear or branched alkylsulfonyl group having 1 to 6 carbon atoms, examples of which include a methylsulfonyl, ethylsulfonyl, propylsulfonyl, isopropylsulfonyl, butylsulfonyl, isobutylsulfonyl, s-butylsulfonyl, t-butylsulfonyl, pentylsulfonyl, isopentylsulfonyl, 2-methylbutylsulfonyl, neopentylsulfonyl, 1-ethylpropylsulfonyl, hexylsulfonyl, 4-methylpentylsulfonyl, 3-methylpentylsulfonyl, 2-methylpentylsulfonyl, 1-methylpentylsulfonyl, 3,3-dimethylbutylsulfonyl, 2,2-dimethylbutylsulfonyl, 1,1-dimethylbutylsulfonyl, 1,2-dimethylbutylsulfonyl, 1,3-dimethylbutylsulfonyl, 2,3-dimethylbutylsulfonyl or 2-ethylbutylsulfonyl group, preferably a linear or branched alkylsulfonyl group having 1 to 3 carbon atoms ($C_1$-$C_3$ alkylsulfonyl group), more preferably a methylsulfonyl or ethylsulfonyl group, even more preferably a methylsulfonyl group.

In the present invention, the "$C_1$-$C_4$ alkylenedioxy group" is a linear or branched alkylenedioxy group having 1 to 4 carbon atoms, examples of which include a methylenedioxy, ethylenedioxy, propylenedioxy, trimethylenedioxy or tetramethylenedioxy group, preferably an alkylenedioxy group having 1 to 2 carbon atoms, more preferably a 1,2-ethylenedioxy group.

In the present invention, the "$C_1$-$C_6$ alkoxyimino group" is a linear or branched alkoxyimino group having 1 to 6 carbon atoms, examples of which include a methoxyimino, ethoxyimino, propoxyimino, isopropoxyimino, butoxyimino, isobutoxyimino, s-butoxyimino, t-butoxyimino, pentoxyimino, isopentoxyimino, 2-methylbutoxyimino, neopentoxyimino, 1-ethylpropoxyimino, hexyloxyimino, 4-methylpentoxyimino, 3-methylpentoxyimino, 2-methylpentoxyimino, 1-methylpentoxyimino, 3,3-dimethylbutoxyimino, 2,2-dimethylbutoxyimino, 1,1-dimethylbutoxyimino, 1,2-dimethylbutoxyimino, 1,3-dimethylbutoxyimino, 2,3-dimethylbutoxyimino or 2-ethylbutoxyimino group, preferably a linear or branched alkoxyimino group having 1 to 3 carbon atoms ($C_1$-$C_3$ alkoxyimino group), more preferably a methoxyimino or ethoxyimino group, even more preferably a methoxyimino group.

In the present invention, the "optionally substituted $C_1$-$C_6$ alkyl group (wherein said substituent is a substituent selected from the substituent group B)" is the aforementioned "$C_1$-$C_6$ alkyl group" optionally substituted with the aforementioned "halogen atom", or with same or different 1 to 5 substituents selected from the group consisting of the aforementioned "$C_3$-$C_6$ cycloalkyl group", cyano group, the aforementioned "$C_2$-$C_7$ alkylcarbonyl group", the aforementioned "$C_2$-$C_7$ alkoxycarbonyl group", phenyl group, the aforementioned "$C_1$-$C_6$ alkoxy group", the aforementioned "$C_1$-$C_6$ alkylthio group", the aforementioned "$C_1$-$C_6$ alkylsulfinyl group", the aforementioned "$C_1$-$C_6$ alkylsulfonyl group", the aforementioned "$C_1$-$C_4$ alkylenedioxy group", hydroxyimino group or the aforementioned "$C_1$-$C_6$ alkoxyimino group", examples of which include a methyl, ethyl, propyl, isopropyl, butyl, t-butyl, fluoromethyl, difluoromethyl, trifluoromethyl, 2,2,2-trichloroethyl, cyclopropylmethyl, cyanomethyl, acetylmethyl, acetylethyl, methoxycarbonylmethyl, methoxycarbonylethyl, ethoxycarbonylmethyl, ethoxycarbonylethyl, benzyl, methoxymethyl, methoxyethyl, ethoxymethyl, ethoxyethyl, methylthiomethyl, methylthioethyl, ethylthiomethyl, ethylthioethyl, methylsulfinylmethyl, methylsulfonylmethyl, 2-(1,3-dioxolanyl), hydroxyiminomethyl or methoxyiminomethyl group, preferably a $C_1$-$C_3$ alkyl group optionally substituted with 1 to 3 same or different substituents selected from the group consisting of a fluorine atom, chlorine atom and bromine atom, or $C_1$-$C_3$ alkyl group optionally substituted with 1 to 3 same or different substituents selected from the group consisting of $C_3$-$C_4$ cycloalkyl group, cyano group, $C_2$-$C_4$ alkylcarbonyl group, $C_2$-$C_4$ alkoxycarbonyl group, phenyl group, $C_1$-$C_3$ alkoxy group, $C_1$-$C_3$ alkylthio group, $C_1$-$C_3$ alkylsulfinyl group, $C_1$-$C_3$ alkylsulfonyl group, $C_1$-$C_2$ alkylenedioxy group, hydroxyimino group or $C_1$-$C_3$ alkoxyimino group, more preferably a $C_1$-$C_2$ alkyl group optionally substituted with 1 to 3 same fluorine atoms or chlorine atoms, or a $C_1$-$C_2$ alkyl group optionally substituted with 1 to 2 same or different substituent groups selected from the group consisting of cyclopropyl group, cyano group, $C_2$-$C_3$ alkylcarbonyl group, $C_2$-$C_3$ alkoxycarbonyl group, phenyl group, $C_1$-$C_2$ alkoxy group, $C_1$-$C_2$ alkylthio group, $C_1$-$C_2$ alkylsulfinyl group, $C_1$-$C_2$ alkylsulfonyl group, ethylenedioxy group, hydroxyimino group or $C_1$-$C_2$ alkoxyimino group.

In the present invention, the "$C_2$-$C_6$ alkenyl group" is a linear or branched alkenyl group having 2 to 6 carbon atoms, examples of which include a vinyl, 1-methylvinyl, allyl, 1-propenyl, 1-methyl-1-propenyl, 1-methyl-2-propenyl, 2-methyl-2-propenyl, 2-ethyl-2-propenyl, 2-butenyl, 1-methyl-2-butenyl, 2-methyl-2-butenyl, 1-ethyl-2-butenyl, 3-butenyl, 1-methyl-3-butenyl, 2-methyl-3-butenyl, 1-ethyl-3-butenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 2-hexenyl, 3-hexenyl, 4-hexenyl or 5-hexenyl group, preferably a linear or branched alkenyl group having 2 to 4 carbon atoms ($C_2$-$C_4$ alkenyl group), more preferably a vinyl, 1-methylvinyl, allyl, 1-propenyl or 1-methyl-2-propenyl group.

In the present invention, the "substituted $C_2$-$C_6$ alkenyl group (wherein said substituent is a cyano group or nitro group)" is the aforementioned "$C_2$-$C_6$ alkenyl group" substituted with a cyano group and/or nitro group, preferably a $C_2$-$C_3$ alkenyl group substituted with a cyano group or nitro group, more preferably a cyanovinyl or nitrovinyl group.

In the present invention, the "$C_2$-$C_6$ alkynyl group" is a linear or branched alkynyl group having 2 to 6 carbon atoms, examples of which include an ethynyl, 2-propynyl, 1-methyl-2-propynyl, 1-ethyl-2-propynyl, 2-butynyl, 1-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 1-ethyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl or 5-hexynyl, preferably a linear or branched alkynyl group having 2 to 4 carbon atoms ($C_2$-$C_4$ alkynyl group), more preferably an ethynyl, 1-propynyl or 2-propynyl group.

In the present invention, the "di($C_1$-$C_6$ alkyl)carbamoyl group" is a carbamoyl group in which same or different two aforementioned "$C_1$-$C_6$ alkyl groups" are bonded to nitrogen atoms, examples of which include a dimethylcarbamoyl, methylethylcarbamoyl, diethylcarbamoyl, dipropylcarbamoyl, dibutylcarbamoyl or dihexylcarbamoyl group, preferably a carbamoyl group to which same two linear or branched alkyl group having 1 to 3 carbon atoms are bonded {di($C_1$-$C_3$ alkyl)carbamoyl group}, more preferably a dimethylcarbamoyl group or diethylcarbamoyl group, and even more preferably a dimethylcarbamoyl group.

In the present invention, the "$C_1$-$C_6$ haloalkyl group" is the aforementioned "$C_1$-$C_6$ alkyl group" in which same or different 1 to 5 aforementioned "halogen atoms" are substituted, examples of which include a chloromethyl, dichloromethyl, trichloromethyl, 1-chloroethyl, 2-chloroethyl, 2,2,2-trichloroethyl, 1-chloropropyl, 3-chloropropyl, 1-chlorobutyl, 4-chlorobutyl, fluoromethyl, difluoromethyl, trifluoromethyl, 1-fluoroethyl, 2-fluoroethyl, 2,2,2-trifluoroethyl, pentafluoroethyl, fluorochloromethyl, bromomethyl, 1-bromoethyl, 2-bromoethyl or iodomethyl group, preferably a $C_1$-$C_3$ alkyl group substituted with same or different 1 to 3 substituents selected from the group consisting of a fluorine atom, chlorine atom and bromine atom, more preferably a $C_1$-$C_2$ alkyl group substituted with same 1 to 3 fluorine atoms or chlorine atoms, even more preferably a fluoromethyl, difluoromethyl, trifluoromethyl or 2,2,2-trichloroethyl group, and particularly preferably a trifluoromethyl group.

In the present invention, the "tri($C_1$-$C_6$ alkyl)silyl group" is a silicon atom to which same or different 3 aforementioned "$C_1$-$C_6$ alkyl groups" are bonded, examples of which include a trimethylsilyl, triethylsilyl, triisopropylsilyl, dimethylisopropylsilyl, t-butyldimethylsilyl or trihexylsilyl group, preferably a silicon atom to which same or different 3 linear or branched alkyl groups having 1 to 3 carbon atoms are bonded {tri($C_1$-$C_3$ alkyl)silyl group}, more preferably a trimethylsilyl or dimethylisopropylsilyl group, and even preferably a trimethylsilyl group.

In the present invention, the "optionally substituted phenyl group (wherein said substituent is a substituent selected from the substituent group A)" is a phenyl group optionally substituted with same or different 1 to 5 substituents selected from the group consisting of the aforementioned "halogen atom", the aforementioned "$C_1$-$C_6$ alkyl group", the aforementioned "$C_1$-$C_6$ haloalkyl group", the aforementioned "$C_3$-$C_6$ cycloalkyl group", cyano group and the aforementioned "tri($C_1$-$C_6$ alkyl)silyl group", examples of which include a phenyl, fluorophenyl, difluorophenyl, trifluorophenyl, chlorophenyl, dichlorophenyl, trichlorophenyl, fluorochlorophenyl, methylphenyl, dimethylphenyl, trimethylphenyl, tetramethylphenyl, pentamethylphenyl, ethylphenyl, fluoro(methyl)phenyl, chloro(methyl)phenyl, bromo(methyl)phenyl, cyclopropylphenyl, cyclopropyl(fluoro)phenyl, chloro(cyclopropyl)phenyl, cyclopropyl(methyl)phenyl, (trifluoromethyl)phenyl or fluoro(trifluoromethyl)phenyl group, preferably a phenyl group optionally substituted with same or different 1 to 3 substituents selected from the group consisting of a fluorine atom, chlorine atom, bromine atom, $C_1$-$C_3$ alkyl group, "$C_1$-$C_3$ alkyl group substituted with same or different 1 to 3 substituents selected from the group consisting of a fluorine atom, chlorine atom and bromine atom", $C_3$-$C_4$ cycloalkyl group, cyano group and tri($C_1$-$C_3$ alkyl)silyl group, more preferably a phenyl, chlorophenyl, methylphenyl, trifluorophenyl or cyanophenyl group.

In the present invention, the "5- or 6-membered heterocyclic group (wherein said heterocyclic ring contains one nitrogen atom, oxygen atom or sulfur atom therein, and may further contain 1 to 2 nitrogen atoms)" is a 5 to 6 membered heterocyclic ring which contains one nitrogen atom, oxygen atom or sulfur atom as a heteroatom, and may further contain 1 to 2 nitrogen atoms, examples of which include a furyl, thienyl, pyrrolyl, pyrazolyl, imidazolyl, isoxazolyl, oxazolyl, isothiazolyl, thiazolyl, triazolyl, pyranyl, pyridyl, pyrazinyl, pyrimidinyl, pyridazinyl or triazinyl group, preferably a 5-membered heterocyclic group (wherein said heterocyclic ring contains one nitrogen atom, oxygen atom or sulfur atom therein), and more preferably a furyl or thienyl group.

In the present invention, "optionally substituted amino group (wherein said substituent is a substituent selected from the substituent group D)" is an amino group optionally substituted with same or different 1 to 2 substituents selected from the group consisting of the aforementioned "$C_1$-$C_6$ alkyl group", the aforementioned "$C_2$-$C_7$ alkylcarbonyl group", the aforementioned "$C_2$-$C_7$ alkoxycarbonyl group", the aforementioned "di($C_1$-$C_6$ alkyl)carbamoyl group" and the aforementioned "$C_1$-$C_6$ alkylsulfonyl group", examples of which include an amino, methylamino, ethylamino, propylamino, isopropylamino, butylamino, isobutylamino, s-butylamino, t-butylamino, pentylamino, isopentylamino, (2-methylbutyl)amino, neopentylamino, (1-ethylpropyl)amino, hexylamino, (4-methylpentyl)amino, (3-methylpentyl)amino, (2-methylpentyl)amino, (1-methylpentyl)amino, (3,3-dimethylbutyl)amino, (2,2-dimethylbutyl)amino, (1,1-dimethylbutyl)amino, (1,2-dimethylbutyl)amino, (1,3-dimethylbutyl)amino, (2,3-dimethylbutyl)amino, (2-ethylbutyl)amino, dimethylamino, (methyl)(ethyl)amino, diethylamino, dipropylamino, (methyl)(isopropyl)amino, diisopropylamino, dibutylamino, diisobutylamino, di-s-butylamino, di-t-butylamino, dipentylamino, diisopentylamino, di(2-methylbutyl)amino, dineopentylamino, di(1-ethylpropyl)amino, dihexylamino, di(4-methylpentyl)amino, di(3-methylpentyl)amino, di(2-methylpentyl)amino, di(1-methylpentyl)amino, di(3,3-dimethylbutyl)amino, di(2,2-dimethylbutyl)amino, di(1,1-dimethylbutyl)amino, di(1,2-dimethylbutyl)amino, di(1,3-dimethylbutyl)amino, di(2,3-dimethylbutyl)amino, di(2-ethylbutyl)amino, acetylamino, propionylamino, butanoylamino, (2-methylpropanyl)amino, pentanoylamino, (2,2-dimethylpropanoyl)amino, (2,2-dimethyl pentanoyl)amino, (2-methylbutanoyl)amino, (3-methylbutanoyl)amino, hexanoylamino, heptanoylamino, (3,3-dimethylbutanoyl)amino, methoxycarbonylamino, ethoxycarbonylamino, propoxycarbonylamino, isopropoxycarbonylamino, butoxycarbonylamino, isobutoxycarbonylamino, s-butoxycarbonylamino, t-butoxycarbonylamino, pentoxycarbonylamino, isopentoxycarbonylamino, (2-methylbutoxycarbonyl)amino, neopentoxycarbonylamino, (1-ethylpropoxycarbonyl)amino, hexyloxycarbonylamino, (4-methylpentoxycarbonyl)amino, (3-methylpentoxycarbonyl)amino, (2-methylpentoxycarbonyl)amino, (1-methylpentoxycarbonyl)amino, (3,3-dimethylbutoxycarbonyl)amino, (2,2-dimethylbutoxycarbonyl)amino, (1,1-dimethylbutoxycarbonyl)amino, (1,2-dimethylbutoxycarbonyl)amino, (1,3-dimethylbutoxycarbonyl)amino, (2,3-dimethylbutoxycarbonyl)amino, (2-ethylbutoxycarbonyl)amino, dimethylcarbamoylamino, (methylethylcarbamoyl)amino, diethylcarbamoylamino, dipropylcarbamoylamino, dibutylcarbamoylamino, dihexylcarbamoylamino, methylsulfonylamino, ethylsulfonylamino, propylsulfonylamino, isopropylsulfonylamino, butylsulfonylamino, t-butylsulfonylamino or hexylsulfonylamino, preferably an amino group optionally substituted with same or different 1 to 2 $C_1$-$C_3$ alkyl groups, or with $C_2$-$C_4$ alkylcarbonyl group, $C_2$-$C_4$ alkoxycarbonyl group, di($C_1$-$C_3$ alkyl)carbamoyl group or $C_1$-$C_3$ alkylsulfonyl group, and more preferably a methylamino, ethylamino, dimethylamino, diethylamino, acetylamino, propionylamino, (2-methylpropanoyl)amino, (2,2-dimethyl propanoyl)amino, methoxycarbonylamino, ethoxycarbonylamino, dimethylcarbamoylamino, diethylcarbamoylamino, methylsulfonylamino or ethylsulfonylamino group.

In the present invention, the "$C_1$-$C_6$ haloalkoxy group" is the aforementioned "$C_1$-$C_6$ alkoxy group" substituted with same or different 1 to 5 aforementioned "halogen atoms", examples of which include a chloromethoxy, dichloromethoxy, trichloromethoxy, 1-chloroethoxy, 2-chloroethoxy, 2,2,2-trichloroethoxy, 1-chloropropoxy, 3-chloropropoxy, 1-chlorobutoxy, 4-chlorobutoxy, fluoromethoxy, difluoromethoxy, trifluoromethoxy, 1-fluoroethoxy, 2-fluoroethoxy, 2,2,2-trifluoroethoxy, pentafluoroethoxy, fluorochloromethoxy, bromomethoxy, 1-bromoethoxy, 2-bromoethoxy or iodomethoxy group, preferably a $C_1$-$C_3$ alkoxy group substituted with same or different 1 to 3 substituents selected from the group consisting of a fluorine atom, chlorine atom and bromine atom, more preferably a $C_1$-$C_2$ alkoxy group substituted with same 1 to 3 fluorine atoms or chlorine atoms, even more preferably a fluoromethoxy, difluoromethoxy, trifluoromethoxy or 2,2,2-trichloroethoxy group, and particularly preferably a trifluoromethoxy group.

In the present invention, the "substituted $C_3$-$C_6$ cycloalkyl group (wherein said substituent is a substituent selected from the substituent group C)" is the aforementioned "$C_3$-$C_6$ cycloalkyl group" substituted with same or different 1 to 5 substituents selected from the group consisting of the aforementioned "halogen atom", the aforementioned "optionally substituted $C_1$-$C_6$ alkyl group (wherein said substituent is a substituent selected from the substituent group B)", the aforementioned "$C_3$-$C_6$ cycloalkyl group", the aforementioned "$C_2$-$C_6$ alkenyl group", cyano group, the aforementioned "$C_2$-$C_7$ alkylcarbonyl group", benzoyl group, carboxyl group, the aforementioned "$C_2$-$C_7$ alkoxycarbonyl group", carbamoyl group, the aforementioned "di($C_1$-$C_6$ alkyl)carbamoyl group", the aforementioned "optionally substituted phenyl group (wherein said substituent is a substituent selected from the substituent group A)", the aforementioned "5- or 6-membered heterocyclic group (wherein said heterocyclic ring contains one nitrogen atom, oxygen atom or sulfur atom therein, and may further contain 1 to 2 nitrogen atoms)", the aforementioned "optionally substituted amino group (wherein said substituent is a substituent selected from the substituent group D)", nitro group, hydroxyl group, the aforementioned "$C_1$-$C_6$ alkoxy group", the aforementioned "$C_1$-$C_6$ haloalkoxy group", phenoxy group, the aforementioned "$C_1$-$C_6$ alkylthio group", phenylthio group, the aforementioned "$C_1$-$C_6$ alkylsulfinyl group" and the aforementioned "$C_1$-$C_6$ alkylsulfonyl group", examples of which include a fluorocyclopropyl, difluorocyclopropyl, chlorocyclopropyl, dichlorocyclopropyl, bromocyclopropyl, dibromocyclopropyl, iodocyclopropyl, methylcyclopropyl, ethylcyclopropyl, propylcyclopropyl, isopropylcyclopropyl, butylcyclopropyl, t-butylcyclopropyl, hexylcyclopropyl, cyclopropylcyclopropyl, cyclobutylcyclopropyl, cyclopentylcyclopropyl, (fluoromethyl)cyclopropyl, (chloromethyl)cyclopropyl, (bromomethyl)cyclopropyl, (difluoromethyl)cyclopropyl, (trifluoromethyl)cyclopropyl, (trichloromethyl)cyclopropyl, (2,2,2-trifluoroethyl)cyclopropyl, (2,2,2-trichloroethyl)cyclopropyl, vinylcyclopropyl, (methoxymethyl)cyclopropyl, (ethoxymethyl)cyclopropyl, (isopropoxymethyl)cyclopropyl, (methylthiomethyl)cyclopropyl, (ethylthiomethyl)cyclopropyl, (isopropylthiomethyl)cyclopropyl, (methylsulfinylmethyl)cyclopropyl, (ethylsulfinylmethyl)cyclopropyl, (methylsulfonylmethyl)cyclopropyl, (ethylsulfonylmethyl)cyclopropyl, cyanocyclopropyl, (1-methoxyiminoethyl)cyclopropyl, acetylcyclopropyl, propionylcyclopropyl, benzoylcyclopropyl, carboxylcyclopropyl, methoxycarbonylcyclopropyl, ethoxycarbonylcyclopropyl, carbamoylcyclopropyl, (dimethylcarbamoyl)cyclopropyl, (diethylcarbamoyl)cyclopropyl, phenylcyclopropyl, (fluorophenyl)cyclopropyl, (chlorophenyl)cyclopropyl, tolylcyclopropyl, furylcyclopropyl, thienylcyclopropyl, pyridylcyclopropyl, aminocyclopropyl, (methylamino)cyclopropyl, (dimethylamino)cyclopropyl, (acetylamino)cyclopropyl, (methoxycarbonylamino)cyclopropyl, (3,3-dimethylureido)cyclopropyl, (methylsulfonylamino)cyclopropyl, nitrocyclopropyl, hydroxycyclopropyl, methoxycyclopropyl, ethoxycyclopropyl, (trifluoromethoxy)cyclopropyl, phenoxycyclopropyl, methylthiocyclopropyl, ethylthiocyclopropyl, phenylthiocyclopropyl, methylsulfinylcyclopropyl, ethylsulfinylcyclopropyl, methylsulfonylcyclopropyl, ethylsulfonylcyclopropyl, dimethylcyclopropyl, methyl(ethyl)cyclopropyl, diethylcyclopropyl, biscyanocyclopropyl, trimethylcyclopropyl, tetramethylcyclopropyl, pentamethylcyclopropyl, methylcyclobutyl, vinylcyclobutyl, cyanocyclobutyl, carboxylcyclobutyl, acetylcyclobutyl, methoxycarbonylcyclobutyl or aminocyclobutyl group, preferably a $C_3$-$C_4$ cycloalkyl group substituted with same or different 1 to 5 substituents selected from the group consisting of a fluorine atom, chlorine atom, bromine atom, $C_1$-$C_3$ alkyl group, $C_3$-$C_4$ cycloalkyl group and cyano group, or with "$C_1$-$C_3$ alkyl group substituted with same or different 1 to 3 substituents selected from the group consisting of a fluorine atom, chlorine atom and bromine atom, or $C_1$-$C_3$ alkyl group substituted with $C_3$-$C_4$ cycloalkyl group, cyano group, $C_2$-$C_4$ alkylcarbonyl group, $C_2$-$C_4$ alkoxycarbonyl group, phenyl group, $C_1$-$C_3$ alkoxy group, $C_1$-$C_3$ alkylthio group, $C_1$-$C_3$ alkylsulfinyl group, $C_1$-$C_3$ alkylsulfonyl group, $C_1$-$C_2$ alkylenedioxy group, hydroxyimino group or $C_1$-$C_3$ alkoxyimino group", $C_2$-$C_4$ alkenyl group, $C_2$-$C_4$ alkylcarbonyl group, benzoyl group, carboxyl group, $C_2$-$C_4$ alkoxycarbonyl group, carbamoyl group, di($C_1$-$C_3$ alkyl)carbamoyl group, "phenyl group optionally substituted with same or different 1 to 3 substituents selected from the group consisting of a fluorine atom, chlorine atom, bromine atom, $C_1$-$C_3$ alkyl group, "$C_1$-$C_3$ alkyl group substituted with same or different 1 to 3 substituents selected from the group consisting of a fluorine atom, chlorine atom and bromine atom", $C_3$-$C_4$ cycloalkyl group, cyano group and tri($C_1$-$C_3$ alkyl)silyl group", 5-membered heterocyclic group (wherein said heterocyclic ring contains one nitrogen atom, oxygen atom or sulfur atom therein), "amino group optionally substituted with same or different 1 to 2 $C_1$-$C_3$ alkyl groups, or with $C_2$-$C_4$ alkylcarbonyl group, $C_2$-$C_4$ alkoxycarbonyl group, di($C_1$-$C_3$ alkyl)carbamoyl group or $C_1$-$C_3$ alkylsulfonyl group", nitro group, hydroxyl group, $C_1$-$C_3$ alkoxy group, $C_1$-$C_3$ haloalkoxy group, phenoxy group, $C_1$-$C_3$ alkylthio group, phenylthio group, $C_1$-$C_3$ alkylsulfinyl group or $C_1$-$C_3$ alkylsulfonyl group, more preferably a cyclopropyl group substituted with same or different 1 to 3 substituents selected from the group consisting of a chlorine atom, bromine atom, $C_1$-$C_2$ alkyl group, cyclopropyl group and cyano group, or with "$C_1$-$C_2$ alkyl group substituted with same 1 to 3 substituents selected from the group consisting of a chlorine atom and bromine atom, or $C_1$-$C_2$ alkyl group substituted with cyclopropyl group, cyano group, $C_2$-$C_3$ alkylcarbonyl group, $C_2$-$C_3$ alkoxycarbonyl group, phenyl group, $C_1$-$C_2$ alkoxy group, $C_1$-$C_2$ alkylthio group, $C_1$-$C_2$ alkylsulfinyl group, $C_1$-$C_2$ alkylsulfonyl group, 1,2-ethylenedioxy group, hydroxyimino group or $C_1$-$C_2$ alkoxyimino group", $C_2$-$C_3$ alkenyl group, $C_2$-$C_3$ alkylcarbonyl group, benzoyl group, carboxyl group, $C_2$-$C_3$ alkoxycarbonyl group, carbamoyl group, di($C_1$-$C_2$ alkyl)carbamoyl group, "phenyl group optionally substituted with same or different 1 to 2 substituents selected from the group consisting of a chlorine atom, bromine atom, $C_1$-$C_2$ alkyl group, "$C_1$-$C_2$ alkyl group substituted with same 1 to 3 fluorine atoms or chlorine atoms", cyclopropyl group, cyano group and tri($C_1$-$C_2$ alkyl)silyl group", furyl group, thienyl group, "amino group optionally substituted with same 1 to 2 $C_1$-$C_2$ alkyl group, or with $C_2$-$C_3$ alkylcarbonyl group, $C_2$-$C_3$ alkoxycarbonyl group, di($C_1$-$C_2$ alkyl)carbamoyl group or $C_1$-$C_2$ alkylsulfonyl group", nitro group, hydroxyl group, $C_1$-$C_2$ alkoxy group, $C_1$-$C_2$ haloalkoxy group, phenoxy group, $C_1$-$C_2$ alkylthio group, phenylthio group, $C_1$-$C_2$ alkylsulfinyl group or $C_1$-$C_2$ alkylsulfonyl group.

In the present invention, the "$C_4$-$C_{10}$ bicycloalkyl group" is a bicyclic hydrocarbon having 4 to 10 carbon atoms, examples of which include a bicyclobutyl, bicyclopentyl, bicyclohexyl, bicycloheptyl, bicyclooctyl, bicyclononyl or bicyclodecyl group, preferably a bicyclohexyl or bicycloheptyl group, more preferably a bicyclo[3.1.0]hexyl or bicyclo[4.1.0]heptyl group, and even more preferably a bicyclo[3.1.0]hexan-6-yl group.

In the present invention, the "optionally substituted benzoyl group (wherein said substituent is a substituent selected from the substituent group A)" is a benzoyl group optionally substituted with same or different 1 to 5 substituents selected from the group consisting of the aforementioned "halogen atom", the aforementioned "$C_1$-$C_6$ alkyl group", the aforementioned "$C_1$-$C_6$ haloalkyl group", the aforementioned "$C_3$-$C_6$ cycloalkyl group", cyano group and the aforementioned "tri($C_1$-$C_6$ alkyl)silyl group", examples of which include a benzoyl, fluorobenzoyl, difluorobenzoyl, trifluorobenzoyl, chlorobenzoyl, dichlorobenzoyl, trichlorobenzoyl, fluorochlorobenzoyl, methylbenzoyl, dimethylbenzoyl, trimethylbenzoyl, tetramethylbenzoyl, pentamethylbenzoyl, ethylbenzoyl, fluoro(methyl)benzoyl, chloro(methyl)benzoyl, bromo(methyl)benzoyl, cyclopropylbenzoyl, cyclopropyl(fluoro)benzoyl, chloro(cyclopropyl)benzoyl, cyclopropyl(methyl)benzoyl, (trifluoromethyl)benzoyl or fluoro(trifluoromethyl)benzoyl group, preferably a benzoyl group optionally substituted with same or different 1 to 3 substituents selected from the group consisting of a fluorine atom, chlorine atom, bromine atom, $C_1$-$C_3$ alkyl group, "$C_1$-$C_3$ alkyl group substituted with same or different 1 to 3 substituents selected from the group consisting of a fluorine atom, chlorine atom and bromine atom", $C_3$-$C_4$ cycloalkyl group, cyano group and tri($C_1$-$C_3$ alkyl)silyl group, and more preferably a benzoyl, chlorobenzoyl, dichlorobenzoyl, methylbenzoyl, trifluorobenzoyl or cyanobenzoyl group.

In the present invention, the "optionally substituted phenylsulfonyl group (wherein said substituent is a substituent selected from the substituent group A)" is a phenylsulfonyl group optionally substituted with same or different 1 to 5 substituents selected from the group consisting of the aforementioned "halogen atom", the aforementioned "$C_1$-$C_6$ alkyl group", the aforementioned "$C_1$-$C_6$ haloalkyl group", the aforementioned "$C_3$-$C_6$ cycloalkyl group", cyano group and the aforementioned "tri($C_1$-$C_6$ alkyl)silyl group", examples of which include a phenylsulfonyl, fluorophenylsulfonyl, difluorophenylsulfonyl, trifluorophenylsulfonyl, chlorophenylsulfonyl, dichlorophenylsulfonyl, trichlorophenylsulfonyl, fluorochlorophenylsulfonyl, methylphenylsulfonyl, dimethylphenylsulfonyl, trimethylphenylsulfonyl, tetramethylphenylsulfonyl, pentamethylphenylsulfonyl, ethylphenylsulfonyl, fluoro(methyl)phenylsulfonyl, chloro(methyl)phenylsulfonyl, bromo(methyl)phenylsulfonyl, cyclopropylphenylsulfonyl, cyclopropyl(fluoro)phenylsulfonyl, chloro(cyclopropyl)phenylsulfonyl, cyclopropyl(methyl)phenylsulfonyl, (trifluoromethyl)phenylsulfonyl or fluoro(trifluoromethyl)phenylsulfonyl group, preferably a phenylsulfonyl group optionally substituted with 1 to 3 same or different substituents selected from the group consisting of a fluorine atom, chlorine atom, bromine atom, $C_1$-$C_3$ alkyl group, "$C_1$-$C_3$ alkyl group substituted with same or different 1 to 3 substituents selected from the group consisting of a fluorine atom, chlorine atom and bromine atom", $C_3$-$C_4$ cycloalkyl group, cyano group and tri($C_1$-$C_3$ alkyl)silyl group, and more preferably a phenylsulfonyl, chlorophenylsulfonyl, methylphenylsulfonyl, trifluorophenylsulfonyl or cyanophenylsulfonyl group.

In the present invention, the "di($C_1$-$C_6$ alkyl)sulfamoyl group" is a sulfamoyl group in which same or different two aforementioned "$C_1$-$C_6$ alkyl groups" are bonded to nitrogen atoms, examples of which include a dimethylsulfamoyl, methylethylsulfamoyl, diethylsulfamoyl, dipropylsulfamoyl, dibutylsulfamoyl or dihexylsulfamoyl, preferably a sulfamoyl group in which same or different two $C_1$-$C_3$ alkyl groups are bonded, more preferably a dimethylsulfamoyl or diethylsulfamoyl group, and even more preferably a dimethylsulfamoyl group.

In the present invention, the "optionally substituted 3 to 6 membered heterocyclic group (wherein said heterocyclic group contains one nitrogen atom, oxygen atom or sulfur atom therein, may further contain 1 to 2 nitrogen atoms, may be condensed with a benzene ring, and said substituent is a substituent selected from substituent group E)" is a "3 to 6 membered heterocyclic group which contains one nitrogen atom, oxygen atom or sulfur atom as heteroatoms, and may further contain 1 to 2 nitrogen atoms", optionally substituted with 1 to 3 same or different substituents selected from the group consisting of the aforementioned "halogen atom", the aforementioned "$C_1$-$C_6$ alkyl group", the aforementioned "$C_1$-$C_6$ haloalkyl group", a hydroxyl group, the aforementioned "optionally substituted phenylsulfonyl group (wherein said substituent is a substituent selected from substituent group A)" and the aforementioned "di($C_1$-$C_6$ alkyl)sulfamoyl group", and which may be condensed with a benzene ring, preferably a "3 to 6 membered heterocyclic group which contains one nitrogen atom, oxygen atom or sulfur atom as heteroatoms, and which may further contain 1 nitrogen atom", optionally substituted with 1 to 2 same or different substituents selected from the group consisting of a fluorine atom, chlorine atom, bromine atom, $C_1$-$C_3$ alkyl group and "$C_1$-$C_3$ alkyl group substituted with 1 to 3 same or different substituents selected from the group consisting of a fluorine atom, chlorine atom and bromine atom", or a hydroxyl group, "phenylsulfonyl group optionally substituted with 1 to 3 same or different substituents selected from the group consisting of a fluorine atom, chlorine atom, bromine atom, $C_1$-$C_3$ alkyl group, "$C_1$-$C_3$ alkyl group substituted with 1 to 3 same or different substituents selected from the group consisting of a fluorine atom, chlorine atom and bromine atom", $C_3$-$C_4$ cycloalkyl group, cyano group and tri($C_1$-$C_3$ alkyl)silyl group" or "sulfamoyl group to which two same or different $C_1$-$C_3$ alkyl groups are bonded", and which may be condensed with a benzene ring, more preferably an aziridine, oxiranyl, oxetanyl, pyrrolyl, furyl, thienyl, pyrazolyl, thiazolyl, pyridyl, benzimidazolyl or benzothiazolyl group optionally substituted with 1 to 2 same substituents selected from the group consisting of a chlorine atom, bromine atom, methyl group, ethyl group and trifluoromethyl group, or a hydroxyl group, phenylsulfonyl group, tolylsulfonyl group or dimethylsulfamoyl group, and even more preferably a thienyl, pyrazolyl or thiazolyl group optionally substituted with 1 to 2 same or different substituents selected from the group consisting of a chlorine atom, methyl group and trifluoromethyl group.

In the present invention, the "($C_1$-$C_6$ alkoxy)$C_1$-$C_6$ alkoxy group" is an alkoxy group having 1 to 6 carbon atoms to which an alkoxy group having 1 to 6 carbon atoms is bonded, examples of which include a methoxymethoxy, ethoxymethoxy, propoxymethoxy, butoxymethoxy, s-butoxymethoxy, t-butoxymethoxy, pentyloxymethoxy, hexyloxymethoxy, methoxyethoxy, ethoxyethoxy, propoxyethoxy, butoxyethoxy, methoxypropoxy, methoxybutoxy, methoxypentyloxy or methoxyhexyloxy group, preferably an alkoxy group having 1 to 3 carbon atoms substituted with an alkoxy group having 1 to 3 carbon atoms, and more preferably a methoxyethoxy, ethoxyethoxy or ethoxymethoxy group.

In the present invention, the "optionally substituted phenoxy group (wherein said substituent is a hydroxyl group or a pyridazinyloxy group substituted with a halogen atom and/or $C_1$-$C_6$ alkoxy group)" is a phenoxy group optionally substituted with one hydroxyl group, or a phenoxy group substituted with pyridazinyloxy group substituted with same or different 1 to 3 substituents selected from the group consisting of the aforementioned "halogen atom" and the aforementioned "$C_1$-$C_6$ alkoxy group", preferably a hydroxyphenoxy group, or a phenoxy group substituted with a pyridazinyloxy group substituted with same or different 1 to 2 substituents selected from the group consisting of a fluorine atom, chlorine atom, bromine atom and $C_1$-$C_3$ alkoxy group, more preferably a phenoxy group substituted with a pyridazinyloxy group substituted with each one of chlorine atom, and methoxy or ethoxy group.

In the present invention, the "optionally substituted 5 to 6 membered heterocyclooxy group (wherein said heterocyclic ring contains one nitrogen atom, oxygen atom or sulfur atom therein, may further contain 1 to 2 nitrogen atoms, and said substituent is a substituent selected from substituent group E)" is a "5 to 6 membered heterocyclooxy group which contains one nitrogen atom, oxygen atom or sulfur atom as a heteroatom, and may further contain 1 to 2 nitrogen atoms" optionally substituted with same or different 1 to 2 substituents selected from the group consisting of the aforementioned "halogen atom", the aforementioned "$C_1$-$C_6$ alkyl group", the aforementioned "$C_1$-$C_6$ haloalkyl group", hydroxyl group, the aforementioned "optionally substituted phenylsulfonyl group (wherein said substituent is a substituent selected from substituent group A)" and the aforementioned "di($C_1$-$C_6$ alkyl)sulfamoyl group", preferably a "5 to 6 membered heterocyclooxy group which contains one nitrogen atom, oxygen atom or sulfur atom as a heteroatom, and may further contain one nitrogen atom" optionally substituted with same or different 1 to 2 substituents selected from the group consisting of a fluorine atom, chlorine atom, bromine atom, $C_1$-$C_3$ alkyl group, "$C_1$-$C_3$ alkyl group substituted with same or different 1 to 3 substituents selected from the group consisting of a fluorine atom, chlorine atom and bromine atom", hydroxyl group, "phenylsulfonyl group optionally substituted with same or different 1 to 3 substituents selected from the group consisting of a fluorine atom, chlorine atom, bromine atom, $C_1$-$C_3$ alkyl group, "$C_1$-$C_3$ alkyl group substituted with same or different 1 to 3 substituents selected from the group consisting of a fluorine atom, chlorine atom and bromine atom", $C_3$-$C_4$ cycloalkyl group, cyano group and tri($C_1$-$C_3$ alkyl)silyl group" and "sulfamoyl group to which same or different two $C_1$-$C_3$ alkyl groups are bonded", more preferably a pyridyloxy, pyrrolyloxy, furyloxy, thienyloxy, pyrazolyloxy, thiazolyloxy, pyrimidyloxy, pyrazinyloxy or pyridazinyloxy group optionally substituted with different 1 to 2 substituents selected from the group consisting of a chlorine atom, bromine atom, methyl group, ethyl group, trifluoromethyl group, hydroxyl group, phenylsulfonyl group, tolylsulfonyl group and dimethylsulfamoyl group, and even more preferably a pyridazinyloxy group optionally substituted with chlorine atom and hydroxyl group.

In the present invention, the "optionally substituted $C_2$-$C_7$ alkylcarbonyloxy group (wherein said substituent is a substituent selected from substituent group B)" is an oxy group to which the aforementioned "$C_2$-$C_7$ alkylcarbonyl group" is bonded, the aforementioned "$C_2$-$C_7$ alkylcarbonyl group" optionally substituted with the aforementioned "halogen atom", or the aforementioned "$C_3$-$C_6$ cycloalkyl group", cyano group, the aforementioned "$C_2$-$C_7$ alkylcarbonyl group", the aforementioned "$C_2$-$C_7$ alkoxycarbonyl group", phenyl group, the aforementioned "$C_1$-$C_6$ alkoxy group", the aforementioned "$C_1$-$C_6$ alkylthio group", the aforementioned "$C_1$-$C_6$ alkylsulfinyl group", the aforementioned "$C_1$-$C_6$ alkylsulfonyl group", the aforementioned "$C_1$-$C_4$ alkylenedioxy group", hydroxyimino group or the aforementioned "$C_1$-$C_6$ alkoxyimino group", examples of which include an acetyloxy, propionyloxy, butyryloxy, isobutyryloxy, valeryloxy, isovaleryloxy, pivaloyloxy, hexanoyloxy, heptanoyloxy, fluoroacetyl, difluoroacetyloxy, trifluoroacetyloxy, 2,2,2-trichloropropionyloxy, cyclopropylacetyloxy, cyanoacetyloxy, acetylacetyloxy, acetylpropionyloxy, methoxycarbonylacetyloxy, methoxycarbonylpropionyloxy, ethoxycarbonyacetyloxy, ethoxycarbonypropionyloxy, phenylacetyloxy, methoxyacetyloxy, methoxypropionyloxy, ethoxyacetyloxy, ethoxypropionyloxy, methylthioacetyloxy, methylthiopropionyloxy, ethylthioacetyloxy, ethylthiopropionyloxy, methylsulfinylacetyloxy, methylsulfonylacetyloxy, 2-(1,3-dioxolanyl)acetyloxy, hydroxyiminoacetyloxy or methoxyiminoacetyloxy group, preferably an oxy group to which a linear or branched alkylcarbonyl group having 2 to 5 carbon atoms is bonded ($C_2$-$C_5$ alkylcarbonyloxy group), even more preferably an oxy group to which a linear or branched alkylcarbonyl group having 2 to 4 carbon atoms is bonded($C_2$-$C_4$ alkylcarbonyloxy group), particularly preferably an acetyloxy, propionyloxy, valeryloxy or pivaloyloxy group, and most preferably an acetyloxy group.

In the present invention, the "optionally substituted $C_2$-$C_7$ alkoxycarbonyloxy group (wherein said substituent is a substituent selected from substituent group B)" is an oxy group to which the aforementioned "$C_2$-$C_7$ alkoxycarbonyl group" is bonded, the aforementioned "$C_2$-$C_7$ alkoxycarbonyl group" optionally substituted with the aforementioned "halogen atom" or the aforementioned "$C_3$-$C_6$ cycloalkyl group", cyano group, the aforementioned "$C_2$-$C_7$ alkylcarbonyl group", the aforementioned "$C_2$-$C_7$ alkoxycarbonyl group", phenyl group, the aforementioned "$C_1$-$C_6$ alkoxy group", the aforementioned "$C_1$-$C_6$ alkylthio group", the aforementioned "$C_1$-$C_6$ alkylsulfinyl group", the aforementioned "$C_1$-$C_6$ alkylsulfonyl group", the aforementioned "$C_1$-$C_4$ alkylenedioxy group", hydroxyimino group or the aforementioned "$C_1$-$C_6$ alkoxyimino group", examples of which include a methoxycarbonyloxy, ethoxycarbonyloxy, propoxycarbonyloxy, isopropoxycarbonyloxy, butoxycarbonyloxy, isobutoxycarbonyloxy, s-butoxycarbonyloxy, t-butoxycarbonyloxy, pentoxycarbonyloxy, isopentoxycarbonyloxy, 2-methylbutoxycarbonyloxy, neopentoxycarbonyloxy, 1-ethylpropoxycarbonyloxy, hexyloxycarbonyloxy, 4-methylpentoxycarbonyloxy, 3-methylpentoxycarbonyloxy, 2-methylpentoxycarbonyloxy, 1-methylpentoxycarbonyloxy, 3,3-dimethylbutoxycarbonyloxy, 2,2-dimethylbutoxycarbonyloxy, 1,1-dimethylbutoxycarbonyloxy, 1,2-dimethylbutoxycarbonyloxy, 1,3-dimethylbutoxycarbonyloxy, 2,3-dimethylbutoxycarbonyloxy, 2-ethylbutoxycarbonyloxy, fluoromethoxycarbonyloxy, difluoromethoxycarbonyloxy, trifluoromethoxycarbonyloxy, 2,2,2-trichloroethoxycarbonyloxy, cyclopropylmethoxycarbonyloxy, cyanomethoxycarbonyloxy, acetylmethoxycarbonyloxy, acetylethoxycarbonyloxy, methoxycarbonylmethoxycarbonyloxy, methoxycarbonylethoxycarbonyloxy, ethoxycarbonylmethoxycarbonyloxy, ethoxycarbonylethoxycarbonyloxy, phenylmethoxycarbonyloxy, methoxymethoxycarbonyloxy, methoxyethoxycarbonyloxy, ethoxymethoxycarbonyloxy, ethoxyethoxycarbonyloxy, methylthiomethoxycarbonyloxy, methylthioethoxycarbonyloxy, ethylthiomethoxycarbonyloxy, ethylthioethoxycarbonyloxy, methylsulfinylmethoxycarbonyloxy, methylsulfonylmethoxycarbonyloxy, 2-(1,3-dioxolanyl)methoxycarbonyloxy, hydroxyiminomethoxycarbonyloxy or methoxyiminomethoxycarbonyloxy group, preferably an oxy group to which a linear or branched alkoxycarbonyl group having 2 to 5 carbon atoms is bonded ($C_2$-$C_5$ alkoxycarbonyloxy group), even more preferably an oxy group to which a linear or branched alkoxycarbonyl group having 2 to 4 carbon atoms is bonded ($C_2$-$C_4$ alkoxycarbonyloxy group), particularly preferably a methoxycarbonyloxy, ethoxycarbonyloxy, propoxycarbonyloxy or t-butoxycarbonyl oxy group, and most preferably a methoxycarbonyloxy group.

In the present invention, the "optionally substituted benzoyloxy group (wherein said substituent is a substituent selected from substituent group A)" is a benzoyloxy group optionally substituted with same or different 1 to 5 substituents selected from the group consisting of the aforementioned "halogen atom", the aforementioned "$C_1$-$C_6$ alkyl group", the aforementioned "$C_1$-$C_6$ haloalkyl group", the aforementioned "$C_3$-$C_6$ cycloalkyl group", cyano group and the aforementioned "tri($C_1$-$C_6$ alkyl)silyl group", examples of which include a benzoyloxy, fluorobenzoyloxy, difluorobenzoyloxy, trifluorobenzoyloxy, chlorobenzoyloxy, dichlorobenzoyloxy, trichlorobenzoyloxy, fluorochlorobenzoyloxy, methylbenzoyloxy, dimethylbenzoyloxy, trimethylbenzoyloxy, tetramethylbenzoyloxy, pentamethylbenzoyloxy, ethylbenzoyloxy, fluoro(methyl)benzoyloxy, chloro(methyl)benzoyloxy, bromo(methyl)benzoyloxy, cyclopropylbenzoyloxy, cyclopropyl(fluoro)benzoyloxy, chloro(cyclopropyl)benzoyloxy, cyclopropyl(methyl)benzoyloxy, (trifluoromethyl)benzoyloxy or fluoro(trifluoromethyl)benzoyloxy group, preferably a benzoyloxy group optionally substituted with same or different 1 to 3 substituents selected from the group consisting of a fluorine atom, chlorine atom, bromine atom, $C_1$-$C_3$ alkyl group, "$C_1$-$C_3$ alkyl group substituted with same or different 1 to 3 substituents selected from the group consisting of a fluorine atom, chlorine atom and bromine atom", $C_3$-$C_4$ cycloalkyl group, cyano group and tri($C_1$-$C_3$ alkyl)silyl group, and more preferably a benzoyloxy, chlorobenzoyloxy, methylbenzoyloxy, trifluorobenzoyloxy or cyanobenzoyloxy group.

In the present invention, the "optionally substituted phenylsulfonyloxy group (wherein said substituent is a substituent selected from substituent group A)" is a phenylsulfonyloxy group optionally substituted with same or different 1 to 5 substituents selected from the group consisting of the aforementioned "halogen atom", the aforementioned "$C_1$-$C_6$ alkyl group", the aforementioned "$C_1$-$C_6$ haloalkyl group", the aforementioned "$C_3$-$C_6$ cycloalkyl group", cyano group and the aforementioned "tri($C_1$-$C_6$ alkyl)silyl group", examples of which include a phenylsulfonyloxy, fluorophenylsulfonyloxy, difluorophenylsulfonyloxy, trifluorophenylsulfonyloxy, chlorophenylsulfonyloxy, dichlorophenylsulfonyloxy, trichlorophenylsulfonyloxy, fluorochlorophenylsulfonyloxy, methylphenylsulfonyloxy, dimethylphenylsulfonyloxy, trimethylphenylsulfonyloxy, tetramethylphenylsulfonyloxy, pentamethylphenylsulfonyloxy, ethylphenylsulfonyloxy, fluoro(methyl)phenylsulfonyloxy, chloro(methyl)phenylsulfonyloxy, bromo(methyl)phenylsulfonyloxy, cyclopropylphenylsulfonyloxy, cyclopropyl(fluoro)phenylsulfonyloxy, chloro(cyclopropyl)phenylsulfonyloxy, cyclopropyl(methyl)phenylsulfonyloxy, (trifluoromethyl)phenylsulfonyloxy or fluoro(trifluoromethyl)phenylsulfonyloxy group, preferably a phenylsulfonyloxy group optionally substituted with same or different 1 to 3 substituents selected from the group consisting of a fluorine atom, chlorine atom, bromine atom, $C_1$-$C_3$ alkyl group, "$C_1$-$C_3$ alkyl group substituted with same or different 1 to 3 substituents selected from the group consisting of a fluorine atom, chlorine atom and bromine atom", $C_3$-$C_4$ cycloalkyl group, cyano group and tri($C_1$-$C_3$ alkyl)silyl group, and more preferably a phenylsulfonyloxy, chlorophenylsulfonyloxy, methylphenylsulfonyloxy, trifluorophenylsulfonyloxy or cyanophenylsulfonyloxy group.

In the present invention, the "hydroxy $C_1$-$C_6$ alkyl group" is the aforementioned "$C_1$-$C_6$ alkyl group" substituted with a hydroxy group, examples of which include a hydroxymethyl, 1-hydroxyethyl, 2-hydroxyethyl, 1-hydroxypropyl, 2-hydroxypropyl, 3-hydroxypropyl, 1-hydroxy-1-methylethyl, 2-hydroxy-1-methylethyl, 4-hydroxybutyl, 5-hydroxypentyl, and 6-hydroxyhexyl group, preferably a 3-hydroxypropyl group.

In the present invention, the "two adjacent $R^1$, $R^2$, $R^3$ and $R^4$ may together with carbon atoms respectively bonded thereto form an optionally substituted 3 to 6 membered cyclic hydrocarbon group (wherein said cyclic hydrocarbon may be interrupted by 1 to 2 same or different heteroatoms selected from the group consisting of a nitrogen atom, oxygen atom and sulfur atom, said substituent is a halogen atom, $C_1$-$C_6$ alkyl group, hydroxy $C_1$-$C_6$ alkyl group, $C_1$-$C_6$ alkoxy group, oxo group, hydroxyimino group or $C_1$-$C_6$ alkoxyimino group, and in the case the cyclic hydrocarbon is substituted with a $C_1$-$C_6$ alkyl group, a new 3-membered ring may be formed by bonding with other $C_1$-$C_6$ alkyl groups or carbon atoms on the ring)" is a saturated or unsaturated 3 to 6 membered cyclic hydrocarbon group optionally substituted with same or different 1 to 4 substituents selected from the group consisting of the aforementioned "halogen atom", the aforementioned "$C_1$-$C_6$ alkyl group", the aforementioned "$C_1$-$C_6$ alkyl group" substituted with 1 to 2 hydroxyl groups, the aforementioned "$C_1$-$C_6$ alkoxy group", oxo group, hydroxyimino group and the aforementioned "$C_1$-$C_6$ alkoxyimino group", which may be interrupted by same or different 1 to 2 heteroatoms selected from the group consisting of a nitrogen atom, oxygen atom and sulfur atom, and further may form a cyclopropane ring on the ring, preferably a group represented by —$CH_2$—, —$CH_2CH_2$—, —$CH_2CH_2CH_2$—, —$CH(CH_3)CH_2CH_2$—, —$CH_2CH(CH_3)CH_2$—, —$C(CH_3)_2CH_2CH_2$—, —$CH_2C(CH_3)_2CH_2$—, —$CH(OCH_3)CH_2CH_2$—, —$C(OCH_3)_2CH_2CH_2$—, —$CH_2C(OCH_3)_2H_2$—, —$C(=O)CH_2CH_2$—, —$CH_2C(=O)CH_2$—, —$C(=NOCH_3)CH_2CH_2$—, —$CH_2CH_2CH_2CH_2$—, —$CH(CH_3)CH_2CH_2CH_2$—, —$C(CH_3)_2CH_2CH_2CH_2$—, —$CH(OCH_3)CH_2CH_2CH_2$—, —CH=CH—CH=CH—, —$OCH_2CH_2$—, —$OCH(CH_3)CH_2$—, —$OCH_2CH(CH_3)$—, —$OC(CH_3)_2CH_2$—, —OCH=CH—, —$OC(CH_3)$=CH—, —OCH=$C(CH_3)$—, —SCH=CH—, —N=CH—CH=CH—, —$OCH_2O$—, —$OCH(CH_3)O$—, —$OC(CH_3)_2O$—, —$OCF_2O$—, —$OCH_2CH_2O$—, —OCH=N—, —$OC(CH_3)$=N—,

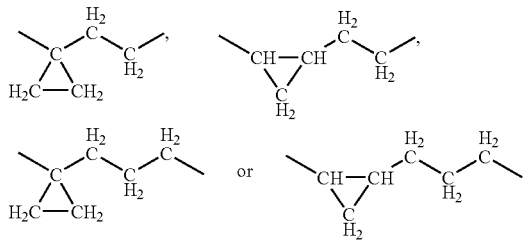

more preferably a group represented by —$CH_2CH_2$—, —$CH_2CH_2CH_2$—, —$CH(CH_3)CH_2CH_2$—, —$CH_2CH_2CH_2CH_2$—, —CH=CH—CH=CH—, —$OCH_2CH_2$—, —OCH=CH—, —OCH=$C(CH_3)$—, —SCH=CH—, —N=CH—CH=CH—, $OCH_2O$—, —$OCH_2CH_2O$—,

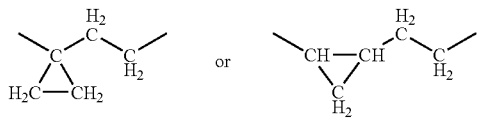

and even more preferably a group represented by —$CH_2CH_2CH_2$—, —$CH(CH_3)CH_2CH_2$—, —$OCH_2CH_2$—, —OCH=CH— or

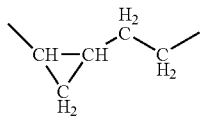

In the case a compound of the present invention is a salt, it may be, for example, an alkali metal salt, alkaline earth metal salt, ammonium salt or organic amine salt, and in the case a basic moiety is in the molecule, it may be a salt such as a sulfate salt, hydrochloride salt, nitrate salt or phosphate salt.

In the present invention, the "alkali metal salt" may be, for example, a sodium salt, potassium salt or lithium salt, preferably a sodium salt or potassium salt.

In the present invention, the "alkaline earth metal salt" may be, for example, a calcium salt or magnesium salt, preferably a magnesium salt.

In the present invention, the "organic amine salt" may be, for example, a methylamine salt, diethylamine salt, trimethylamine salt, triethylamine salt, diisopropylamine salt, tributylamine salt, 1,4-diazabicyclo[2.2.2]octane (DABCO) salt, 1,8-diazabicyclo[5.4.0]undec-7-ene (DBU) salt, pyridine salt, collidine salt, 4-(N,N-dimethylamino)pyridine salt, pyrrolidine salt, piperidine salt, piperazine salt, morpholine salt or N-methylmorpholine salt, preferably a triethylamine salt and pyridine salt.

In the present invention, the "metal residue" is any metal residue, examples of which include lithium, sodium, potassium, and copper, preferably lithium.

In the present invention, the "metal salt residue" is any metal salt residue, for example, a residue comprising metal and inorganic substance, examples of which include boronic acid, magnesium fluoride, magnesium chloride, magnesium bromide, magnesium iodide, aluminium dichloride, calcium chloride, calcium bromide, calcium iodide, titanium trichloride, manganese chloride, manganese bromide, manganese iodide, copper chloride, copper bromide, copper iodide, zinc chloride, zinc bromide, zinc iodide, trichloro tin, cerium dichloride, samarium iodide, europium iodide, and ytterbium iodide, preferably magnesium chloride, magnesium bromide, and magnesium iodide.

In the present invention, the "organometallic residue" is a residue comprising metal binding with organic group, examples of which include vinyl magnesium, dimethyl aluminium, diethyl aluminium, diisopropyl aluminium, divinyl aluminium, vinyl copper, vinyl(lithium)copper, vinyl(cyano)(lithium)copper, vinyl zinc, methyl zinc, trimethyl tin, tributyl tin, trivinyl tin, chlorodivinyl tin, butyl tellurium, and vinyl tellurium, preferably vinyl magnesium.

In the present invention, the "metal" is any metal, examples of which include lithium, boron, sodium, magnesium, aluminium, potassium, calcium, titanium, chromium, manganese, nickel, copper, zinc, zinc-copper alloy, silver, tin, tellurium, mercury, lithium-mercury alloy, cerium, europium, and ytterbium, preferably lithium, magnesium, copper, zinc, and copper-zinc alloy, more preferably magnesium.

In the present invention, the "metal salt" is any metal salt, for example, salt with the aforementioned "metal" and inorganic substance, examples of which include magnesium difluoride, magnesium dichloride, magnesium dibromide, magnesium diiodide, aluminium trichloride, manganese chloride, manganese bromide, nickel tetracarbonyl, copper chloride, copper bromide, copper iodide, zinc chloride, zinc bromide, zinc iodide, cerium chloride, and samarium iodide, preferably magnesium dichloride, magnesium dibromide, magnesium diiodide, copper chloride, copper bromide, copper iodide, zinc chloride, zinc bromide, and zinc iodide.

In the present invention, the "organometallic compound" is a compound comprising metal binding with organic group, examples of which include methyllithium, butyllithium, t-butyllithium, phenyllithium, methylmagnesium chloride, methylmagnesium bromide, methylmagnesium iodide, ethylmagnesium bromide, t-butylmagnesium chloride, and t-butylmagnesium bromide, preferably methyl lithium, butyl lithium, t-butyllithium, and t-butylmagnesium chloride.

A solvate of a compound of the present invention is also included in the present invention.

In the compounds of the present invention, there are compounds having an asymmetric carbon(s), and in that case, the present invention also includes any kind of optical isomers and mixtures of several kinds of optical isomers in any optional ratio.

The following provides an explanation of compounds used in the process of the present invention as well as compounds of the present invention.

(a) In each compound used in the process of the present invention, although substituents $R^1$ to $R^4$ are as previously described, they each independently represent preferably a hydrogen atom, fluorine atom, chlorine atom, bromine atom, iodine atom, optionally substituted $C_1$-$C_4$ alkyl group (wherein said substituent is 1 to 3 same or different substituents selected from the group consisting of a fluorine atom, chlorine atom and bromine atom, or a $C_3$-$C_4$ cycloalkyl group, $C_1$-$C_3$ alkylthio group or $C_1$-$C_3$ alkoxyimino group), $C_2$-$C_3$ alkenyl group, $C_2$-$C_3$ alkynyl group, optionally substituted $C_3$-$C_5$ cycloalkyl group (wherein said substituent is 1 to 3 same or different substituents selected from the group consisting of a fluorine atom, chlorine atom, bromine atom, $C_1$-$C_3$ alkyl group, $C_3$-$C_4$ cycloalkyl group, cyano group, $C_1$-$C_3$ alkoxy group and $C_1$-$C_3$ alkylthio group), $C_6$-$C_7$ bicycloalkyl group, cyano group, $C_2$-$C_4$ alkylcarbonyl group, $C_2$-$C_4$ alkoxycarbonyl group, optionally substituted phenyl group {wherein said substituent is a fluorine atom, chlorine atom, bromine atom, $C_1$-$C_3$ alkyl group or $C_1$-$C_3$ haloalkyl group (wherein said halogen atom is 1 to 3 same or different halogen atoms selected from the group consisting of a fluorine atom, chlorine atom and bromine atom)}, optionally substituted 5 to 6 membered heterocyclic group {wherein said heterocyclic ring contains one nitrogen atom, oxygen atom or sulfur atom therein, may further contain 1 to 2 nitrogen atoms, and said substituent is 1 to 2 same or different substituents selected from the group consisting of a fluorine atom, chlorine atom, bromine atom, $C_1$-$C_3$ alkyl group and $C_1$-$C_3$ haloalkyl group (wherein said halogen atom is 1 to 3 same or different halogen atoms selected from the group consisting of a fluorine atom, chlorine atom and bromine atom)}, nitro group, $C_1$-$C_3$ alkoxy group, $C_1$-$C_3$ haloalkoxy group (wherein said halogen atom is 1 to 3 same or different halogen atoms selected from the group consisting of a fluorine atom, chlorine atom and bromine atom), optionally substituted phenoxy group (wherein said substituent is a pyridazinyloxy group substituted with a fluorine atom, chlorine atom, bromine atom and/or $C_1$-$C_3$ alkoxy group), or $C_1$-$C_3$ alkylthio group, or two adjacent $R^1$, $R^2$, $R^3$ and $R^4$ together form a group represented by —CH$_2$CH$_2$—, —CH$_2$CH$_2$CH$_2$—, —CH(CH$_3$)CH$_2$CH$_2$—, —CH$_2$CH$_2$CH$_2$CH$_2$—, —CH=CH—CH=CH—, —OCH$_2$CH$_2$—, —OCH=CH—, —OCH=C(CH$_3$)—, —SCH=CH—, —N=CH—CH=CH—, —OCH$_2$O—, —OCH$_2$CH$_2$O—,

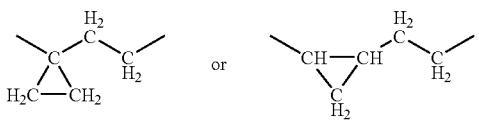

more preferably each independently represent a hydrogen atom, fluorine atom, chlorine atom, bromine atom, iodine atom, optionally substituted $C_1$-$C_4$ alkyl group (wherein said substituent is 1 to 3 fluorine atoms or one cyclopropyl group), $C_2$-$C_3$ alkenyl group, optionally substituted $C_3$-$C_4$ cycloalkyl group (wherein said substituent is 1 to 2 same substituents selected from the group consisting of a fluorine atom, chlorine atom, bromine atom, $C_1$-$C_2$ alkyl group, cyclopropyl group and $C_1$-$C_2$ alkoxy group), cyano group, $C_2$-$C_3$ alkoxycarbonyl group, nitro group, $C_1$-$C_3$ alkoxy group or trifluoromethoxy group, or two adjacent $R^1$, $R^2$, $R^3$ and $R^4$ together form a group represented by —CH$_2$CH$_2$CH$_2$—, —CH(CH$_3$)CH$_2$CH$_2$—, —OCH$_2$CH$_2$—, —OCH=CH— or

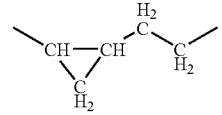

provided that $R^1$ is not a hydrogen atom;

even more preferably each independently represent a hydrogen atom, fluorine atom, chlorine atom, bromine atom, iodine atom, $C_1$-$C_3$ alkyl group, $C_2$-$C_3$ alkenyl group, optionally substituted $C_3$-$C_4$ cycloalkyl group (wherein said substituent is 1 to 2 same substituents selected from the group consisting of a chlorine atom and a $C_1$-$C_2$ alkyl group), cyano group or $C_1$-$C_2$ alkoxy group, or two adjacent $R^1$, $R^2$, $R^3$ and $R^4$ together form a group represented by —CH$_2$CH$_2$CH$_2$— or —OCH=CH—, provided that $R^1$ is not a hydrogen atom;

particularly preferably each independently represent a hydrogen atom, fluorine atom, chlorine atom, bromine atom, iodine atom, methyl group, ethyl group, allyl group, isopropyl group, optionally substituted cyclopropyl group (wherein said substituent is two chlorine atoms) or a methoxy group, or two adjacent $R^1$, $R^2$, $R^3$ and $R^4$ together form a group represented by —CH$_2$CH$_2$CH$_2$— or —OCH=CH—, provided that $R^1$ is not a hydrogen atom;

more particularly preferably $R^1$ is a fluorine atom, chlorine atom, bromine atom, iodine atom, methyl group, ethyl group, isopropyl group, cyclopropyl group or methoxy group, and $R^2$, $R^3$ and $R^4$ each independently represent a hydrogen atom or methyl group; and most preferably $R^1$ is a fluorine atom, chlorine atom, bromine atom, iodine atom or methyl group, and $R^2$, $R^3$ and $R^4$ are hydrogen atoms.

(b) In the present invention, Z is preferably a hydrogen atom.

(c) In the present invention, $Y^1$, $Y^2$ and $Y^3$ are preferably hydrogen atoms.

(d) In the present invention, $R^5$ is preferably a methyl group.

(e) In the present invention, X is preferably a bromine atom.

(f) In the present invention, W is preferably a carbonyl group.

In compounds used in the process of the present invention and compounds of the present invention, preferably:

(1a) $R^1$, $R^2$, $R^3$ and $R^4$ each independently represent a hydrogen atom, fluorine atom, chlorine atom, bromine atom, iodine atom, optionally substituted $C_1$-$C_4$ alkyl group (wherein said substituent is 1 to 3 same or different substituents selected from the group consisting of a fluorine atom, chlorine atom and bromine atom, or a $C_3$-$C_4$ cycloalkyl group, $C_1$-$C_3$ alkylthio group or $C_1$-$C_3$ alkoxyimino group), $C_2$-$C_3$ alkenyl group, $C_2$-$C_3$ alkynyl group, optionally substituted $C_3$-$C_5$ cycloalkyl group (wherein said substituent is 1 to 3 same or different substituents selected from the group consisting of a fluorine atom, chlorine atom, bromine atom, $C_1$-$C_3$ alkyl group, $C_3$-$C_4$ cycloalkyl group, cyano group, $C_1$-$C_3$ alkoxy group and $C_1$-$C_3$ alkylthio group), $C_6$-$C_7$ bicycloalkyl group, cyano group, $C_2$-$C_4$ alkylcarbonyl group, $C_2$-$C_4$ alkoxycarbonyl group, optionally substituted phenyl group {wherein said substituent is a fluorine atom, chlorine atom, bromine atom, $C_1$-$C_3$ alkyl group or $C_1$-$C_3$ haloalkyl group (wherein said halogen atom is 1 to 3 same or different halogen atoms selected from the group consisting of a fluorine atom, chlorine atom and bromine atom)}, optionally substituted 5 to 6 membered heterocyclic group {wherein said heterocyclic ring contains one nitrogen atom, oxygen atom or sulfur atom therein, may further contain 1 to 2 nitrogen atoms, and said substituent is 1 to 2 same or different substituents selected from the group consisting of a fluorine atom, chlorine atom, bromine atom, $C_1$-$C_3$ alkyl group and $C_1$-$C_3$ haloalkyl group (wherein said halogen atom is 1 to 3 same or different halogen atoms selected from the group consisting of a fluorine atom, chlorine atom and bromine atom)}, nitro group, $C_1$-$C_3$ alkoxy group, $C_1$-$C_3$ haloalkoxy group (wherein said halogen atom is 1 to 3 same or different halogen atoms selected from the group consisting of a fluorine atom, chlorine atom and bromine atom), optionally substituted phenoxy group (wherein said substituent is a pyridazinyloxy group substituted with a fluorine atom, chlorine atom, bromine atom and/or $C_1$-$C_3$ alkoxy group), or $C_1$-$C_3$ alkylthio group, or two adjacent $R^1$, $R^2$, $R^3$ and $R^4$ together form a group represented by —$CH_2CH_2$—, —$CH_2CH_2CH_2$—, —$CH(CH_3)CH_2CH_2$—, —$CH_2CH_2CH_2CH_2$—, —$CH=CH-CH=CH$—, —$OCH_2CH_2$—, —$OCH=CH$—, —$OCH=C(CH_3)$—, —$SCH=CH$—, —$N=CH-CH=CH$—, —$OCH_2O$—, —$OCH_2CH_2O$—,

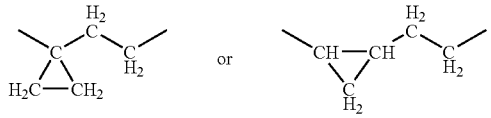

(1b) Z is a hydrogen atom, (1c) $Y^1$, $Y^2$ and $Y^3$ are hydrogen atoms, (1d) $R^5$ is a methyl group, (1e) X is a bromine atom, and (1f) W is a carbonyl group.

In compounds used in the process of the present invention and compounds of the present invention, more preferably:

(2a) $R^1$, $R^2$, $R^3$ and $R^4$ each independently represent a hydrogen atom, fluorine atom, chlorine atom, bromine atom, iodine atom, optionally substituted $C_1$-$C_4$ alkyl group (wherein said substituent is 1 to 3 fluorine atoms or one cyclopropyl group), $C_2$-$C_3$ alkenyl group, optionally substituted $C_3$-$C_4$ cycloalkyl group (wherein said substituent is 1 to 2 same substituents selected from the group consisting of a fluorine atom, chlorine atom, bromine atom, $C_1$-$C_2$ alkyl group, cyclopropyl group and $C_1$-$C_2$ alkoxy group), cyano group, $C_2$-$C_3$ alkoxycarbonyl group, nitro group, $C_1$-$C_3$ alkoxy group or trifluoromethoxy group, or two adjacent $R^1$, $R^2$, $R^3$, $R^4$ and $R^5$ together form a group represented by —$CH_2CH_2CH_2$—, —$CH(CH_3)CH_2CH_2$—, —$OCH_2CH_2$—, —$OCH=CH$— or

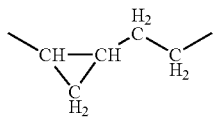

provided that $R^2$ is not a hydrogen atom, (2b) Z is a hydrogen atom, (2c) $Y^1$, $Y^2$ and $Y^3$ are hydrogen atoms, (2d) $R^5$ is a methyl group, (2e) X is a bromine atom, and (2f) W is a carbonyl group.

In compounds used in the process of the present invention and compounds of the present invention, even more preferably:

(3a) $R^1$, $R^2$, $R^3$ and $R^4$ each independently represent a hydrogen atom, fluorine atom, chlorine atom, bromine atom, iodine atom, $C_1$-$C_3$ alkyl group, $C_2$-$C_3$ alkenyl group, optionally substituted $C_3$-$C_4$ cycloalkyl group (wherein said substituent is 1 to 2 same substituents selected from the group consisting of a chlorine atom and $C_1$-$C_2$ alkyl group), cyano group or $C_1$-$C_2$ alkoxy group, or two adjacent $R^1$, $R^2$, $R^3$ and $R^4$ together form a group represented by —$CH_2CH_2CH_2$- or —$OCH=CH$—, provided that $R^2$ is not a hydrogen atom, (3b) Z is a hydrogen atom, (3c) $Y^1$, $Y^2$ and $Y^3$ are hydrogen atoms, (3d) $R^5$ is a methyl group, (3e) X is a bromine atom, and (3f) W is a carbonyl group.

In compounds used in the process of the present invention and compounds of the present invention, particularly preferably:

(4a) $R^1$, $R^2$, $R^3$ and $R^4$ each independently represent a hydrogen atom, fluorine atom, chlorine atom, bromine atom, iodine atom, methyl group, ethyl group, allyl group, isopropyl group, optionally substituted cyclopropyl group (wherein said substituent is two chlorine atoms) or methoxy group, or two adjacent $R^1$, $R^2$, $R^3$ and $R^4$ together form a group represented by —$CH_2CH_2CH_2$— or —$OCH=CH$—, provided that $R^1$ is not a hydrogen atom, (4b) Z is a hydrogen atom, (4c) $Y^1$, $Y^2$ and $Y^3$ are hydrogen atoms, (4d) $R^5$ is a methyl group, (4e) X is a bromine atom, and (4f) W is a carbonyl group.

Further, in compounds used in the process of the present invention and compounds of the present invention, particularly preferably:

(5a) $R^1$ is a fluorine atom, chlorine atom, bromine atom, iodine atom or methyl group, and $R^2$, $R^3$, and $R^4$ are hydrogen atoms, (5b) Z is a hydrogen atom, (5c) $Y^1$, $Y^2$ and $Y^3$ are hydrogen atoms, (5d) $R^5$ is a methyl group, (5e) X is a bromine atom, and (5f) W is a carbonyl group.

In another aspect of compounds used in the process of the present invention and compounds of the present invention, preferably:

(6a) $R^1$, $R^2$, $R^3$, and $R^4$ are hydrogen atoms, halogen atoms, or $C_1$-$C_6$ alkyl groups, (6b) Z is a hydrogen atom, (6c) $Y^1$, $Y^2$ and $Y^3$ are hydrogen atoms, (6d) $R^5$ is a $C_1$-$C_6$ alkyl group, (6e) W is a carbonyl group, and (6f) X is a chlorine atom, bromine atom, or iodine atom.

In another aspect of compounds used in the process of the present invention and compounds of the present invention, more preferably:

(7a) $R^1$ is a halogen atom, or $C_1$-$C_6$ alkyl group, and $R^2$, $R^3$, and $R^4$ are hydrogen atoms, (7b) Z is a hydrogen atom, (7c) $Y^1$, $Y^2$ and $Y^3$ are hydrogen atoms, (7d) $R^5$ is a $C_1$-$C_6$ alkyl group, (7e) W is a carbonyl group, and (7f) X is a chlorine atom, or bromine atom.

In another aspect of compounds used in the process of the present invention and compounds of the present invention, even more preferably:

(8a) $R^1$ is a fluorine atom, chlorine atom, bromine atom, or methyl group and $R^2$, $R^3$, and $R^4$ are hydrogen atoms, (8b) Z is a hydrogen atom, (8c) $Y^1$, $Y^2$ and $Y^3$ are hydrogen atoms, (8d) $R^5$ is a methyl group, (8e) W is a carbonyl group, and (8f) X is bromine atom.

Further, in each compound used in the process of the invention, $M^1$ is the above-mentioned metal residue, metal salt residue, or organometallic residue, and $M^2$ is the above-mentioned metal, metal salt, or organic metal compound.

$M^1$ may be any metal provided it is a metal which is bonded to a vinyl group and easily eliminated, and may be, particularly, lithium, boronic acid, sodium, magnesium, magnesium salt, aluminium, dialkyl aluminium, potassium, calcium, calcium salt, titanium, titanium salt, manganese, manganese salt, copper, copper salt, zinc, zinc salt, zinc alloy, tin, trialkyl tin, tellurium, alkyl tellurium, cerium, cerium salt, samarium, samarium salt, europium, europium salt, ytterbium, ytterbium salt, preferably lithium, boronic acid, magnesium, magnesium salt, aluminium, dialkyl aluminium, manganese, manganese salt, copper, copper salt, zinc, zinc salt, zinc alloy, tin, trialkyl tin, tellurium, alkyl tellurium, cerium, or cerium salt, more preferably magnesium, magnesium chloride, magnesium bromide, or magnesium iodide.

Further, $M^2$ is not particularly limited provided it may be converted into organic metallic compound by halogen-metal exchange reaction, and may be specifically, lithium, lithium alloy, sodium, magnesium, magnesium salt (e.g., magnesium chloride, magnesium bromide, magnesium iodide), potassium, nickel, nickel salt, copper, copper salt, zinc, zinc salt, zinc alloy (e.g., zinc-copper alloy, zinc-silver alloy), chromium, chromium salt, methyl lithium, butyllithium, t-butyllithium, phenyl lithium, methylmagnesium chloride, methylmagnesium bromide, phenyl magnesium chloride, phenyl magnesium bromide, or calcium, preferably lithium, lithium alloy, sodium, magnesium, magnesium salt, potassium, nickel, nickel salt, copper, copper salt, zinc, zinc salt, zinc alloy (particularly zinc-copper alloy), or t-butyllithium, more preferably magnesium, zinc, or zinc-copper alloy.

In another aspect of compounds used in the process of the present invention and compounds of the present invention, particularly preferably:

(9a) $R^1$ is a fluorine atom, chlorine atom, bromine atom, or methyl group and $R^2$, $R^3$, and $R^4$ are hydrogen atoms, (9b) Z is a hydrogen atom, (9c) $Y^1$, $Y^2$ and $Y^3$ are hydrogen atoms, (9d) $R^5$ is a methyl group, (9e) W is a carbonyl group, (9f) X is a bromine atom, (9g) $M^1$ is a magnesium chloride, and (9h) $M^2$ is a magnesium.

Further, the compound of general formula (3) of the present invention is that described above, preferably a compound wherein $R^1$ is a halogen atom or $C_1$-$C_6$ alkyl group, $R^2$, $R^3$ and $R^4$ are hydrogen atoms, and other groups are those described above. The compound of general formula (3) of the present invention is more preferably a compound wherein $R^1$ is a fluorine atom, chlorine atom, bromine atom, or methyl group, particularly preferably a methyl group, $R^2$, $R^3$, and $R^4$ are hydrogen atoms, Z is a hydrogen atom, and $Y^1$, $Y^2$, and $Y^3$ are hydrogen atoms.

The representative compound of the compounds of general formula (3) can include 2-(1-hydroxyl-2-propenyl)-6-methylphenol.

Further, the compound of general formula (7') of the present invention is that described above, preferably a compound wherein $R^1$, $R^2$, $R^3$, and $R^4$ are hydrogen atoms, halogen atoms, or $C_1$-$C_6$ alkyl groups, Z is a hydrogen atom, $Y^1$, $Y^2$ and $Y^3$ are hydrogen atoms, $R^5$ is a $C_1$-$C_6$ alkyl group, W is a group CO, and X is a chlorine atom, bromine atom, or iodine atom, more preferably a compound wherein $R^1$ is a halogen atom or $C_1$-$C_6$ alkyl, $R^2$, $R^3$, and $R^4$ are hydrogen atoms, Z is a hydrogen atom, $Y^1$, $Y^2$ and $Y^3$ are hydrogen atoms, $R^5$ is $C_1$-$C_6$ alkyl group, W is a group CO, and X is a chlorine atom or bromine atom. The compound of general formula (7') of the present invention is more preferably a compound wherein $R^1$ is a fluorine atom, chlorine atom, bromine atom, or methyl group, particularly preferably a methyl group, $R^2$, $R^3$, and $R^4$ are hydrogen atoms, Z is a hydrogen atom, $Y^1$, $Y^2$ and $Y^3$ are hydrogen atoms, $R^5$ is a methyl group, W is a group CO, and X is a bromine atom.

The representative compound of the compounds of general formula (7') can include 2-(1,3-dibromopropyl)-6-methylphenyl acetate.

Further, the compound of general formula (7") of the present invention is that described above, preferably a compound wherein $R^1$, $R^2$, $R^3$, and $R^4$ are hydrogen atoms, halogen atoms, or $C_1$-$C_6$ alkyl groups, Z is a hydrogen atom, $Y^1$, $Y^2$ and $Y^3$ are hydrogen atoms, X is a chlorine atom, bromine atom, or iodine atom, more preferably a compound wherein $R^1$ is a halogen atom or $C_1$-$C_6$ alkyl, $R^2$, $R^3$, and $R^4$ are hydrogen atoms, Z is a hydrogen atom, $Y^1$, $Y^2$ and $Y^3$ are hydrogen atoms, X is a chlorine atom or bromine atom. The compound of general formula (7") of the present invention is even preferably a compound wherein $R^1$ is a fluorine atom, chlorine atom, bromine atom, or methyl group, particularly preferably a methyl group, $R^2$, $R^3$, and $R^4$ are hydrogen atoms, Z is a hydrogen atom, $Y^1$, $Y^2$ and $Y^3$ are hydrogen atoms, and X is a bromine atom.

The representative compound of the compounds of general formula (7") can include 2-(1,3-dibromopropyl)-6-methylphenol.

Further, the compound of general formula (9') of the present invention is that described above, preferably a compound wherein $R^1$ is a halogen atom or $C_1$-$C_6$ alkyl group, $R^2$, $R^3$, and $R^4$ are hydrogen atoms, Z is a hydrogen atom, $Y^1$, $Y^2$ and $Y^3$ are hydrogen atoms, $R^5$ is a $C_1$-$C_6$ alkyl group, and W is a group CO. A compound of general formula (9') of the present invention is even preferably a compound wherein $R^1$ is a fluorine atom, chlorine atom, bromine atom, or a methyl group, particularly preferably a methyl group, $R^2$, $R^3$, and $R^4$ are hydrogen atoms, Z is a hydrogen atom, $Y^1$, $Y^2$ and $Y^3$ are hydrogen atoms, $R^5$ is a methyl group, and W is a group CO.

The representative compound of the compounds of general formula (9') can include 2-cyclopropyl-6-methylphenyl acetate.

Moreover, the compound of general formula (11') of the present invention is that described above, preferably a compound wherein $R^1$, $R^2$, $R^3$, and $R^4$ are hydrogen atoms, halogen atom, or a $C_1$-$C_6$ alkyl group, Z is a hydrogen atom, $Y^1$, $Y^2$ and $Y^3$ are hydrogen atoms, $R^5$ is a $C_1$-$C_6$ alkyl group, W is a group CO, and X is a chlorine atom, bromine atom, or iodine atom, provided that $R^1$ is neither a hydrogen atom nor acetoxy group, more preferably a compound wherein $R^1$ is a halogen atom or a $C_1$-$C_6$ alkyl group, $R^2$, $R^3$, and $R^4$ are hydrogen atoms, Z is a hydrogen atom, $Y^1$, $Y^2$ and $Y^3$ are hydrogen atoms, $R^5$ is a $C_1$-$C_6$ alkyl group, W is a group CO, and X is a chlorine atom or bromine atom.

The compound of general formula (11') of the present invention is even more preferably a compound wherein $R^1$ is a fluorine atom, chlorine atom, bromine atom, or methyl group, particularly preferably a methyl group, $R^2$, $R^3$, and $R^4$ are hydrogen atoms, Z is a hydrogen atom, $Y^1$, $Y^2$ and $Y^3$ are hydrogen atoms, $R^5$ is a methyl group, W is a group CO, and X is a bromine atom.

The representative compound of the compounds of general formula (11') can include 2-(3-bromo-1-propenyl)-6-methylphenyl acetate.

Moreover, the compound of general formula (11") of the present invention is that described above, preferably a compound wherein $R^1$, $R^2$, $R^3$, and $R^4$ represent hydrogen atoms, halogen atom, or $C_1$-$C_6$ alkyl group, Z is a hydrogen atom, $Y^1$, $Y^2$ and $Y^3$ are hydrogen atoms, X is a chlorine atom, bromine atom, or iodine atom, more preferably a compound wherein $R^1$ is a halogen atom or $C_1$-$C_6$ alkyl, $R^2$, $R^3$, and $R^4$ are hydrogen atoms, Z is a hydrogen atom, $Y^1$, $Y^2$ and $Y^3$ are hydrogen atoms, and X is a chlorine atom or bromine atom.

The compound of general formula (11") of the present invention is even more preferably a compound wherein $R^1$ is a fluorine atom, chlorine atom, bromine atom, or methyl group, particularly preferably a methyl group, $R^2$, $R^3$, and $R^4$ are hydrogen atoms, Z is a hydrogen atom, $Y^1$, $Y^2$ and $Y^3$ are hydrogen atoms, X is a bromine atom.

The representative compound of the compounds of general formula (11") can include 2-(3-bromo-1-propenyl)-6-methylphenol.

Although typical compounds of the present invention are listed in the following Table 1, the present invention is not limited to these compounds.

Although compounds used in the process of the present invention and compounds obtained according to the process of the present invention are listed in the following Table 1, the present invention is not limited thereto. In the table, "Me" indicates a methyl group, "Et" an ethyl group, "c-Pr" a cyclopropyl group, "i-Pr" an isopropyl group, and "Ph" a phenyl group.

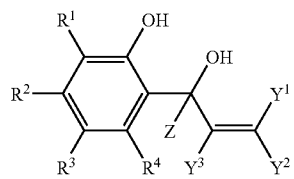

(3)

| Comp. No. | $R^1$ | $R^2$ | $R^3$ | $R^4$ | Z | $Y^1$ | $Y^2$ | $Y^3$ |
|---|---|---|---|---|---|---|---|---|
| 1-1 | H | H | H | H | H | H | H | H |
| 1-2 | Me | H | H | H | H | H | H | H |
| 1-3 | H | Me | H | H | H | H | H | H |
| 1-4 | H | H | Me | H | H | H | H | H |
| 1-5 | H | H | H | Me | H | H | H | H |
| 1-6 | H | H | H | H | Me | H | H | H |
| 1-7 | H | H | H | H | H | Me | H | H |
| 1-8 | H | H | H | H | H | H | Me | H |
| 1-9 | H | H | H | H | H | H | H | Me |
| 1-10 | Me | Me | H | H | H | H | H | H |
| 1-11 | Me | H | Me | H | H | H | H | H |
| 1-12 | Me | H | H | Me | H | H | H | H |
| 1-13 | Me | H | H | H | Me | H | H | H |
| 1-14 | Me | H | H | H | H | Me | H | H |
| 1-15 | Me | H | H | H | H | H | Me | H |
| 1-16 | Me | H | H | H | H | H | H | Me |
| 1-17 | Me | Me | Me | H | H | H | H | H |
| 1-18 | Me | Me | H | Me | H | H | H | H |
| 1-19 | Me | Me | H | H | Me | H | H | H |
| 1-20 | Me | Me | H | H | H | Me | H | H |
| 1-21 | Me | Me | H | H | H | H | Me | H |
| 1-22 | Me | Me | H | H | H | H | H | Me |
| 1-23 | Me | Me | H | Me | Me | H | H | H |
| 1-24 | Me | Me | H | Me | H | Me | H | H |
| 1-25 | Me | Me | H | Me | H | H | Me | H |
| 1-26 | Me | Me | H | Me | H | H | H | Me |
| 1-27 | Me | Me | Me | Me | H | H | H | H |
| 1-28 | Me | Me | Me | Me | Me | H | H | H |
| 1-29 | Me | Me | Me | Me | H | Me | H | H |
| 1-30 | Me | Me | Me | Me | H | H | Me | H |
| 1-31 | Me | Me | Me | Me | H | H | H | Me |
| 1-32 | H | Me | H | Me | H | H | H | H |
| 1-33 | H | H | Me | Me | H | H | H | H |
| 1-34 | Me | H | H | H | Me | Me | H | H |
| 1-35 | Me | H | H | H | Me | H | Me | H |
| 1-36 | Me | H | H | H | Me | H | H | Me |
| 1-37 | Me | H | H | H | Me | Me | Me | H |
| 1-38 | Me | H | H | H | Me | Me | H | Me |
| 1-39 | Me | H | H | H | Me | H | Me | Me |
| 1-40 | Me | H | H | H | Me | Me | Me | Me |
| 1-41 | Me | H | H | H | H | Me | Me | H |
| 1-42 | Me | H | H | H | H | Me | H | Me |
| 1-43 | Me | H | H | H | H | H | Me | Me |
| 1-44 | Me | H | H | H | H | Me | Me | Me |
| 1-45 | Me | H | H | H | Et | H | H | H |
| 1-46 | Me | H | H | H | cPr | H | H | H |
| 1-47 | Me | H | H | H | Ph | H | H | H |
| 1-48 | Me | H | H | H | H | Et | H | H |
| 1-49 | Et | H | H | H | H | H | H | H |
| 1-50 | H | Et | H | H | H | H | H | H |
| 1-51 | H | H | Et | H | H | H | H | H |
| 1-52 | H | H | H | Et | H | H | H | H |
| 1-53 | cPr | H | H | H | H | H | H | H |
| 1-54 | H | cPr | H | H | H | H | H | H |
| 1-55 | H | H | cPr | H | H | H | H | H |
| 1-56 | H | H | H | cPr | H | H | H | H |
| 1-57 | iPr | H | H | H | H | H | H | H |
| 1-58 | H | iPr | H | H | H | H | H | H |
| 1-59 | H | H | iPr | H | H | H | H | H |
| 1-60 | H | H | H | iPr | H | H | H | H |
| 1-61 | F | H | H | H | H | H | H | H |

-continued

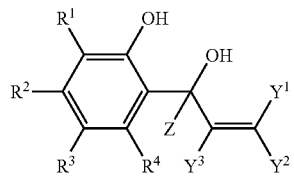

(3)

| Comp. No. | R¹ | R² | R³ | R⁴ | Z | Y¹ | Y² | Y³ |
|---|---|---|---|---|---|---|---|---|
| 1-62 | H | F | H | H | H | H | H | H |
| 1-63 | H | H | F | H | H | H | H | H |
| 1-64 | H | H | H | F | H | H | H | H |
| 1-65 | Cl | H | H | H | H | H | H | H |
| 1-66 | H | Cl | H | H | H | H | H | H |
| 1-67 | H | H | Cl | H | H | H | H | H |
| 1-68 | H | H | H | Cl | H | H | H | H |
| 1-69 | Br | H | H | H | H | H | H | H |
| 1-70 | H | Br | H | H | H | H | H | H |
| 1-71 | H | H | Br | H | H | H | H | H |
| 1-72 | H | H | H | Br | H | H | H | H |
| 1-73 | I | H | H | H | H | H | H | H |
| 1-74 | H | I | H | H | H | H | H | H |
| 1-75 | H | H | I | H | H | H | H | H |
| 1-76 | H | H | H | I | H | H | H | H |
| 1-77 | Me | F | H | H | H | H | H | H |
| 1-78 | Me | H | F | H | H | H | H | H |
| 1-79 | Me | H | H | F | H | H | H | H |
| 1-80 | Me | Cl | H | H | H | H | H | H |
| 1-81 | Me | H | Cl | H | H | H | H | H |
| 1-82 | Me | H | H | Cl | H | H | H | H |
| 1-83 | Me | Br | H | H | H | H | H | H |
| 1-84 | Me | H | Br | H | H | H | H | H |
| 1-85 | Me | H | H | Br | H | H | H | H |
| 1-86 | Et | Me | H | H | H | H | H | H |
| 1-87 | Et | H | Me | H | H | H | H | H |
| 1-88 | Et | H | H | Me | H | H | H | H |
| 1-89 | Et | F | H | H | H | H | H | H |
| 1-90 | Et | H | F | H | H | H | H | H |
| 1-91 | Et | H | H | F | H | H | H | H |
| 1-92 | Et | Cl | H | H | H | H | H | H |
| 1-93 | Et | H | Cl | H | H | H | H | H |
| 1-94 | Et | H | H | Cl | H | H | H | H |
| 1-95 | iPr | Me | H | H | H | H | H | H |
| 1-96 | iPr | H | Me | H | H | H | H | H |
| 1-97 | iPr | H | H | Me | H | H | H | H |
| 1-98 | iPr | F | H | H | H | H | H | H |
| 1-99 | iPr | H | F | H | H | H | H | H |
| 1-100 | iPr | H | H | F | H | H | H | H |
| 1-101 | iPr | Cl | H | H | H | H | H | H |
| 1-102 | iPr | H | Cl | H | H | H | H | H |
| 1-103 | iPr | H | H | Cl | H | H | H | H |
| 1-104 | cPr | Me | H | H | H | H | H | H |
| 1-105 | cPr | H | Me | H | H | H | H | H |
| 1-106 | cPr | H | H | Me | H | H | H | H |
| 1-107 | cPr | F | H | H | H | H | H | H |
| 1-108 | cPr | H | F | H | H | H | H | H |
| 1-109 | cPr | H | H | F | H | H | H | H |
| 1-110 | cPr | Cl | H | H | H | H | H | H |
| 1-111 | cPr | H | Cl | H | H | H | H | H |
| 1-112 | cPr | H | H | Cl | H | H | H | H |
| 1-113 | F | Me | H | H | H | H | H | H |
| 1-114 | F | H | Me | H | H | H | H | H |
| 1-115 | F | H | H | Me | H | H | H | H |
| 1-116 | F | F | H | H | H | H | H | H |
| 1-117 | F | H | F | H | H | H | H | H |
| 1-118 | F | H | H | F | H | H | H | H |
| 1-119 | F | Cl | H | H | H | H | H | H |
| 1-120 | F | H | Cl | H | H | H | H | H |
| 1-121 | F | H | H | Cl | H | H | H | H |
| 1-122 | Cl | Me | H | H | H | H | H | H |
| 1-123 | Cl | H | Me | H | H | H | H | H |
| 1-124 | Cl | H | H | Me | H | H | H | H |
| 1-125 | Cl | F | H | H | H | H | H | H |
| 1-126 | Cl | H | F | H | H | H | H | H |
| 1-127 | Cl | H | H | F | H | H | H | H |
| 1-128 | Cl | Cl | H | H | H | H | H | H |
| 1-129 | Cl | H | Cl | H | H | H | H | H |
| 1-130 | Cl | H | H | Cl | H | H | H | H |
| 1-131 | Br | Me | H | H | H | H | H | H |
| 1-132 | Br | H | Me | H | H | H | H | H |
| 1-133 | Br | H | H | Me | H | H | H | H |
| 1-134 | Br | F | H | H | H | H | H | H |
| 1-135 | Br | H | F | H | H | H | H | H |
| 1-136 | Br | H | H | F | H | H | H | H |
| 1-137 | Br | Cl | H | H | H | H | H | H |
| 1-138 | Br | H | Cl | H | H | H | H | H |
| 1-139 | Br | H | H | Cl | H | H | H | H |

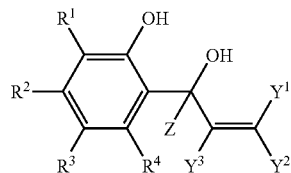

(7')

| Comp. No. | R¹ | R² | R³ | R⁴ | R⁵ | W | X | Z | Y¹ | Y² | Y³ |
|---|---|---|---|---|---|---|---|---|---|---|---|
| 2-1 | H | H | H | H | Me | CO | Cl | H | H | H | H |
| 2-2 | H | H | H | H | Me | CO | Br | H | H | H | H |
| 2-3 | H | H | H | H | Me | CO | I | H | H | H | H |
| 2-4 | Me | H | H | H | Me | CO | Cl | H | H | H | H |
| 2-5 | Me | H | H | H | Me | CO | Br | H | H | H | H |
| 2-6 | Me | H | H | H | Me | CO | I | H | H | H | H |
| 2-7 | H | Me | H | H | Me | CO | Cl | H | H | H | H |
| 2-8 | H | Me | H | H | Me | CO | Br | H | H | H | H |
| 2-9 | H | H | Me | H | Me | CO | Cl | H | H | H | H |
| 2-10 | H | H | Me | H | Me | CO | Br | H | H | H | H |
| 2-11 | H | H | H | Me | Me | CO | Cl | H | H | H | H |
| 2-12 | H | H | H | Me | Me | CO | Br | H | H | H | H |
| 2-13 | H | H | H | H | Me | CO | Br | Me | H | H | H |
| 2-14 | H | H | H | H | Me | CO | Br | H | Me | H | H |
| 2-15 | H | H | H | H | Me | CO | Br | H | H | Me | H |
| 2-16 | H | H | H | H | Me | CO | Br | H | H | H | Me |
| 2-17 | Me | Me | H | H | Me | CO | Cl | H | H | H | H |
| 2-18 | Me | Me | H | H | Me | CO | Br | H | H | H | H |
| 2-19 | Me | H | Me | H | Me | CO | Cl | H | H | H | H |
| 2-20 | Me | H | Me | H | Me | CO | Br | H | H | H | H |
| 2-21 | Me | H | H | Me | Me | CO | Cl | H | H | H | H |
| 2-22 | Me | H | H | Me | Me | CO | Br | H | H | H | H |
| 2-23 | Me | H | H | H | Me | CO | Br | Me | H | H | H |
| 2-24 | Me | H | H | H | Me | CO | Br | H | Me | H | H |
| 2-25 | Me | H | H | H | Me | CO | Br | H | H | Me | H |
| 2-26 | Me | H | H | H | Me | CO | Br | H | H | H | Me |
| 2-27 | Me | Me | Me | H | Me | CO | Br | H | H | H | H |
| 2-28 | Me | Me | H | Me | Me | CO | Br | H | H | H | H |
| 2-29 | Me | Me | H | H | Me | CO | Br | Me | H | H | H |
| 2-30 | Me | Me | H | H | Me | CO | Br | H | Me | H | H |
| 2-31 | Me | Me | H | H | Me | CO | Br | H | H | Me | H |

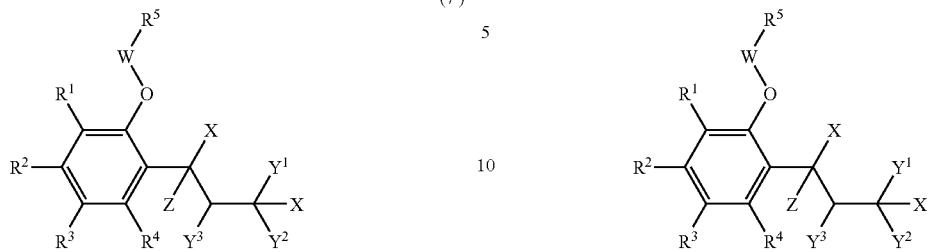

(7')

| Comp. No. | R¹ | R² | R³ | R⁴ | R⁵ | W | X | Z | Y¹ | Y² | Y³ |
|---|---|---|---|---|---|---|---|---|---|---|---|
| 2-32 | Me | Me | H | H | Me | CO | Br | H | H | H | Me |
| 2-33 | Me | Me | H | Me | Me | CO | Br | Me | H | H | H |
| 2-34 | Me | Me | H | Me | Me | CO | Br | H | Me | H | H |
| 2-35 | Me | Me | H | Me | Me | CO | Br | H | H | Me | H |
| 2-36 | Me | Me | H | Me | Me | CO | Br | H | H | H | Me |
| 2-37 | Me | Me | Me | Me | Me | CO | Cl | H | H | H | H |
| 2-38 | Me | Me | Me | Me | Me | CO | Br | H | H | H | H |
| 2-39 | Me | Me | Me | Me | Me | CO | Br | Me | H | H | H |
| 2-40 | Me | Me | Me | Me | Me | CO | Br | H | Me | H | H |
| 2-41 | Me | Me | Me | Me | Me | CO | Br | H | H | Me | H |
| 2-42 | Me | Me | Me | Me | Me | CO | Br | H | H | H | Me |
| 2-43 | H | Me | H | Me | Me | CO | Cl | H | H | H | H |
| 2-44 | H | Me | H | Me | Me | CO | Br | H | H | H | H |
| 2-45 | H | H | Me | Me | Me | CO | Br | H | H | H | H |
| 2-46 | Me | H | H | H | Me | CO | Br | Me | Me | H | H |
| 2-47 | Me | H | H | H | Me | CO | Br | Me | H | Me | H |
| 2-48 | Me | H | H | H | Me | CO | Br | Me | H | H | Me |
| 2-49 | Me | H | H | H | Me | CO | Br | Me | Me | Me | H |
| 2-50 | Me | H | H | H | Me | CO | Br | Me | Me | H | Me |
| 2-51 | Me | H | H | H | Me | CO | Br | Me | H | Me | Me |
| 2-52 | Me | H | H | H | Me | CO | Br | Me | Me | Me | Me |
| 2-53 | Me | H | H | H | Me | CO | Br | H | Me | Me | H |
| 2-54 | Me | H | H | H | Me | CO | Br | H | Me | H | Me |
| 2-55 | Me | H | H | H | Me | CO | Br | H | H | Me | Me |
| 2-56 | Me | H | H | H | Me | CO | Br | H | Me | Me | Me |
| 2-57 | Me | H | H | H | Me | CO | Br | Et | H | H | H |
| 2-58 | Me | H | H | H | Me | CO | Br | cPr | H | H | H |
| 2-59 | Me | H | H | H | Me | CO | Br | Ph | H | H | H |
| 2-60 | Me | H | H | H | Me | CO | Br | H | Et | H | H |
| 2-61 | Et | H | H | H | Me | CO | Cl | H | H | H | H |
| 2-62 | Et | H | H | H | Me | CO | Br | H | H | H | H |
| 2-63 | H | Et | H | H | Me | CO | Br | H | H | H | H |
| 2-64 | H | H | Et | H | Me | CO | Br | H | H | H | H |
| 2-65 | H | H | H | Et | Me | CO | Br | H | H | H | H |
| 2-66 | cPr | H | H | H | Me | CO | Cl | H | H | H | H |
| 2-67 | cPr | H | H | H | Me | CO | Br | H | H | H | H |
| 2-68 | H | cPr | H | H | Me | CO | Br | H | H | H | H |
| 2-69 | H | H | cPr | H | Me | CO | Br | H | H | H | H |
| 2-70 | H | H | H | cPr | Me | CO | Br | H | H | H | H |
| 2-71 | iPr | H | H | H | Me | CO | Cl | H | H | H | H |
| 2-72 | iPr | H | H | H | Me | CO | Br | H | H | H | H |
| 2-73 | H | iPr | H | H | Me | CO | Br | H | H | H | H |
| 2-74 | H | H | iPr | H | Me | CO | Br | H | H | H | H |
| 2-75 | H | H | H | iPr | Me | CO | Br | H | H | H | H |
| 2-76 | F | H | H | H | Me | CO | Cl | H | H | H | H |
| 2-77 | F | H | H | H | Me | CO | Br | H | H | H | H |
| 2-78 | H | F | H | H | Me | CO | Br | H | H | H | H |
| 2-79 | H | H | F | H | Me | CO | Br | H | H | H | H |
| 2-80 | H | H | H | F | Me | CO | Br | H | H | H | H |
| 2-81 | Cl | H | H | H | Me | CO | Cl | H | H | H | H |
| 2-82 | Cl | H | H | H | Me | CO | Br | H | H | H | H |
| 2-83 | H | Cl | H | H | Me | CO | Br | H | H | H | H |
| 2-84 | H | H | Cl | H | Me | CO | Br | H | H | H | H |
| 2-85 | H | H | H | Cl | Me | CO | Br | H | H | H | H |
| 2-86 | Br | H | H | H | Me | CO | Cl | H | H | H | H |
| 2-87 | Br | H | H | H | Me | CO | Br | H | H | H | H |
| 2-88 | H | Br | H | H | Me | CO | Br | H | H | H | H |
| 2-89 | H | H | Br | H | Me | CO | Br | H | H | H | H |
| 2-90 | H | H | H | Br | Me | CO | Br | H | H | H | H |
| 2-91 | I | H | H | H | Me | CO | Br | H | H | H | H |
| 2-92 | I | H | H | H | Me | CO | Br | H | H | H | H |
| 2-93 | H | I | H | H | Me | CO | Br | H | H | H | H |
| 2-94 | H | H | I | H | Me | CO | Br | H | H | H | H |
| 2-95 | H | H | H | I | Me | CO | Br | H | H | H | H |
| 2-96 | Me | F | H | H | Me | CO | Cl | H | H | H | H |
| 2-97 | Me | F | H | H | Me | CO | Br | H | H | H | H |
| 2-98 | Me | H | F | H | Me | CO | Br | H | H | H | H |
| 2-99 | Me | H | H | F | Me | CO | Br | H | H | H | H |
| 2-100 | Me | Cl | H | H | Me | CO | Cl | H | H | H | H |
| 2-101 | Me | Cl | H | H | Me | CO | Br | H | H | H | H |
| 2-102 | Me | H | Cl | H | Me | CO | Br | H | H | H | H |
| 2-103 | Me | H | H | Cl | Me | CO | Br | H | H | H | H |
| 2-104 | Me | Br | H | H | Me | CO | Cl | H | H | H | H |
| 2-105 | Me | Br | H | H | Me | CO | Br | H | H | H | H |
| 2-106 | Me | H | Br | H | Me | CO | Br | H | H | H | H |
| 2-107 | Me | H | H | Br | Me | CO | Br | H | H | H | H |
| 2-108 | Et | Me | H | H | Me | CO | Cl | H | H | H | H |
| 2-109 | Et | Me | H | H | Me | CO | Br | H | H | H | H |
| 2-110 | Et | H | Me | H | Me | CO | Br | H | H | H | H |
| 2-111 | Et | H | H | Me | Me | CO | Br | H | H | H | H |
| 2-112 | Et | F | H | H | Me | CO | Cl | H | H | H | H |
| 2-113 | Et | F | H | H | Me | CO | Br | H | H | H | H |
| 2-114 | Et | H | F | H | Me | CO | Br | H | H | H | H |
| 2-115 | Et | H | H | F | Me | CO | Br | H | H | H | H |
| 2-116 | Et | Cl | H | H | Me | CO | Cl | H | H | H | H |
| 2-117 | Et | Cl | H | H | Me | CO | Br | H | H | H | H |
| 2-118 | Et | H | Cl | H | Me | CO | Br | H | H | H | H |
| 2-119 | Et | H | H | Cl | Me | CO | Br | H | H | H | H |
| 2-120 | iPr | Me | H | H | Me | CO | Cl | H | H | H | H |
| 2-121 | iPr | Me | H | H | Me | CO | Br | H | H | H | H |
| 2-122 | iPr | H | Me | H | Me | CO | Br | H | H | H | H |
| 2-123 | iPr | H | H | Me | Me | CO | Br | H | H | H | H |
| 2-124 | iPr | F | H | H | Me | CO | Cl | H | H | H | H |
| 2-125 | iPr | F | H | H | Me | CO | Br | H | H | H | H |
| 2-126 | iPr | H | F | H | Me | CO | Br | H | H | H | H |
| 2-127 | iPr | H | H | F | Me | CO | Br | H | H | H | H |
| 2-128 | iPr | Cl | H | H | Me | CO | Cl | H | H | H | H |
| 2-129 | iPr | Cl | H | H | Me | CO | Br | H | H | H | H |
| 2-130 | iPr | H | Cl | H | Me | CO | Br | H | H | H | H |
| 2-131 | iPr | H | H | Cl | Me | CO | Br | H | H | H | H |
| 2-132 | cPr | Me | H | H | Me | CO | Cl | H | H | H | H |
| 2-133 | cPr | Me | H | H | Me | CO | Br | H | H | H | H |
| 2-134 | cPr | H | Me | H | Me | CO | Br | H | H | H | H |
| 2-135 | cPr | H | H | Me | Me | CO | Br | H | H | H | H |
| 2-136 | cPr | F | H | H | Me | CO | Cl | H | H | H | H |
| 2-137 | cPr | F | H | H | Me | CO | Br | H | H | H | H |
| 2-138 | cPr | H | F | H | Me | CO | Br | H | H | H | H |
| 2-139 | cPr | H | H | F | Me | CO | Br | H | H | H | H |
| 2-140 | cPr | Cl | H | H | Me | CO | Cl | H | H | H | H |
| 2-141 | cPr | Cl | H | H | Me | CO | Br | H | H | H | H |
| 2-142 | cPr | H | Cl | H | Me | CO | Br | H | H | H | H |
| 2-143 | cPr | H | H | Cl | Me | CO | Br | H | H | H | H |
| 2-144 | F | Me | H | H | Me | CO | Cl | H | H | H | H |
| 2-145 | F | Me | H | H | Me | CO | Br | H | H | H | H |
| 2-146 | F | H | Me | H | Me | CO | Br | H | H | H | H |
| 2-147 | F | H | H | Me | Me | CO | Br | H | H | H | H |
| 2-148 | F | F | H | H | Me | CO | Cl | H | H | H | H |
| 2-149 | F | F | H | H | Me | CO | Br | H | H | H | H |
| 2-150 | F | H | F | H | Me | CO | Br | H | H | H | H |
| 2-151 | F | H | H | F | Me | CO | Br | H | H | H | H |
| 2-152 | F | Cl | H | H | Me | CO | Cl | H | H | H | H |
| 2-153 | F | Cl | H | H | Me | CO | Br | H | H | H | H |
| 2-154 | F | H | Cl | H | Me | CO | Br | H | H | H | H |
| 2-155 | F | H | H | Cl | Me | CO | Br | H | H | H | H |

-continued (7')

| Comp. No. | R¹ | R² | R³ | R⁴ | R⁵ | W | X | Z | Y¹ | Y² | Y³ |
|---|---|---|---|---|---|---|---|---|---|---|---|
| 2-156 | Cl | Me | H | H | Me | CO | Cl | H | H | H | H |
| 2-157 | Cl | Me | H | H | Me | CO | Br | H | H | H | H |
| 2-158 | Cl | H | Me | H | Me | CO | Br | H | H | H | H |
| 2-159 | Cl | H | H | Me | Me | CO | Br | H | H | H | H |
| 2-160 | Cl | F | H | H | Me | CO | Cl | H | H | H | H |
| 2-161 | Cl | F | H | H | Me | CO | Br | H | H | H | H |
| 2-162 | Cl | H | F | H | Me | CO | Br | H | H | H | H |
| 2-163 | Cl | H | H | F | Me | CO | Br | H | H | H | H |
| 2-164 | Cl | Cl | H | H | Me | CO | Cl | H | H | H | H |
| 2-165 | Cl | Cl | H | H | Me | CO | Br | H | H | H | H |
| 2-166 | Cl | H | Cl | H | Me | CO | Br | H | H | H | H |
| 2-167 | Cl | H | H | Cl | Me | CO | Br | H | H | H | H |
| 2-168 | Br | Me | H | H | Me | CO | Cl | H | H | H | H |
| 2-169 | Br | Me | H | H | Me | CO | Br | H | H | H | H |
| 2-170 | Br | H | Me | H | Me | CO | Br | H | H | H | H |
| 2-171 | Br | H | H | Me | Me | CO | Br | H | H | H | H |
| 2-172 | Br | F | H | H | Me | CO | Cl | H | H | H | H |
| 2-173 | Br | F | H | H | Me | CO | Br | H | H | H | H |
| 2-174 | Br | H | F | H | Me | CO | Br | H | H | H | H |
| 2-175 | Br | H | H | F | Me | CO | Br | H | H | H | H |
| 2-176 | Br | Cl | H | H | Me | CO | Cl | H | H | H | H |
| 2-177 | Br | Cl | H | H | Me | CO | Br | H | H | H | H |
| 2-178 | Br | H | Cl | H | Me | CO | Br | H | H | H | H |
| 2-179 | Br | H | H | Cl | Me | CO | Br | H | H | H | H |
| 2-180 | Me | H | H | H | Et | CO | Br | H | H | H | H |
| 2-181 | Me | H | H | H | CH₂Cl | CO | Br | H | H | H | H |
| 2-182 | Me | H | H | H | CF₃ | CO | Br | H | H | H | H |
| 2-183 | Me | H | H | H | Bu-t | CO | Br | H | H | H | H |
| 2-184 | Me | H | H | H | OMe | CO | Br | H | H | H | H |
| 2-185 | Me | H | H | H | OEt | CO | Br | H | H | H | H |
| 2-186 | Me | H | H | H | Me | SO₂ | Br | H | H | H | H |
| 2-187 | Me | H | H | H | Ph | SO₂ | Br | H | H | H | H |

(7")

| Comp. No. | R¹ | R² | R³ | R⁴ | X | Z | Y¹ | Y² | Y³ |
|---|---|---|---|---|---|---|---|---|---|
| 3-1 | H | H | H | H | Cl | H | H | H | H |
| 3-2 | H | H | H | H | Br | H | H | H | H |
| 3-3 | H | H | H | H | I | H | H | H | H |
| 3-4 | Me | H | H | H | Cl | H | H | H | H |
| 3-5 | Me | H | H | H | Br | H | H | H | H |
| 3-6 | Me | H | H | H | I | H | H | H | H |
| 3-7 | H | Me | H | H | Cl | H | H | H | H |
| 3-8 | H | Me | H | H | Br | H | H | H | H |
| 3-9 | H | H | Me | H | Cl | H | H | H | H |
| 3-10 | H | H | Me | H | Br | H | H | H | H |
| 3-11 | H | H | H | Me | Cl | H | H | H | H |
| 3-12 | H | H | H | Me | Br | H | H | H | H |
| 3-13 | H | H | H | H | Br | Me | H | H | H |
| 3-14 | H | H | H | Br | H | Me | H | H | H |
| 3-15 | H | H | H | H | Br | H | H | Me | H |
| 3-16 | H | H | H | H | Br | H | H | H | Me |
| 3-17 | Me | Me | H | H | Cl | H | H | H | H |
| 3-18 | Me | Me | H | H | Br | H | H | H | H |
| 3-19 | Me | H | Me | H | Cl | H | H | H | H |
| 3-20 | Me | H | Me | H | Br | H | H | H | H |
| 3-21 | Me | H | H | Me | Cl | H | H | H | H |
| 3-22 | Me | H | H | Me | Br | H | H | H | H |
| 3-23 | Me | H | H | H | Br | Me | H | H | H |
| 3-24 | Me | H | H | H | Br | H | Me | H | H |
| 3-25 | Me | H | H | H | Br | H | H | Me | H |
| 3-26 | Me | H | H | H | Br | H | H | H | Me |
| 3-27 | Me | Me | Me | H | Br | H | H | H | H |
| 3-28 | Me | Me | H | Me | Br | H | H | H | H |
| 3-29 | Me | Me | H | H | Br | Me | H | H | H |
| 3-30 | Me | Me | H | H | Br | H | Me | H | H |
| 3-31 | Me | Me | H | H | Br | H | H | Me | H |
| 3-32 | Me | Me | H | H | Br | H | H | H | Me |
| 3-33 | Me | Me | H | Me | Br | Me | H | H | H |
| 3-34 | Me | Me | H | Me | Br | H | Me | H | H |
| 3-35 | Me | Me | H | Me | Br | H | H | Me | H |
| 3-36 | Me | Me | H | Me | Br | H | H | H | Me |
| 3-37 | Me | Me | Me | Me | Cl | H | H | H | H |
| 3-38 | Me | Me | Me | Me | Br | H | H | H | H |
| 3-39 | Me | Me | Me | Me | Br | Me | H | H | H |
| 3-40 | Me | Me | Me | Me | Br | H | Me | H | H |
| 3-41 | Me | Me | Me | Me | Br | H | H | Me | H |
| 3-42 | Me | Me | Me | Me | Br | H | H | H | Me |
| 3-43 | H | Me | H | Me | Cl | H | H | H | H |
| 3-44 | H | Me | H | Me | Br | H | H | H | H |
| 3-45 | H | H | Me | Me | Br | H | H | H | H |
| 3-46 | Me | H | H | H | Br | Me | Me | H | H |
| 3-47 | Me | H | H | H | Br | Me | H | Me | H |
| 3-48 | Me | H | H | H | Br | Me | H | H | Me |
| 3-49 | Me | H | H | H | Br | Me | Me | Me | H |
| 3-50 | Me | H | H | H | Br | Me | Me | H | Me |
| 3-51 | Me | H | H | H | Br | Me | H | Me | Me |
| 3-52 | Me | H | H | H | Br | Me | Me | Me | Me |
| 3-53 | Me | H | H | H | Br | H | Me | Me | H |
| 3-54 | Me | H | H | H | Br | H | Me | H | Me |
| 3-55 | Me | H | H | H | Br | H | H | Me | Me |
| 3-56 | Me | H | H | H | Br | H | Me | Me | Me |
| 3-57 | Me | H | H | H | Br | Et | H | H | H |
| 3-58 | Me | H | H | H | Br | cPr | H | H | H |
| 3-59 | Me | H | H | H | Br | Ph | H | H | H |
| 3-60 | Me | H | H | H | Br | H | Et | H | H |
| 3-61 | Et | H | H | H | Cl | H | H | H | H |
| 3-62 | Et | H | H | H | Br | H | H | H | H |
| 3-63 | H | Et | H | H | Br | H | H | H | H |
| 3-64 | H | H | Et | H | Br | H | H | H | H |
| 3-65 | H | H | H | Et | Br | H | H | H | H |
| 3-66 | cPr | H | H | H | Cl | H | H | H | H |
| 3-67 | cPr | H | H | H | Br | H | H | H | H |
| 3-68 | H | cPr | H | H | Br | H | H | H | H |
| 3-69 | H | H | cPr | H | Br | H | H | H | H |
| 3-70 | H | H | H | cPr | Br | H | H | H | H |
| 3-71 | iPr | H | H | H | Cl | H | H | H | H |
| 3-72 | iPr | H | H | H | Br | H | H | H | H |
| 3-73 | H | iPr | H | H | Br | H | H | H | H |
| 3-74 | H | H | iPr | H | Br | H | H | H | H |
| 3-75 | H | H | H | iPr | Br | H | H | H | H |
| 3-76 | F | H | H | H | Cl | H | H | H | H |
| 3-77 | F | H | H | H | Br | H | H | H | H |

-continued

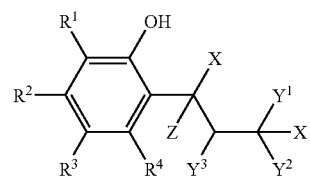

(7″)

| Comp. No. | R¹ | R² | R³ | R⁴ | X | Z | Y¹ | Y² | Y³ |
|---|---|---|---|---|---|---|---|---|---|
| 3-78 | H | F | H | H | Br | H | H | H | H |
| 3-79 | H | H | F | H | Br | H | H | H | H |
| 3-80 | H | H | H | F | Br | H | H | H | H |
| 3-81 | Cl | H | H | H | Cl | H | H | H | H |
| 3-82 | Cl | H | H | H | Br | H | H | H | H |
| 3-83 | H | Cl | H | H | Br | H | H | H | H |
| 3-84 | H | H | Cl | H | Br | H | H | H | H |
| 3-85 | H | H | H | Cl | Br | H | H | H | H |
| 3-86 | Br | H | H | H | Cl | H | H | H | H |
| 3-87 | Br | H | H | H | Br | H | H | H | H |
| 3-88 | H | Br | H | H | Br | H | H | H | H |
| 3-89 | H | H | Br | H | Br | H | H | H | H |
| 3-90 | H | H | H | Br | Br | H | H | H | H |
| 3-91 | I | H | H | H | Cl | H | H | H | H |
| 3-92 | I | H | H | H | Br | H | H | H | H |
| 3-93 | H | I | H | H | Br | H | H | H | H |
| 3-94 | H | H | I | H | Br | H | H | H | H |
| 3-95 | H | H | H | I | Br | H | H | H | H |
| 3-96 | Me | F | H | H | Cl | H | H | H | H |
| 3-97 | Me | F | H | H | Br | H | H | H | H |
| 3-98 | Me | H | F | H | Br | H | H | H | H |
| 3-99 | Me | H | H | F | Br | H | H | H | H |
| 3-100 | Me | Cl | H | H | Cl | H | H | H | H |
| 3-101 | Me | Cl | H | H | Br | H | H | H | H |
| 3-102 | Me | H | Cl | H | Br | H | H | H | H |
| 3-103 | Me | H | H | Cl | Br | H | H | H | H |
| 3-104 | Me | Br | H | H | Cl | H | H | H | H |
| 3-105 | Me | Br | H | H | Br | H | H | H | H |
| 3-106 | Me | H | Br | H | Br | H | H | H | H |
| 3-107 | Me | H | H | Br | Br | H | H | H | H |
| 3-108 | Et | Me | H | H | Cl | H | H | H | H |
| 3-109 | Et | Me | H | H | Br | H | H | H | H |
| 3-110 | Et | H | Me | H | Br | H | H | H | H |
| 3-111 | Et | H | H | Me | Br | H | H | H | H |
| 3-112 | Et | F | H | H | Cl | H | H | H | H |
| 3-113 | Et | F | H | H | Br | H | H | H | H |
| 3-114 | Et | H | F | H | Br | H | H | H | H |
| 3-115 | Et | H | H | F | Br | H | H | H | H |
| 3-116 | Et | Cl | H | H | Cl | H | H | H | H |
| 3-117 | Et | Cl | H | H | Br | H | H | H | H |
| 3-118 | Et | H | Cl | H | Br | H | H | H | H |
| 3-119 | Et | H | H | Cl | Br | H | H | H | H |
| 3-120 | iPr | Me | H | H | Cl | H | H | H | H |
| 3-121 | iPr | Me | H | H | Br | H | H | H | H |
| 3-122 | iPr | H | Me | H | Br | H | H | H | H |
| 3-123 | iPr | H | H | Me | Br | H | H | H | H |
| 3-124 | iPr | F | H | H | Cl | H | H | H | H |
| 3-125 | iPr | F | H | H | Br | H | H | H | H |
| 3-126 | iPr | H | F | H | Br | H | H | H | H |
| 3-127 | iPr | H | H | F | Br | H | H | H | H |
| 3-128 | iPr | Cl | H | H | Cl | H | H | H | H |
| 3-129 | iPr | Cl | H | H | Br | H | H | H | H |
| 3-130 | iPr | H | Cl | H | Br | H | H | H | H |
| 3-131 | iPr | H | H | Cl | Br | H | H | H | H |
| 3-132 | cPr | Me | H | H | Cl | H | H | H | H |
| 3-133 | cPr | Me | H | H | Br | H | H | H | H |
| 3-134 | cPr | H | Me | H | Br | H | H | H | H |
| 3-135 | cPr | H | H | Me | Br | H | H | H | H |
| 3-136 | cPr | F | H | H | Cl | H | H | H | H |
| 3-137 | cPr | F | H | H | Br | H | H | H | H |
| 3-138 | cPr | H | F | H | Br | H | H | H | H |
| 3-139 | cPr | H | H | F | Br | H | H | H | H |
| 3-140 | cPr | Cl | H | H | Cl | H | H | H | H |
| 3-141 | cPr | Cl | H | H | Br | H | H | H | H |
| 3-142 | cPr | H | Cl | H | Br | H | H | H | H |

-continued

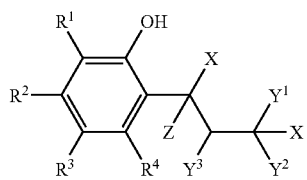

(7″)

| Comp. No. | R¹ | R² | R³ | R⁴ | X | Z | Y¹ | Y² | Y³ |
|---|---|---|---|---|---|---|---|---|---|
| 3-143 | cPr | H | H | Cl | Br | H | H | H | H |
| 3-144 | F | Me | H | H | Cl | H | H | H | H |
| 3-145 | F | Me | H | H | Br | H | H | H | H |
| 3-146 | F | H | Me | H | Br | H | H | H | H |
| 3-147 | F | H | H | Me | Br | H | H | H | H |
| 3-148 | F | F | H | H | Cl | H | H | H | H |
| 3-149 | F | F | H | H | Br | H | H | H | H |
| 3-150 | F | H | F | H | Br | H | H | H | H |
| 3-151 | F | H | H | F | Br | H | H | H | H |
| 3-152 | F | Cl | H | H | Cl | H | H | H | H |
| 3-153 | F | Cl | H | H | Br | H | H | H | H |
| 3-154 | F | H | Cl | H | Br | H | H | H | H |
| 3-155 | F | H | H | Cl | Br | H | H | H | H |
| 3-156 | Cl | Me | H | H | Cl | H | H | H | H |
| 3-157 | Cl | Me | H | H | Br | H | H | H | H |
| 3-158 | Cl | H | Me | H | Br | H | H | H | H |
| 3-159 | Cl | H | H | Me | Br | H | H | H | H |
| 3-160 | Cl | F | H | H | Cl | H | H | H | H |
| 3-161 | Cl | F | H | H | Br | H | H | H | H |
| 3-162 | Cl | H | F | H | Br | H | H | H | H |
| 3-163 | Cl | H | H | F | Br | H | H | H | H |
| 3-164 | Cl | Cl | H | H | Cl | H | H | H | H |
| 3-165 | Cl | Cl | H | H | Br | H | H | H | H |
| 3-166 | Cl | H | Cl | H | Br | H | H | H | H |
| 3-167 | Cl | H | H | Cl | Br | H | H | H | H |
| 3-168 | Br | Me | H | H | Cl | H | H | H | H |
| 3-169 | Br | Me | H | H | Br | H | H | H | H |
| 3-170 | Br | H | Me | H | Br | H | H | H | H |
| 3-171 | Br | H | H | Me | Br | H | H | H | H |
| 3-172 | Br | F | H | H | Cl | H | H | H | H |
| 3-173 | Br | F | H | H | Br | H | H | H | H |
| 3-174 | Br | H | F | H | Br | H | H | H | H |
| 3-175 | Br | H | H | F | Br | H | H | H | H |
| 3-176 | Br | Cl | H | H | Cl | H | H | H | H |
| 3-177 | Br | Cl | H | H | Br | H | H | H | H |
| 3-178 | Br | H | Cl | H | Br | H | H | H | H |
| 3-179 | Br | H | H | Cl | Br | H | H | H | H |

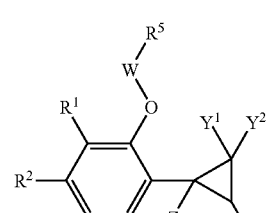

(9′)

| Comp. No. | R¹ | R² | R³ | R⁴ | R⁵ | W | Z | Y¹ | Y² | Y³ |
|---|---|---|---|---|---|---|---|---|---|---|
| 4-1 | H | H | H | H | Me | CO | H | H | H | H |
| 4-2 | Me | H | H | H | Me | CO | H | H | H | H |
| 4-3 | H | Me | H | H | Me | CO | H | H | H | H |
| 4-4 | H | H | Me | H | Me | CO | H | H | H | H |
| 4-5 | H | H | H | Me | Me | CO | H | H | H | H |
| 4-6 | H | H | H | H | Me | CO | Me | H | H | H |
| 4-7 | H | H | H | H | Me | CO | H | Me | H | H |

-continued (9')

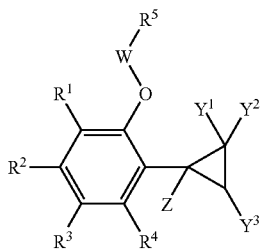

| Comp. No. | R¹ | R² | R³ | R⁴ | R⁵ | W | Z | Y¹ | Y² | Y³ |
|---|---|---|---|---|---|---|---|---|---|---|
| 4-8 | H | H | H | H | Me | CO | H | H | Me | H |
| 4-9 | H | H | H | H | Me | CO | H | H | H | Me |
| 4-10 | Me | Me | H | H | Me | CO | H | H | H | H |
| 4-11 | Me | H | Me | H | Me | CO | H | H | H | H |
| 4-12 | Me | H | H | Me | Me | CO | H | H | H | H |
| 4-13 | Me | H | H | H | Me | CO | Me | H | H | H |
| 4-14 | Me | H | H | H | Me | CO | H | Me | H | H |
| 4-15 | Me | H | H | H | Me | CO | H | H | Me | H |
| 4-16 | Me | H | H | H | Me | CO | H | H | H | Me |
| 4-17 | Me | Me | Me | H | Me | CO | H | H | H | H |
| 4-18 | Me | Me | H | Me | Me | CO | H | H | H | H |
| 4-19 | Me | Me | H | H | Me | CO | Me | H | H | H |
| 4-20 | Me | Me | H | H | Me | CO | H | Me | H | H |
| 4-21 | Me | Me | H | H | Me | CO | H | H | Me | H |
| 4-22 | Me | Me | H | H | Me | CO | H | H | H | Me |
| 4-23 | Me | Me | H | Me | Me | CO | Me | H | H | H |
| 4-24 | Me | Me | H | Me | Me | CO | H | Me | H | H |
| 4-25 | Me | Me | H | Me | Me | CO | H | H | Me | H |
| 4-26 | Me | Me | H | Me | Me | CO | H | H | H | Me |
| 4-27 | Me | Me | Me | Me | Me | CO | H | H | H | H |
| 4-28 | Me | Me | Me | Me | Me | CO | Me | H | H | H |
| 4-29 | Me | Me | Me | Me | Me | CO | H | Me | H | H |
| 4-30 | Me | Me | Me | Me | Me | CO | H | H | Me | H |
| 4-31 | Me | Me | Me | Me | Me | CO | H | H | H | Me |
| 4-32 | H | Me | H | Me | Me | CO | H | H | H | H |
| 4-33 | H | H | Me | Me | Me | CO | H | H | H | H |
| 4-34 | Me | H | H | H | Me | CO | Me | Me | H | H |
| 4-35 | Me | H | H | H | Me | CO | Me | H | Me | H |
| 4-36 | Me | H | H | H | Me | CO | Me | H | H | Me |
| 4-37 | Me | H | H | H | Me | CO | Me | Me | Me | H |
| 4-38 | Me | H | H | H | Me | CO | Me | Me | H | Me |
| 4-39 | Me | H | H | H | Me | CO | Me | H | Me | Me |
| 4-40 | Me | H | H | H | Me | CO | Me | Me | Me | Me |
| 4-41 | Me | H | H | H | Me | CO | H | Me | Me | H |
| 4-42 | Me | H | H | H | Me | CO | H | Me | H | Me |
| 4-43 | Me | H | H | H | Me | CO | H | H | Me | Me |
| 4-44 | Me | H | H | H | Me | CO | H | Me | Me | Me |
| 4-45 | Me | H | H | H | Me | CO | Et | H | H | H |
| 4-46 | Me | H | H | H | Me | CO | cPr | H | H | H |
| 4-47 | Me | H | H | H | Me | CO | Ph | H | H | H |
| 4-48 | Me | H | H | H | Me | CO | H | Et | H | H |
| 4-49 | Et | H | H | H | Me | CO | H | H | H | H |
| 4-50 | H | Et | H | H | Me | CO | H | H | H | H |
| 4-51 | H | H | Et | H | Me | CO | H | H | H | H |
| 4-52 | H | H | H | Et | Me | CO | H | H | H | H |
| 4-53 | cPr | H | H | H | Me | CO | H | H | H | H |
| 4-54 | H | cPr | H | H | Me | CO | H | H | H | H |
| 4-55 | H | H | cPr | H | Me | CO | H | H | H | H |
| 4-56 | H | H | H | cPr | Me | CO | H | H | H | H |
| 4-57 | iPr | H | H | H | Me | CO | H | H | H | H |
| 4-58 | H | iPr | H | H | Me | CO | H | H | H | H |
| 4-59 | H | H | iPr | H | Me | CO | H | H | H | H |
| 4-60 | H | H | H | iPr | Me | CO | H | H | H | H |
| 4-61 | F | H | H | H | Me | CO | H | H | H | H |
| 4-62 | H | F | H | H | Me | CO | H | H | H | H |
| 4-63 | H | H | F | H | Me | CO | H | H | H | H |
| 4-64 | H | H | H | F | Me | CO | H | H | H | H |
| 4-65 | Cl | H | H | H | Me | CO | H | H | H | H |
| 4-66 | H | Cl | H | H | Me | CO | H | H | H | H |
| 4-67 | H | H | Cl | H | Me | CO | H | H | H | H |
| 4-68 | H | H | H | Cl | Me | CO | H | H | H | H |
| 4-69 | Br | H | H | H | Me | CO | H | H | H | H |
| 4-70 | H | Br | H | H | Me | CO | H | H | H | H |
| 4-71 | H | H | Br | H | Me | CO | H | H | H | H |
| 4-72 | H | H | H | Br | Me | CO | H | H | H | H |
| 4-73 | I | H | H | H | Me | CO | H | H | H | H |
| 4-74 | H | I | H | H | Me | CO | H | H | H | H |
| 4-75 | H | H | I | H | Me | CO | H | H | H | H |
| 4-76 | H | H | H | I | Me | CO | H | H | H | H |
| 4-77 | Me | F | H | H | Me | CO | H | H | H | H |
| 4-78 | Me | H | F | H | Me | CO | H | H | H | H |
| 4-79 | Me | H | H | F | Me | CO | H | H | H | H |
| 4-80 | Me | Cl | H | H | Me | CO | H | H | H | H |
| 4-81 | Me | H | Cl | H | Me | CO | H | H | H | H |
| 4-82 | Me | H | H | Cl | Me | CO | H | H | H | H |
| 4-83 | Me | Br | H | H | Me | CO | H | H | H | H |
| 4-84 | Me | H | Br | H | Me | CO | H | H | H | H |
| 4-85 | Me | H | H | Br | Me | CO | H | H | H | H |
| 4-86 | Et | Me | H | H | Me | CO | H | H | H | H |
| 4-87 | Et | H | Me | H | Me | CO | H | H | H | H |
| 4-88 | Et | H | H | Me | Me | CO | H | H | H | H |
| 4-89 | Et | F | H | H | Me | CO | H | H | H | H |
| 4-90 | Et | H | F | H | Me | CO | H | H | H | H |
| 4-91 | Et | H | H | F | Me | CO | H | H | H | H |
| 4-92 | Et | Cl | H | H | Me | CO | H | H | H | H |
| 4-93 | Et | H | Cl | H | Me | CO | H | H | H | H |
| 4-94 | Et | H | H | Cl | Me | CO | H | H | H | H |
| 4-95 | iPr | Me | H | H | Me | CO | H | H | H | H |
| 4-96 | iPr | H | Me | H | Me | CO | H | H | H | H |
| 4-97 | iPr | H | H | Me | Me | CO | H | H | H | H |
| 4-98 | iPr | F | H | H | Me | CO | H | H | H | H |
| 4-99 | iPr | H | F | H | Me | CO | H | H | H | H |
| 4-100 | iPr | H | H | F | Me | CO | H | H | H | H |
| 4-101 | iPr | Cl | H | H | Me | CO | H | H | H | H |
| 4-102 | iPr | H | Cl | H | Me | CO | H | H | H | H |
| 4-103 | iPr | H | H | Cl | Me | CO | H | H | H | H |
| 4-104 | cPr | Me | H | H | Me | CO | H | H | H | H |
| 4-105 | cPr | H | Me | H | Me | CO | H | H | H | H |
| 4-106 | cPr | H | H | Me | Me | CO | H | H | H | H |
| 4-107 | cPr | F | H | H | Me | CO | H | H | H | H |
| 4-108 | cPr | H | F | H | Me | CO | H | H | H | H |
| 4-109 | cPr | H | H | F | Me | CO | H | H | H | H |
| 4-110 | cPr | Cl | H | H | Me | CO | H | H | H | H |
| 4-111 | cPr | H | Cl | H | Me | CO | H | H | H | H |
| 4-112 | cPr | H | H | Cl | Me | CO | H | H | H | H |
| 4-113 | F | Me | H | H | Me | CO | H | H | H | H |
| 4-114 | F | H | Me | H | Me | CO | H | H | H | H |
| 4-115 | F | H | H | Me | Me | CO | H | H | H | H |
| 4-116 | F | F | H | H | Me | CO | H | H | H | H |
| 4-117 | F | H | F | H | Me | CO | H | H | H | H |
| 4-118 | F | H | H | F | Me | CO | H | H | H | H |
| 4-119 | F | Cl | H | H | Me | CO | H | H | H | H |
| 4-120 | F | H | Cl | H | Me | CO | H | H | H | H |
| 4-121 | F | H | H | Cl | Me | CO | H | H | H | H |
| 4-122 | Cl | Me | H | H | Me | CO | H | H | H | H |
| 4-123 | Cl | H | Me | H | Me | CO | H | H | H | H |
| 4-124 | Cl | H | H | Me | Me | CO | H | H | H | H |
| 4-125 | Cl | F | H | H | Me | CO | H | H | H | H |
| 4-126 | Cl | H | F | H | Me | CO | H | H | H | H |
| 4-127 | Cl | H | H | F | Me | CO | H | H | H | H |
| 4-128 | Cl | Cl | H | H | Me | CO | H | H | H | H |
| 4-129 | Cl | H | Cl | H | Me | CO | H | H | H | H |
| 4-130 | Cl | H | H | Cl | Me | CO | H | H | H | H |
| 4-131 | Br | Me | H | H | Me | CO | H | H | H | H |

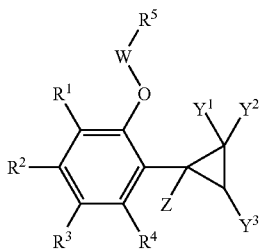

-continued (9')

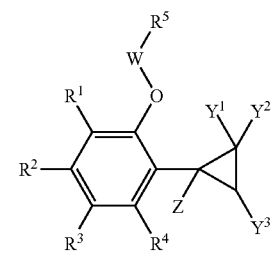

| Comp. No. | R¹ | R² | R³ | R⁴ | R⁵ | W | Z | Y¹ | Y² | Y³ |
|---|---|---|---|---|---|---|---|---|---|---|
| 4-132 | Br | H | Me | H | Me | CO | H | H | H | H |
| 4-133 | Br | H | H | Me | Me | CO | H | H | H | H |
| 4-134 | Br | F | H | H | Me | CO | H | H | H | H |
| 4-135 | Br | H | F | H | Me | CO | H | H | H | H |
| 4-136 | Br | H | H | F | Me | CO | H | H | H | H |
| 4-137 | Br | Cl | H | H | Me | CO | H | H | H | H |
| 4-138 | Br | H | Cl | H | Me | CO | H | H | H | H |
| 4-139 | Br | H | H | Cl | Me | CO | H | H | H | H |
| 4-140 | Me | H | H | H | Et | CO | H | H | H | H |
| 4-141 | Me | H | H | H | CH₂Cl | CO | H | H | H | H |
| 4-142 | Me | H | H | H | CF₃ | CO | H | H | H | H |
| 4-143 | Me | H | H | H | Bu-t | CO | H | H | H | H |
| 4-144 | Me | H | H | H | OMe | CO | H | H | H | H |
| 4-145 | Me | H | H | H | OEt | CO | H | H | H | H |
| 4-146 | Me | H | H | H | Me | SO₂ | H | H | H | H |
| 4-147 | Me | H | H | H | Ph | SO₂ | H | H | H | H |

(10)

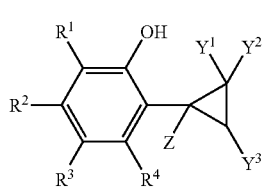

| Comp. No. | R¹ | R² | R³ | R⁴ | Z | Y¹ | Y² | Y³ |
|---|---|---|---|---|---|---|---|---|
| 5-1 | H | H | H | H | H | H | H | H |
| 5-2 | Me | H | H | H | H | H | H | H |
| 5-3 | H | Me | H | H | H | H | H | H |
| 5-4 | H | H | Me | H | H | H | H | H |
| 5-5 | H | H | H | Me | H | H | H | H |
| 5-6 | H | H | H | H | Me | H | H | H |
| 5-7 | H | H | H | H | H | Me | H | H |
| 5-8 | H | H | H | H | H | H | Me | H |
| 5-9 | H | H | H | H | H | H | H | Me |
| 5-10 | Me | Me | H | H | H | H | H | H |
| 5-11 | Me | H | Me | H | H | H | H | H |
| 5-12 | Me | H | H | Me | H | H | H | H |
| 5-13 | Me | H | H | H | Me | H | H | H |
| 5-14 | Me | H | H | H | H | Me | H | H |
| 5-15 | Me | H | H | H | H | H | Me | H |
| 5-16 | Me | H | H | H | H | H | H | Me |
| 5-17 | Me | Me | Me | H | H | H | H | H |
| 5-18 | Me | Me | H | Me | H | H | H | H |
| 5-19 | Me | Me | H | H | Me | H | H | H |
| 5-20 | Me | Me | H | H | H | Me | H | H |
| 5-21 | Me | Me | H | H | H | H | Me | H |
| 5-22 | Me | Me | H | H | H | H | H | Me |
| 5-23 | Me | Me | Me | Me | H | H | H | H |
| 5-24 | Me | Me | H | Me | Me | H | H | H |
| 5-25 | Me | Me | H | Me | H | Me | H | H |
| 5-26 | Me | Me | H | Me | H | H | H | Me |
| 5-27 | Me | Me | Me | H | Me | H | H | H |
| 5-28 | Me | Me | Me | Me | H | H | H | H |
| 5-29 | Me | Me | Me | Me | H | Me | H | H |
| 5-30 | Me | Me | Me | Me | H | H | Me | H |
| 5-31 | Me | Me | Me | Me | H | H | H | Me |
| 5-32 | H | Me | H | Me | H | H | H | H |
| 5-33 | H | H | Me | Me | H | H | H | H |
| 5-34 | Me | H | H | H | Me | Me | H | H |
| 5-35 | Me | H | H | H | Me | H | Me | H |
| 5-36 | Me | H | H | H | Me | H | H | Me |
| 5-37 | Me | H | H | H | Me | Me | Me | H |
| 5-38 | Me | H | H | H | Me | Me | H | Me |
| 5-39 | Me | H | H | H | Me | H | Me | Me |
| 5-40 | Me | H | H | H | Me | Me | Me | Me |
| 5-41 | Me | H | H | H | H | Me | Me | H |
| 5-42 | Me | H | H | H | H | Me | H | Me |
| 5-43 | Me | H | H | H | H | H | Me | Me |
| 5-44 | Me | H | H | H | H | Me | Me | Me |
| 5-45 | Me | H | H | H | Et | H | H | H |
| 5-46 | Me | H | H | H | cPr | H | H | H |
| 5-47 | Me | H | H | H | Ph | H | H | H |
| 5-48 | Me | H | H | H | H | Et | H | H |
| 5-49 | Et | H | H | H | H | H | H | H |
| 5-50 | H | Et | H | H | H | H | H | H |
| 5-51 | H | H | Et | H | H | H | H | H |
| 5-52 | H | H | H | Et | H | H | H | H |
| 5-53 | cPr | H | H | H | H | H | H | H |
| 5-54 | H | cPr | H | H | H | H | H | H |
| 5-55 | H | H | cPr | H | H | H | H | H |
| 5-56 | H | H | H | cPr | H | H | H | H |
| 5-57 | iPr | H | H | H | H | H | H | H |
| 5-58 | H | iPr | H | H | H | H | H | H |
| 5-59 | H | H | iPr | H | H | H | H | H |
| 5-60 | H | H | H | iPr | H | H | H | H |
| 5-61 | F | H | H | H | H | H | H | H |
| 5-62 | H | F | H | H | H | H | H | H |
| 5-63 | H | H | F | H | H | H | H | H |
| 5-64 | H | H | H | F | H | H | H | H |
| 5-65 | Cl | H | H | H | H | H | H | H |
| 5-66 | H | Cl | H | H | H | H | H | H |
| 5-67 | H | H | Cl | H | H | H | H | H |
| 5-68 | H | H | H | Cl | H | H | H | H |
| 5-69 | Br | H | H | H | H | H | H | H |
| 5-70 | H | Br | H | H | H | H | H | H |
| 5-71 | H | H | Br | H | H | H | H | H |
| 5-72 | H | H | H | Br | H | H | H | H |
| 5-73 | I | H | H | H | H | H | H | H |
| 5-74 | H | I | H | H | H | H | H | H |
| 5-75 | H | H | I | H | H | H | H | H |
| 5-76 | H | H | H | I | H | H | H | H |
| 5-77 | Me | F | H | H | H | H | H | H |
| 5-78 | Me | H | F | H | H | H | H | H |
| 5-79 | Me | H | H | F | H | H | H | H |
| 5-80 | Me | Cl | H | H | H | H | H | H |
| 5-81 | Me | H | Cl | H | H | H | H | H |
| 5-82 | Me | H | H | Cl | H | H | H | H |
| 5-83 | Me | Br | H | H | H | H | H | H |
| 5-84 | Me | H | Br | H | H | H | H | H |
| 5-85 | Me | H | H | Br | H | H | H | H |
| 5-86 | Et | Me | H | H | H | H | H | H |
| 5-87 | Et | H | Me | H | H | H | H | H |
| 5-88 | Et | H | H | Me | H | H | H | H |
| 5-89 | Et | F | H | H | H | H | H | H |
| 5-90 | Et | H | F | H | H | H | H | H |
| 5-91 | Et | H | H | F | H | H | H | H |
| 5-92 | Et | Cl | H | H | H | H | H | H |
| 5-93 | Et | H | Cl | H | H | H | H | H |
| 5-94 | Et | H | H | Cl | H | H | H | H |

(10)

Structure: Phenol with R¹, R², R³, R⁴ substituents on the ring, OH, and a cyclopropane group bearing Z, Y¹, Y², Y³.

| Comp. No. | R¹ | R² | R³ | R⁴ | Z | Y¹ | Y² | Y³ |
|---|---|---|---|---|---|---|---|---|
| 5-95 | iPr | Me | H | H | H | H | H | H |
| 5-96 | iPr | H | Me | H | H | H | H | H |
| 5-97 | iPr | H | H | Me | H | H | H | H |
| 5-98 | iPr | F | H | H | H | H | H | H |
| 5-99 | iPr | H | F | H | H | H | H | H |
| 5-100 | iPr | H | H | F | H | H | H | H |
| 5-101 | iPr | Cl | H | H | H | H | H | H |
| 5-102 | iPr | H | Cl | H | H | H | H | H |
| 5-103 | iPr | H | H | Cl | H | H | H | H |
| 5-104 | cPr | Me | H | H | H | H | H | H |
| 5-105 | cPr | H | Me | H | H | H | H | H |
| 5-106 | cPr | H | H | Me | H | H | H | H |
| 5-107 | cPr | F | H | H | H | H | H | H |
| 5-108 | cPr | H | F | H | H | H | H | H |
| 5-109 | cPr | H | H | F | H | H | H | H |
| 5-110 | cPr | Cl | H | H | H | H | H | H |
| 5-111 | cPr | H | Cl | H | H | H | H | H |
| 5-112 | cPr | H | H | Cl | H | H | H | H |
| 5-113 | F | Me | H | H | H | H | H | H |
| 5-114 | F | H | Me | H | H | H | H | H |
| 5-115 | F | H | H | Me | H | H | H | H |
| 5-116 | F | F | H | H | H | H | H | H |
| 5-117 | F | H | F | H | H | H | H | H |
| 5-118 | F | H | H | F | H | H | H | H |
| 5-119 | F | Cl | H | H | H | H | H | H |
| 5-120 | F | H | Cl | H | H | H | H | H |
| 5-121 | F | H | H | Cl | H | H | H | H |
| 5-122 | Cl | Me | H | H | H | H | H | H |
| 5-123 | Cl | H | Me | H | H | H | H | H |
| 5-124 | Cl | H | H | Me | H | H | H | H |
| 5-125 | Cl | F | H | H | H | H | H | H |
| 5-126 | Cl | H | F | H | H | H | H | H |
| 5-127 | Cl | H | H | F | H | H | H | H |
| 5-128 | Cl | Cl | H | H | H | H | H | H |
| 5-129 | Cl | H | Cl | H | H | H | H | H |
| 5-130 | Cl | H | H | Cl | H | H | H | H |
| 5-131 | Br | Me | H | H | H | H | H | H |
| 5-132 | Br | H | Me | H | H | H | H | H |
| 5-133 | Br | H | H | Me | H | H | H | H |
| 5-134 | Br | F | H | H | H | H | H | H |
| 5-135 | Br | H | F | H | H | H | H | H |
| 5-136 | Br | H | H | F | H | H | H | H |
| 5-137 | Br | Cl | H | H | H | H | H | H |
| 5-138 | Br | H | Cl | H | H | H | H | H |
| 5-139 | Br | H | H | Cl | H | H | H | H |

(11')

Structure: Aryl (R¹–R⁴) with O-W-R⁵ group, and a vinyl chain bearing Z, Y¹, Y², Y³, X.

| Comp. No. | R¹ | R² | R³ | R⁴ | R⁵ | W | X | Z | Y¹ | Y² | Y³ |
|---|---|---|---|---|---|---|---|---|---|---|---|
| 6-1 | H | H | H | H | Me | CO | Cl | H | H | H | H |
| 6-2 | H | H | H | H | Me | CO | Br | H | H | H | H |
| 6-3 | H | H | H | H | Me | CO | I | H | H | H | H |
| 6-4 | Me | H | H | H | Me | CO | Cl | H | H | H | H |
| 6-5 | Me | H | H | H | Me | CO | Br | H | H | H | H |
| 6-6 | Me | H | H | H | Me | CO | I | H | H | H | H |
| 6-7 | H | Me | H | H | Me | CO | Cl | H | H | H | H |
| 6-8 | H | Me | H | H | Me | CO | Br | H | H | H | H |
| 6-9 | H | H | Me | H | Me | CO | Cl | H | H | H | H |
| 6-10 | H | H | Me | H | Me | CO | Br | H | H | H | H |
| 6-11 | H | H | H | Me | Me | CO | Cl | H | H | H | H |
| 6-12 | H | H | H | Me | Me | CO | Br | H | H | H | H |
| 6-13 | H | H | H | H | Me | CO | Br | Me | H | H | H |
| 6-14 | H | H | H | H | Me | CO | Br | H | Me | H | H |
| 6-15 | H | H | H | H | Me | CO | Br | H | H | Me | H |
| 6-16 | H | H | H | H | Me | CO | Br | H | H | H | Me |
| 6-17 | Me | Me | H | H | Me | CO | Cl | H | H | H | H |
| 6-18 | Me | Me | H | H | Me | CO | Br | H | H | H | H |
| 6-19 | Me | H | Me | H | Me | CO | Cl | H | H | H | H |
| 6-20 | Me | H | Me | H | Me | CO | Br | H | H | H | H |
| 6-21 | Me | H | H | Me | Me | CO | Cl | H | H | H | H |
| 6-22 | Me | H | H | Me | Me | CO | Br | H | H | H | H |
| 6-23 | Me | H | H | H | Me | CO | Br | Me | H | H | H |
| 6-24 | Me | H | H | H | Me | CO | Br | H | Me | H | H |
| 6-25 | Me | H | H | H | Me | CO | Br | H | H | Me | H |
| 6-26 | Me | H | H | H | Me | CO | Br | H | H | H | Me |
| 6-27 | Me | Me | Me | H | Me | CO | Br | H | H | H | H |
| 6-28 | Me | Me | H | Me | Me | CO | Br | H | H | H | H |
| 6-29 | Me | Me | H | H | Me | CO | Br | Me | H | H | H |
| 6-30 | Me | Me | H | H | Me | CO | Br | H | Me | H | H |
| 6-31 | Me | Me | H | H | Me | CO | Br | H | H | Me | H |
| 6-32 | Me | Me | H | H | Me | CO | Br | H | H | H | Me |
| 6-33 | Me | Me | H | Me | Me | CO | Br | Me | H | H | H |
| 6-34 | Me | Me | H | Me | Me | CO | Br | H | Me | H | H |
| 6-35 | Me | Me | H | Me | Me | CO | Br | H | H | Me | H |
| 6-36 | Me | Me | H | Me | Me | CO | Br | H | H | H | Me |
| 6-37 | Me | Me | Me | Me | Me | CO | Cl | H | H | H | H |
| 6-38 | Me | Me | Me | Me | Me | CO | Br | H | H | H | H |
| 6-39 | Me | Me | Me | Me | Me | CO | Br | Me | H | H | H |
| 6-40 | Me | Me | Me | Me | Me | CO | Br | H | Me | H | H |
| 6-41 | Me | Me | Me | Me | Me | CO | Br | H | H | Me | H |
| 6-42 | Me | Me | Me | Me | Me | CO | Br | H | H | H | Me |
| 6-43 | H | Me | H | Me | Me | CO | Cl | H | H | H | H |
| 6-44 | H | Me | H | Me | Me | CO | Br | H | H | H | H |
| 6-45 | H | H | Me | Me | Me | CO | Br | H | H | H | H |
| 6-46 | Me | H | H | H | Me | CO | Br | Me | Me | H | H |
| 6-47 | Me | H | H | H | Me | CO | Br | Me | H | Me | H |
| 6-48 | Me | H | H | H | Me | CO | Br | Me | H | H | Me |
| 6-49 | Me | H | H | H | Me | CO | Br | Me | Me | Me | H |
| 6-50 | Me | H | H | H | Me | CO | Br | Me | Me | H | Me |
| 6-51 | Me | H | H | H | Me | CO | Br | Me | H | Me | Me |
| 6-52 | Me | H | H | H | Me | CO | Br | Me | Me | Me | Me |
| 6-53 | Me | H | H | H | Me | CO | Br | H | Me | Me | H |
| 6-54 | Me | H | H | H | Me | CO | Br | H | Me | H | Me |
| 6-55 | Me | H | H | H | Me | CO | Br | H | H | Me | Me |
| 6-56 | Me | H | H | H | Me | CO | Br | H | Me | Me | Me |
| 6-57 | Me | H | H | H | Me | CO | Br | Et | H | H | H |
| 6-58 | Me | H | H | H | Me | CO | Br | cPr | H | H | H |
| 6-59 | Me | H | H | H | Me | CO | Br | Ph | H | H | H |
| 6-60 | Me | H | H | H | Me | CO | Br | H | Et | H | H |
| 6-61 | Et | H | H | H | Me | CO | Cl | H | H | H | H |
| 6-62 | Et | H | H | H | Me | CO | Br | H | H | H | H |

-continued (11')

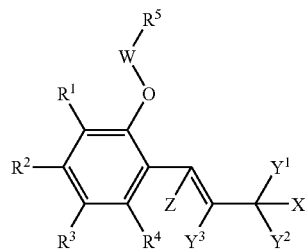

| Comp. No. | R¹ | R² | R³ | R⁴ | R⁵ | W | X | Z | Y¹ | Y² | Y³ |
|---|---|---|---|---|---|---|---|---|---|---|---|
| 6-63 | H | Et | H | H | Me | CO | Br | H | H | H | H |
| 6-64 | H | H | Et | H | Me | CO | Br | H | H | H | H |
| 6-65 | H | H | H | Et | Me | CO | Br | H | H | H | H |
| 6-66 | cPr | H | H | H | Me | CO | Cl | H | H | H | H |
| 6-67 | cPr | H | H | H | Me | CO | Br | H | H | H | H |
| 6-68 | H | cPr | H | H | Me | CO | Br | H | H | H | H |
| 6-69 | H | H | cPr | H | Me | CO | Br | H | H | H | H |
| 6-70 | H | H | H | cPr | Me | CO | Br | H | H | H | H |
| 6-71 | iPr | H | H | H | Me | CO | Cl | H | H | H | H |
| 6-72 | iPr | H | H | H | Me | CO | Br | H | H | H | H |
| 6-73 | H | iPr | H | H | Me | CO | Br | H | H | H | H |
| 6-74 | H | H | iPr | H | Me | CO | Br | H | H | H | H |
| 6-75 | H | H | H | iPr | Me | CO | Br | H | H | H | H |
| 6-76 | F | H | H | H | Me | CO | Cl | H | H | H | H |
| 6-77 | F | H | H | H | Me | CO | Br | H | H | H | H |
| 6-78 | H | F | H | H | Me | CO | Br | H | H | H | H |
| 6-79 | H | H | F | H | Me | CO | Br | H | H | H | H |
| 6-80 | H | H | H | F | Me | CO | Br | H | H | H | H |
| 6-81 | Cl | H | H | H | Me | CO | Cl | H | H | H | H |
| 6-82 | Cl | H | H | H | Me | CO | Br | H | H | H | H |
| 6-83 | H | Cl | H | H | Me | CO | Br | H | H | H | H |
| 6-84 | H | H | Cl | H | Me | CO | Br | H | H | H | H |
| 6-85 | H | H | H | Cl | Me | CO | Br | H | H | H | H |
| 6-86 | Br | H | H | H | Me | CO | Cl | H | H | H | H |
| 6-87 | Br | H | H | H | Me | CO | Br | H | H | H | H |
| 6-88 | H | Br | H | H | Me | CO | Br | H | H | H | H |
| 6-89 | H | H | Br | H | Me | CO | Br | H | H | H | H |
| 6-90 | H | H | H | Br | Me | CO | Br | H | H | H | H |
| 6-91 | I | H | H | H | Me | CO | Cl | H | H | H | H |
| 6-92 | I | H | H | H | Me | CO | Br | H | H | H | H |
| 6-93 | H | I | H | H | Me | CO | Br | H | H | H | H |
| 6-94 | H | H | I | H | Me | CO | Br | H | H | H | H |
| 6-95 | H | H | H | I | Me | CO | Br | H | H | H | H |
| 6-96 | Me | F | H | H | Me | CO | Cl | H | H | H | H |
| 6-97 | Me | F | H | H | Me | CO | Br | H | H | H | H |
| 6-98 | Me | H | F | H | Me | CO | Br | H | H | H | H |
| 6-99 | Me | H | H | F | Me | CO | Br | H | H | H | H |
| 6-100 | Me | Cl | H | H | Me | CO | Cl | H | H | H | H |
| 6-101 | Me | Cl | H | H | Me | CO | Br | H | H | H | H |
| 6-102 | Me | H | Cl | H | Me | CO | Br | H | H | H | H |
| 6-103 | Me | H | H | Cl | Me | CO | Br | H | H | H | H |
| 6-104 | Me | Br | H | H | Me | CO | Cl | H | H | H | H |
| 6-105 | Me | Br | H | H | Me | CO | Br | H | H | H | H |
| 6-106 | Me | H | Br | H | Me | CO | Br | H | H | H | H |
| 6-107 | Me | H | H | Br | Me | CO | Br | H | H | H | H |
| 6-108 | Et | Me | H | H | Me | CO | Cl | H | H | H | H |
| 6-109 | Et | Me | H | H | Me | CO | Br | H | H | H | H |
| 6-110 | Et | H | Me | H | Me | CO | Br | H | H | H | H |
| 6-111 | Et | H | H | Me | Me | CO | Br | H | H | H | H |
| 6-112 | Et | F | H | H | Me | CO | Br | H | H | H | H |
| 6-113 | Et | H | F | H | Me | CO | Br | H | H | H | H |
| 6-114 | Et | H | H | F | Me | CO | Br | H | H | H | H |
| 6-115 | Et | H | H | F | Me | CO | Br | H | H | H | H |
| 6-116 | Et | Cl | H | H | Me | CO | Br | H | H | H | H |
| 6-117 | Et | Cl | H | H | Me | CO | Br | H | H | H | H |
| 6-118 | Et | H | Cl | H | Me | CO | Br | H | H | H | H |
| 6-119 | Et | H | H | Cl | Me | CO | Br | H | H | H | H |
| 6-120 | iPr | Me | H | H | Me | CO | Br | H | H | H | H |
| 6-121 | iPr | Me | H | H | Me | CO | Br | H | H | H | H |
| 6-122 | iPr | H | Me | H | Me | CO | Br | H | H | H | H |
| 6-123 | iPr | H | H | Me | Me | CO | Br | H | H | H | H |
| 6-124 | iPr | F | H | H | Me | CO | Cl | H | H | H | H |
| 6-125 | iPr | F | H | H | Me | CO | Br | H | H | H | H |
| 6-126 | iPr | H | F | H | Me | CO | Br | H | H | H | H |
| 6-127 | iPr | H | H | F | Me | CO | Br | H | H | H | H |
| 6-128 | iPr | Cl | H | H | Me | CO | Cl | H | H | H | H |
| 6-129 | iPr | Cl | H | H | Me | CO | Br | H | H | H | H |
| 6-130 | iPr | H | Cl | H | Me | CO | Br | H | H | H | H |
| 6-131 | iPr | H | H | Cl | Me | CO | Br | H | H | H | H |
| 6-132 | cPr | Me | H | H | Me | CO | Cl | H | H | H | H |
| 6-133 | cPr | Me | H | H | Me | CO | Br | H | H | H | H |
| 6-134 | cPr | H | Me | H | Me | CO | Br | H | H | H | H |
| 6-135 | cPr | H | H | Me | Me | CO | Br | H | H | H | H |
| 6-136 | cPr | F | H | H | Me | CO | Cl | H | H | H | H |
| 6-137 | cPr | F | H | H | Me | CO | Br | H | H | H | H |
| 6-138 | cPr | H | F | H | Me | CO | Br | H | H | H | H |
| 6-139 | cPr | H | H | F | Me | CO | Br | H | H | H | H |
| 6-140 | cPr | Cl | H | H | Me | CO | Cl | H | H | H | H |
| 6-141 | cPr | Cl | H | H | Me | CO | Br | H | H | H | H |
| 6-142 | cPr | H | Cl | H | Me | CO | Br | H | H | H | H |
| 6-143 | cPr | H | H | Cl | Me | CO | Br | H | H | H | H |
| 6-144 | F | Me | H | H | Me | CO | Cl | H | H | H | H |
| 6-145 | F | Me | H | H | Me | CO | Br | H | H | H | H |
| 6-146 | F | H | Me | H | Me | CO | Br | H | H | H | H |
| 6-147 | F | H | H | Me | Me | CO | Br | H | H | H | H |
| 6-148 | F | F | H | H | Me | CO | Cl | H | H | H | H |
| 6-149 | F | F | H | H | Me | CO | Br | H | H | H | H |
| 6-150 | F | H | F | H | Me | CO | Br | H | H | H | H |
| 6-151 | F | H | H | F | Me | CO | Br | H | H | H | H |
| 6-152 | F | Cl | H | H | Me | CO | Cl | H | H | H | H |
| 6-153 | F | Cl | H | H | Me | CO | Br | H | H | H | H |
| 6-154 | F | H | Cl | H | Me | CO | Br | H | H | H | H |
| 6-155 | F | H | H | Cl | Me | CO | Br | H | H | H | H |
| 6-156 | Cl | Me | H | H | Me | CO | Cl | H | H | H | H |
| 6-157 | Cl | Me | H | H | Me | CO | Br | H | H | H | H |
| 6-158 | Cl | H | Me | H | Me | CO | Br | H | H | H | H |
| 6-159 | Cl | H | H | Me | Me | CO | Br | H | H | H | H |
| 6-160 | Cl | F | H | H | Me | CO | Cl | H | H | H | H |
| 6-161 | Cl | F | H | H | Me | CO | Br | H | H | H | H |
| 6-162 | Cl | H | F | H | Me | CO | Br | H | H | H | H |
| 6-163 | Cl | H | H | F | Me | CO | Br | H | H | H | H |
| 6-164 | Cl | Cl | H | H | Me | CO | Cl | H | H | H | H |
| 6-165 | Cl | Cl | H | H | Me | CO | Br | H | H | H | H |
| 6-166 | Cl | H | Cl | H | Me | CO | Br | H | H | H | H |
| 6-167 | Cl | H | H | Cl | Me | CO | Br | H | H | H | H |
| 6-168 | Br | Me | H | H | Me | CO | Cl | H | H | H | H |
| 6-169 | Br | Me | H | H | Me | CO | Br | H | H | H | H |
| 6-170 | Br | H | Me | H | Me | CO | Br | H | H | H | H |
| 6-171 | Br | H | H | Me | Me | CO | Br | H | H | H | H |
| 6-172 | Br | F | H | H | Me | CO | Cl | H | H | H | H |
| 6-173 | Br | F | H | H | Me | CO | Br | H | H | H | H |
| 6-174 | Br | H | F | H | Me | CO | Br | H | H | H | H |
| 6-175 | Br | H | H | F | Me | CO | Br | H | H | H | H |
| 6-176 | Br | Cl | H | H | Me | CO | Cl | H | H | H | H |
| 6-177 | Br | Cl | H | H | Me | CO | Br | H | H | H | H |
| 6-178 | Br | H | Cl | H | Me | CO | Br | H | H | H | H |
| 6-179 | Br | H | H | Cl | Me | CO | Br | H | H | H | H |
| 6-180 | Me | H | H | H | Et | CO | Br | H | H | H | H |
| 6-181 | Me | H | H | H | CH₂Cl | CO | Br | H | H | H | H |
| 6-182 | Me | H | H | H | CF₃ | CO | Br | H | H | H | H |
| 6-183 | Me | H | H | H | Bu-t | CO | Br | H | H | H | H |
| 6-184 | Me | H | H | H | OMe | CO | Br | H | H | H | H |
| 6-185 | Me | H | H | H | OEt | CO | Br | H | H | H | H |

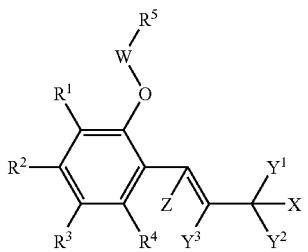

-continued

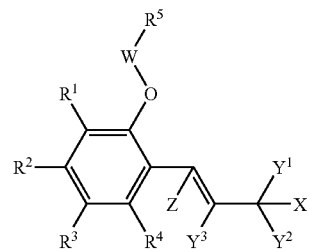

(11')

| Comp. No. | R¹ | R² | R³ | R⁴ | R⁵ | W | X | Z | Y¹ | Y² | Y³ |
|---|---|---|---|---|---|---|---|---|---|---|---|
| 6-186 | Me | H | H | H | Me | SO₂ | Br | H | H | H | H |
| 6-187 | Me | H | H | H | Ph | SO₂ | Br | H | H | H | H |

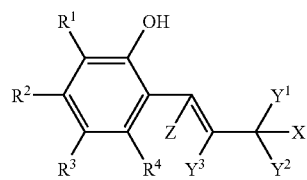

(11'')

| Comp. No. | R¹ | R² | R³ | R⁴ | X | Z | Y¹ | Y² | Y³ |
|---|---|---|---|---|---|---|---|---|---|
| 7-1 | H | H | H | H | Cl | H | H | H | H |
| 7-2 | H | H | H | H | Br | H | H | H | H |
| 7-3 | H | H | H | H | I | H | H | H | H |
| 7-4 | Me | H | H | H | Cl | H | H | H | H |
| 7-5 | Me | H | H | H | Br | H | H | H | H |
| 7-6 | Me | H | H | H | I | H | H | H | H |
| 7-7 | H | Me | H | H | Cl | H | H | H | H |
| 7-8 | H | Me | H | H | Br | H | H | H | H |
| 7-9 | H | H | Me | H | Cl | H | H | H | H |
| 7-10 | H | H | Me | H | Br | H | H | H | H |
| 7-11 | H | H | H | Me | Cl | H | H | H | H |
| 7-12 | H | H | H | Me | Br | H | H | H | H |
| 7-13 | H | H | H | H | Br | Me | H | H | H |
| 7-14 | H | H | H | H | Br | H | Me | H | H |
| 7-15 | H | H | H | H | Br | H | H | Me | H |
| 7-16 | H | H | H | H | Br | H | H | H | Me |
| 7-17 | Me | Me | H | H | Cl | H | H | H | H |
| 7-18 | Me | Me | H | H | Br | H | H | H | H |
| 7-19 | Me | H | Me | H | Cl | H | H | H | H |
| 7-20 | Me | H | Me | H | Br | H | H | H | H |
| 7-21 | Me | H | H | Me | Cl | H | H | H | H |
| 7-22 | Me | H | H | Me | Br | H | H | H | H |
| 7-23 | Me | H | H | H | Br | Me | H | H | H |
| 7-24 | Me | H | H | H | Br | H | Me | H | H |
| 7-25 | Me | H | H | H | Br | H | H | Me | H |
| 7-26 | Me | H | H | H | Br | H | H | H | Me |
| 7-27 | Me | Me | Me | H | Br | H | H | H | H |
| 7-28 | Me | Me | H | Me | Br | H | H | H | H |
| 7-29 | Me | Me | H | H | Br | Me | H | H | H |
| 7-30 | Me | Me | H | H | Br | H | Me | H | H |
| 7-31 | Me | Me | H | H | Br | H | H | Me | H |
| 7-32 | Me | Me | H | H | Br | H | H | H | Me |
| 7-33 | Me | Me | Me | Me | Br | Me | H | H | H |
| 7-34 | Me | Me | Me | Me | Br | H | Me | H | H |
| 7-35 | Me | Me | Me | Me | Br | H | H | Me | H |
| 7-36 | Me | Me | Me | Me | Br | H | H | H | Me |
| 7-37 | Me | Me | Me | Me | Cl | H | H | H | H |
| 7-38 | Me | Me | Me | Me | Br | H | H | H | H |
| 7-39 | Me | Me | Me | Me | Br | Me | H | H | H |
| 7-40 | Me | Me | Me | Me | Br | H | Me | H | H |
| 7-41 | Me | Me | Me | Me | Br | H | H | Me | H |
| 7-42 | Me | Me | Me | Me | Br | H | H | H | Me |
| 7-43 | H | Me | H | Me | Cl | H | H | H | H |
| 7-44 | H | Me | H | Me | Br | H | H | H | H |
| 7-45 | H | H | Me | Me | Br | H | H | H | H |
| 7-46 | Me | H | H | H | Br | Me | Me | H | H |
| 7-47 | Me | H | H | H | Br | Me | H | Me | H |
| 7-48 | Me | H | H | H | Br | Me | H | H | Me |
| 7-49 | Me | H | H | H | Br | Me | Me | Me | H |
| 7-50 | Me | H | H | H | Br | Me | Me | H | Me |
| 7-51 | Me | H | H | H | Br | Me | H | Me | Me |
| 7-52 | Me | H | H | H | Br | Me | Me | Me | Me |
| 7-53 | Me | H | H | H | Br | H | Me | Me | H |
| 7-54 | Me | H | H | H | Br | H | Me | H | Me |
| 7-55 | Me | H | H | H | Br | H | H | Me | Me |
| 7-56 | Me | H | H | H | Br | H | Me | Me | Me |
| 7-57 | Me | H | H | H | Br | Et | H | H | H |
| 7-58 | Me | H | H | H | Br | cPr | H | H | H |
| 7-59 | Me | H | H | H | Br | Ph | H | H | H |
| 7-60 | Me | H | H | H | Br | H | Et | H | H |
| 7-61 | Et | H | H | H | Cl | H | H | H | H |
| 7-62 | Et | H | H | H | Br | H | H | H | H |
| 7-63 | H | Et | H | H | Br | H | H | H | H |
| 7-64 | H | H | Et | H | Br | H | H | H | H |
| 7-65 | H | H | H | Et | Br | H | H | H | H |
| 7-66 | cPr | H | H | H | Cl | H | H | H | H |
| 7-67 | cPr | H | H | H | Br | H | H | H | H |
| 7-68 | H | cPr | H | H | Br | H | H | H | H |
| 7-69 | H | H | cPr | H | Br | H | H | H | H |
| 7-70 | H | H | H | cPr | Br | H | H | H | H |
| 7-71 | iPr | H | H | H | Cl | H | H | H | H |
| 7-72 | iPr | H | H | H | Br | H | H | H | H |
| 7-73 | H | iPr | H | H | Br | H | H | H | H |
| 7-74 | H | H | iPr | H | Br | H | H | H | H |
| 7-75 | H | H | H | iPr | Br | H | H | H | H |
| 7-76 | F | H | H | H | Cl | H | H | H | H |
| 7-77 | F | H | H | H | Br | H | H | H | H |
| 7-78 | H | F | H | H | Br | H | H | H | H |
| 7-79 | H | H | F | H | Br | H | H | H | H |
| 7-80 | H | H | H | F | Br | H | H | H | H |
| 7-81 | Cl | H | H | H | Cl | H | H | H | H |
| 7-82 | Cl | H | H | H | Br | H | H | H | H |
| 7-83 | H | Cl | H | H | Br | H | H | H | H |
| 7-84 | H | H | Cl | H | Br | H | H | H | H |
| 7-85 | H | H | H | Cl | Br | H | H | H | H |
| 7-86 | Br | H | H | H | Cl | H | H | H | H |
| 7-87 | Br | H | H | H | Br | H | H | H | H |
| 7-88 | H | Br | H | H | Br | H | H | H | H |
| 7-89 | H | H | Br | H | Br | H | H | H | H |
| 7-90 | H | H | H | Br | Br | H | H | H | H |
| 7-91 | I | H | H | H | Cl | H | H | H | H |
| 7-92 | I | H | H | H | Br | H | H | H | H |
| 7-93 | H | I | H | H | Br | H | H | H | H |
| 7-94 | H | H | I | H | Br | H | H | H | H |
| 7-95 | H | H | H | I | Br | H | H | H | H |
| 7-96 | Me | F | H | H | Cl | H | H | H | H |
| 7-97 | Me | F | H | H | Br | H | H | H | H |
| 7-98 | Me | H | F | H | Br | H | H | H | H |
| 7-99 | Me | H | H | F | Br | H | H | H | H |
| 7-100 | Me | Cl | H | H | Cl | H | H | H | H |
| 7-101 | Me | Cl | H | H | Br | H | H | H | H |
| 7-102 | Me | H | Cl | H | Br | H | H | H | H |
| 7-103 | Me | H | H | Cl | Br | H | H | H | H |
| 7-104 | Me | Br | H | H | Cl | H | H | H | H |
| 7-105 | Me | Br | H | H | Br | H | H | H | H |
| 7-106 | Me | H | Br | H | Br | H | H | H | H |
| 7-107 | Me | H | H | Br | Br | H | H | H | H |

(11″)

| Comp. No. | R¹ | R² | R³ | R⁴ | X | Z | Y¹ | Y² | Y³ |
|---|---|---|---|---|---|---|---|---|---|
| 7-108 | Et | Me | H | H | Cl | H | H | H | H |
| 7-109 | Et | Me | H | H | Br | H | H | H | H |
| 7-110 | Et | H | Me | H | Br | H | H | H | H |
| 7-111 | Et | H | H | Me | Br | H | H | H | H |
| 7-112 | Et | F | H | H | Cl | H | H | H | H |
| 7-113 | Et | F | H | H | Br | H | H | H | H |
| 7-114 | Et | H | F | H | Br | H | H | H | H |
| 7-115 | Et | H | H | F | Br | H | H | H | H |
| 7-116 | Et | Cl | H | H | Cl | H | H | H | H |
| 7-117 | Et | Cl | H | H | Br | H | H | H | H |
| 7-118 | Et | H | Cl | H | Br | H | H | H | H |
| 7-119 | Et | H | H | Cl | Br | H | H | H | H |
| 7-120 | iPr | Me | H | H | Cl | H | H | H | H |
| 7-121 | iPr | Me | H | H | Br | H | H | H | H |
| 7-122 | iPr | H | Me | H | Br | H | H | H | H |
| 7-123 | iPr | H | H | Me | Br | H | H | H | H |
| 7-124 | iPr | F | H | H | Cl | H | H | H | H |
| 7-125 | iPr | F | H | H | Br | H | H | H | H |
| 7-126 | iPr | H | F | H | Br | H | H | H | H |
| 7-127 | iPr | H | H | F | Br | H | H | H | H |
| 7-128 | iPr | Cl | H | H | Cl | H | H | H | H |
| 7-129 | iPr | Cl | H | H | Br | H | H | H | H |
| 7-130 | iPr | H | Cl | H | Br | H | H | H | H |
| 7-131 | iPr | H | H | Cl | Br | H | H | H | H |
| 7-132 | cPr | Me | H | H | Cl | H | H | H | H |
| 7-133 | cPr | Me | H | H | Br | H | H | H | H |
| 7-134 | cPr | H | Me | H | Br | H | H | H | H |
| 7-135 | cPr | H | H | Me | Br | H | H | H | H |
| 7-136 | cPr | F | H | H | Cl | H | H | H | H |
| 7-137 | cPr | F | H | H | Br | H | H | H | H |
| 7-138 | cPr | H | F | H | Br | H | H | H | H |
| 7-139 | cPr | H | H | F | Br | H | H | H | H |
| 7-140 | cPr | Cl | H | H | Cl | H | H | H | H |
| 7-141 | cPr | Cl | H | H | Br | H | H | H | H |
| 7-142 | cPr | H | Cl | H | Br | H | H | H | H |
| 7-143 | cPr | H | H | Cl | Br | H | H | H | H |
| 7-144 | F | Me | H | H | Cl | H | H | H | H |
| 7-145 | F | Me | H | H | Br | H | H | H | H |
| 7-146 | F | H | Me | H | Br | H | H | H | H |
| 7-147 | F | H | H | Me | Br | H | H | H | H |
| 7-148 | F | F | H | H | Cl | H | H | H | H |
| 7-149 | F | F | H | H | Br | H | H | H | H |
| 7-150 | F | H | F | H | Br | H | H | H | H |
| 7-151 | F | H | H | F | Br | H | H | H | H |
| 7-152 | F | Cl | H | H | Cl | H | H | H | H |
| 7-153 | F | Cl | H | H | Br | H | H | H | H |
| 7-154 | F | H | Cl | H | Br | H | H | H | H |
| 7-155 | F | H | H | Cl | Br | H | H | H | H |
| 7-156 | Cl | Me | H | H | Cl | H | H | H | H |
| 7-157 | Cl | Me | H | H | Br | H | H | H | H |
| 7-158 | Cl | H | Me | H | Br | H | H | H | H |
| 7-159 | Cl | H | H | Me | Br | H | H | H | H |
| 7-160 | Cl | F | H | H | Cl | H | H | H | H |
| 7-161 | Cl | F | H | H | Br | H | H | H | H |
| 7-162 | Cl | H | F | H | Br | H | H | H | H |
| 7-163 | Cl | H | H | F | Br | H | H | H | H |
| 7-164 | Cl | Cl | H | H | Cl | H | H | H | H |
| 7-165 | Cl | Cl | H | H | Br | H | H | H | H |
| 7-166 | Cl | H | Cl | H | Br | H | H | H | H |
| 7-167 | Cl | H | H | Cl | Br | H | H | H | H |
| 7-168 | Br | Me | H | H | Cl | H | H | H | H |
| 7-169 | Br | Me | H | H | Br | H | H | H | H |
| 7-170 | Br | H | Me | H | Br | H | H | H | H |
| 7-171 | Br | H | H | Me | Br | H | H | H | H |
| 7-172 | Br | F | H | H | Cl | H | H | H | H |
| 7-173 | Br | F | H | H | Br | H | H | H | H |
| 7-174 | Br | H | F | H | Br | H | H | H | H |
| 7-175 | Br | H | H | F | Br | H | H | H | H |
| 7-176 | Br | Cl | H | H | Cl | H | H | H | H |
| 7-177 | Br | Cl | H | H | Br | H | H | H | H |
| 7-178 | Br | H | Cl | H | Br | H | H | H | H |
| 7-179 | Br | H | H | Cl | Br | H | H | H | H |

The following provides an explanation of the process of the present invention. In the process of the present invention, although a compound of general formula (10) can be produced by a ring closure reaction of a compound of general formula (7) (a compound of general formula (7') and a compound of general formula (7″)), this compound of general formula (7) can also be produced from a compound of general formula (3). Moreover, this compound of general formula (3) can be produced from a compound of general formula (1). This step is indicated with the following reaction formula. A compound represented by general formula (3) is obtained by using a compound represented by general formula (1) as a raw material, followed by converting a compound represented by general formula (3) to a compound represented by general formula (7') or (7″). Moreover, a compound represented by general formula (7') or (7″) is converted to a cyclopropyl phenyl ester derivative (9') or cyclopropylphenol derivative (10) (a compound of general formula (9') and a compound of general formula (10) compose a compound of the aforementioned general formula (9)) followed by finally converting the cyclopropyl phenyl ester derivative (9') to cyclopropylphenol derivative (10).

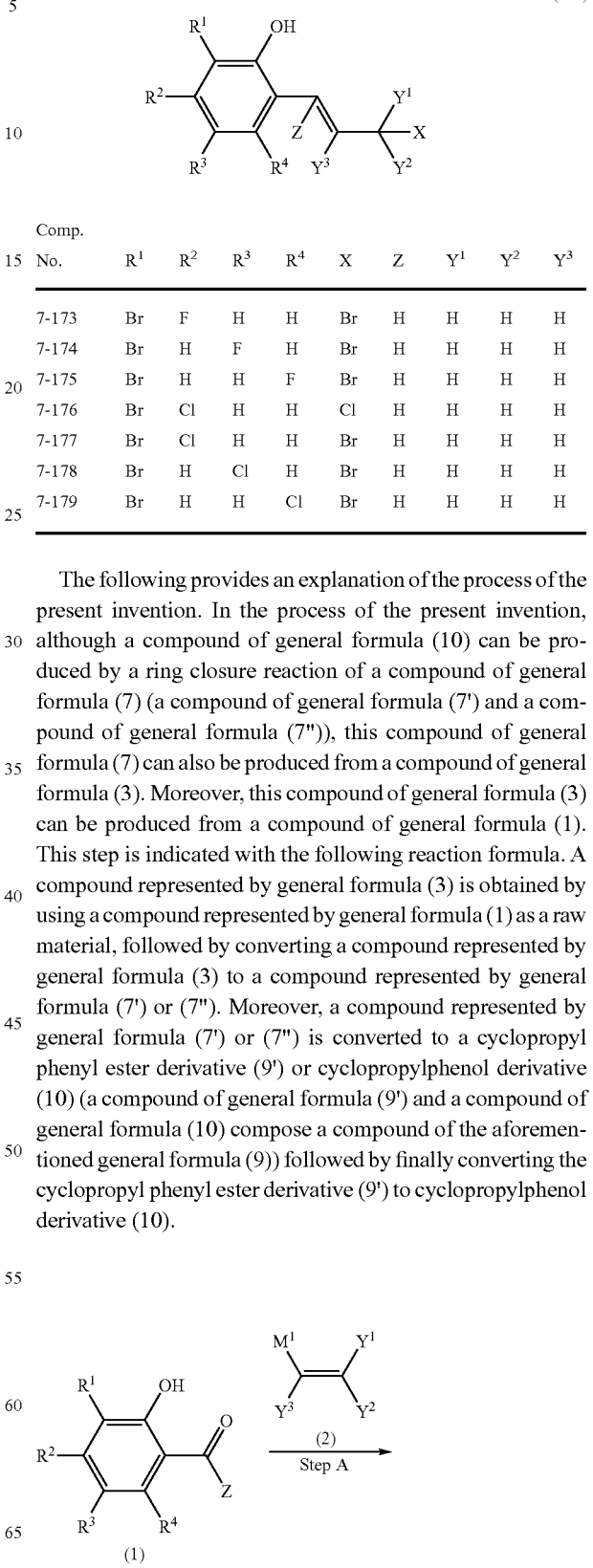

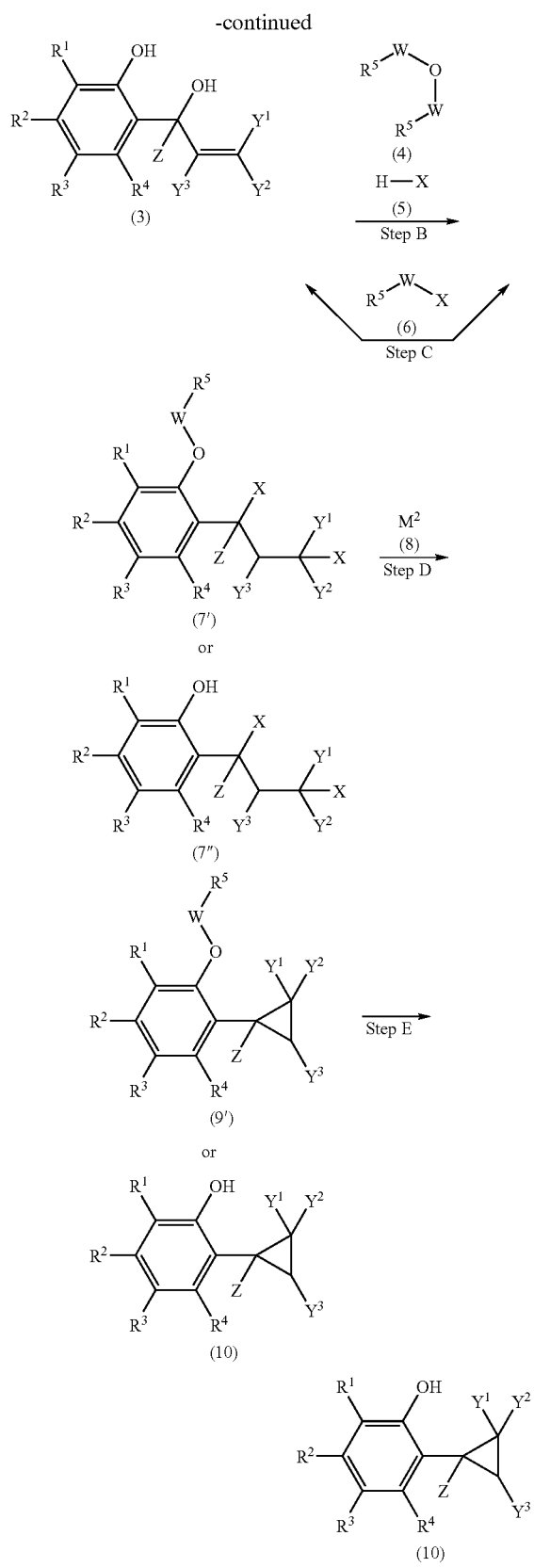

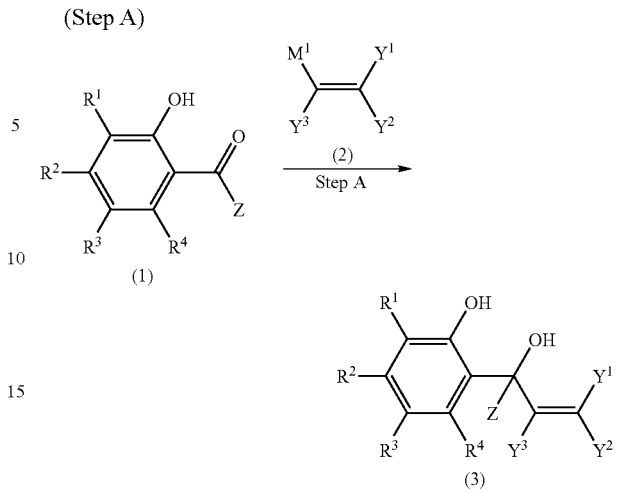

(Step A)

In the above formulas, $R^1$, $R^2$, $R^3$, $R^4$, $M^1$, $Y^1$, $Y^2$, $Y^3$ and Z are the same as previously defined.

Step A is a step to prepare an alcohol derivative represented by general formula (3) by an addition reaction of a vinyl metal compound represented by formula (2) with a carbonyl derivative represented by formula (1).

The vinyl metal compound used in this step is not particularly limited provided it may bond to a carbonyl compound to give alcohol derivatives, examples of which include a vinyl lithium compound such as vinyl lithium, 1-methylvinyl lithium, propenyl lithium, 1-methylpropenyl lithium, 2-methylpropenyl lithium, 1,2-dimethylpropenyl lithium, cyclohexenyl lithium, 1-methoxyvinyl lithium, 1-ethoxyvinyl lithium, 2-ethoxyvinyl lithium, 2,2-diethoxyvinyl lithium, 1-methylthiovinyl lithium, trifluorovinyl lithium, 4-t-butylcyclohexenyl lithium, 1-(trimethylsilyl)vinyl lithium, 2-(trimethylsilyl)vinyl lithium, 2,2-difluorovinyl lithium, 1-vinylvinyl lithium, 2-vinylvinyl lithium, 1-phenylvinyl lithium, and 2-phenylvinyl lithium; a vinylboron compound such as vinylboronic acid, hexeneboronic acid, and octeneboronic acid; a vinyl sodium compound such as vinyl sodium, decenyl sodium, and propanedienyl sodium; a vinyl magnesium compound such as vinyl magnesium chloride, vinyl magnesium bromide, vinyl magnesium iodide, propenylmagnesium chloride, propenylmagnesium bromide, (1-methylvinyl)magnesium chloride, (1-methylvinyl)magnesium bromide, (1-ethylvinyl)magnesium bromide, (1-isopropylvinyl)magnesium bromide, (1-methylpropenyl)magnesium bromide, (2-methylpropenyl)magnesium bromide, (1-ethylbutenyl)magnesium bromide, hexenyl magnesium bromide, heptenyl magnesium bromide, (2,4-dimethylpentenyl)magnesium bromide, cyclohexenyl magnesium bromide, {2-(2-phenylvinyl)cyclopentenyl}magnesium bromide, (trifluorovinyl)magnesium bromide, (perfluorooctenyl)magnesium bromide, (1-vinylvinyl)magnesium chloride, (1-vinylvinyl)magnesium bromide, (1-trimethylsilylvinyl)magnesium bromide, (1-trimethylsilylpropenyl)magnesium bromide, (2-trimethylsilylvinyl)magnesium bromide, (1-trimethylsilylhexyl)magnesium bromide, {1-(dimethylaminomethyl)vinyl}magnesium bromide, {1-(1-pyrrolidinylmethyl)vinyl}magnesium bromide, {3-(N,N-diethylamino)propenyl}magnesium bromide, {1-(trimethylsilylmethyl)vinyl}magnesium bromide, (1-phenylvinyl)magnesium bromide, (2-phenylvinyl)magnesium bromide, {3-(benzyloxy)propenyl}magnesium bromide, {3-(t-butyldiphenylsilyloxy)propenyl}magnesium bromide, {4-ethoxy-1,3-butadienyl}magnesium bromide, {1-(1,3-benzo dioxol-5-yl)vinyl}magnesium bromide, cyclobutene magnesium In the above formulas, $R^1$, $R^2$, $R^3$, $R^4$, $R^5$, $M^1$, $M^2$, W, X, $Y^1$, $Y^2$, $Y^3$ and Z are the same as previously defined.

bromide, {3-(benzyloxymethoxy)pentenyl}magnesium bromide, (2-butyl-2-vinylvinyl)magnesium chloride, (2-heptyl-2-vinylvinyl)magnesium chloride, {1-decyl-2-(dimethylphenylsilyl)vinyl}magnesium bromide, (cyclobutylidenemethyl)magnesium bromide, (cyclohexylidenmethyl)magnesium bromide, propadienyl magnesium bromide, a divinyl magnesium; a vinyl aluminium compound such as vinyl aluminium dichloride, divinyl aluminium chloride, propanedienyl aluminium dibromide, di(propanedienyl) aluminium bromide, vinyl dimethyl aluminium, (divinyl)(methyl)aluminium, vinyl diethyl aluminium, (2-methylhexenyl)dimethyl aluminium, (2-methylheptenyl) dimethyl aluminium, trivinyl aluminium, and tripropenyl aluminium; a vinyl potassium compound such as vinyl potassium, and butenyl potassium; a vinyl calcium compound such as vinyl calcium chloride, vinyl calcium bromide, and vinyl calcium iodide; a vinyl titanium compound such as vinyl trichlorotitanium, and tetravinyl titanium; a vinyl manganese compound such as vinyl manganese chloride, vinyl manganese bromide, vinyl manganese iodide, (2-methylpropenyl) manganese chloride, (2-methylpropenyl)manganese bromide, and (2-methylpropenyl)manganese iodide; a vinyl copper compound such as vinyl copper, propenyl copper, butenyl copper, (2-methylbutenyl)copper, (2-methylpentenyl)copper, (2-ethylhexenyl)copper, and (2-butylhexenyl) copper; a vinyl zinc compound such as vinyl zinc chloride, vinyl zinc bromide, vinyl zinc iodide, (1-methylvinyl)zinc chloride, propenyl zinc bromide, (methyl)(vinyl)zinc, (ethyl)(hexenyl)zinc, divinyl zinc, and bis(1-propyl-1,2-propadienyl)zinc; a vinyl tin compound such as (trimethyl)(vinyl)tin, (tributyl)(vinyl)tin, (trimethyl)(1-methylvinyl)tin, {1-(2-chloroethyl)vinyl}(trimethyl)tin, {1-(3-chloropropyl)vinyl} (trimethyl)tin, {2-(trimethylsilyl)vinyl}(tributyl)tin, {(3-methoxymethoxy)propyl-1,2-nonadienyl}(tributyl)tin, and tetravinyl tin; a vinyl tellurium compound such as divinyl tellane, (butyl)(2-phenylvinyl)telluride, (butyl)(1-phenyl vinyl)telluride, (butyl)(2-methylpropenyl)telluride, and (butyl)(4-methoxy-1,2-butadienyl)telluride; a vinyl cerium compound such as vinyl cerium dichloride, 1-methylvinyl cerium dichloride, octenylcerium dichloride, cyclopentenyl cerium dichloride, 2-phenylvinyl cerium dichloride, (1-trimethylsilylhexenyl)cerium dichloride, (1-ethoxyvinyl)cerium dichloride, and trivinyl cerium; a vinyl samarium compound such as vinyl samarium chloride, vinyl samarium bromide, and vinyl samarium iodide; a vinyl europium compound such as vinyl europium chloride, vinyl europium bromide, and vinyl europium iodide; a vinyl ytterbium compound such as vinyl ytterbium chloride, vinyl ytterbium bromide, vinyl ytterbium iodide, preferably a vinyl lithium compound such as vinyl lithium, 1-methylvinyl lithium, and propenyl lithium; a vinyl boron compound such as vinyl boronic acid, and hexeneboronic acid; a vinyl magnesium compound such as vinyl magnesium chloride, vinyl magnesium bromide, vinyl magnesium iodide, propenyl magnesium chloride, propenyl magnesium bromide, (1-methylvinyl)magnesium chloride, (1-methylvinyl)magnesium bromide, and divinyl magnesium; a vinyl aluminium compound such as vinyl aluminium dichloride, divinyl aluminium chloride, propanedienyl aluminium dibromide, di(propanedienyl)aluminium bromide, vinyl dimethyl aluminium, (divinyl)(methyl)aluminium, and vinyl diethyl aluminium; a vinyl manganese compound such as vinyl manganese chloride, vinyl manganese bromide, vinyl manganese iodide, (2-methylpropenyl)manganese chloride, (2-methylpropenyl)manganese bromide, and (2-methylpropenyl)manganese iodide; a vinyl copper compound such as vinyl copper, propenyl copper, and butenyl copper; a vinyl zinc compound such as vinyl zinc chloride, vinyl zinc bromide, vinyl zinc iodide, (1-methylvinyl)zinc chloride, propenyl zinc bromide, (methyl)(vinyl)zinc, (ethyl)(hexenyl)zinc, divinyl zinc, and bis(1-propyl-1,2-propadienyl)zinc; a vinyl tin compound such as (trimethyl)(vinyl)tin, (tributyl)(vinyl) tin, (trimethyl)(1-methylvinyl)tin, {1-(2-chloroethyl)vinyl} (trimethyl)tin, {1-(3-chloropropyl)vinyl}(trimethyl)tin, {2-(trimethylsilyl)vinyl}(tributyl)tin, {(3-methoxymethoxy) propyl-1,2-nonadienyl}(tributyl)tin, and tetravinyl tin; a vinyl tellurium compound such as divinyltellane, (butyl)(2-phenylvinyl)telluride, (butyl)(1-phenylvinyl)telluride, (butyl)(2-methylpropenyl)telluride, and (butyl)(4-methoxy-1,2-butadienyl)telluride; a vinyl cerium compound such as vinylcerium dichloride, 1-methylvinyl cerium dichloride, octenyl cerium dichloride, cyclopentenyl cerium dichloride, 2-phenylvinyl cerium dichloride, (1-trimethylsilylhexenyl) cerium dichloride, (1-ethoxyvinyl)cerium dichloride, and trivinyl cerium; a vinyl samarium compound such as vinyl samarium chloride, vinyl samarium bromide, vinyl samarium iodide, more preferably vinyl lithium, vinyl magnesium chloride, vinyl magnesium bromide, vinyl magnesium iodide, propenyl magnesium chloride, propenyl magnesium bromide, (1-methylvinyl) magnesium chloride, vinyl zinc chloride, vinyl zinc bromide, divinyl zinc, most preferably vinyl magnesium chloride, vinyl magnesium bromide.

The amount of the vinyl metal compound (2) to be used in the present step is normally 0.5 to 20 mol and preferably 2 to 4 mol based on 1 mol of compound (1).

There are no particular limitations on the solvent used in the present step provided it does not inhibit the reaction, and examples include hydrocarbons such as heptane, hexane, cycloheptane or cyclohexane; aromatic hydrocarbons such as benzene, toluene or xylene; halogenated hydrocarbons such as dichloromethane, dichloroethane, chloroform or tetrachloroethane; ethers such as dioxane, diethyl ether, tetrahydrofuran (THF) or ethylene glycol dimethyl ether; esters such as methyl acetate, ethyl acetate or propyl acetate; and, mixed solvents thereof, preferable examples include ethers and mixed solvents of ethers and aromatic hydrocarbons, and more preferable examples include tetrahydrofuran and a mixed solvent of tetrahydrofuran and toluene.

The reaction temperature may vary depending on starting materials, reaction reagents and the kind of solvents used, etc., and is usually −70 to 200° C., preferably 0 to 50° C.

The reaction time varies depending on the raw material compounds, reaction reagents, solvents, reaction temperature and the like and is usually 1 hour to 100 hours, preferably 2 hours to 24 hours.

The compound (1) used in this step is a known compound or can be manufactured according to a conventional method (e.g., a method described in Acta Chem. Scand., Vol. 53, p 258 (1999) or J. Chem. Soc. Perkin Trans. 1, p 1862 (1986)).

(Step B)

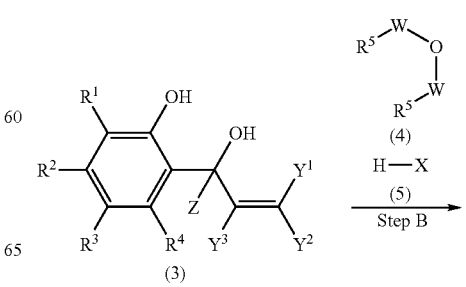

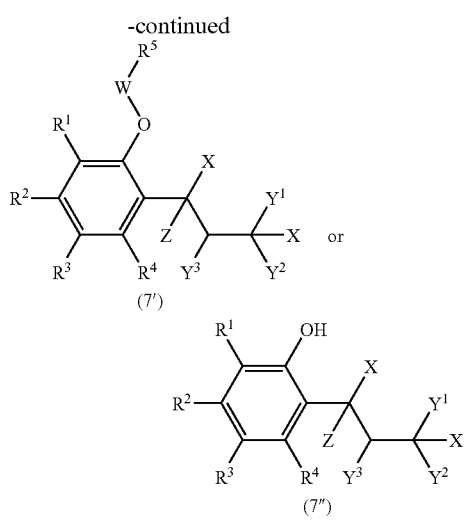

(7')

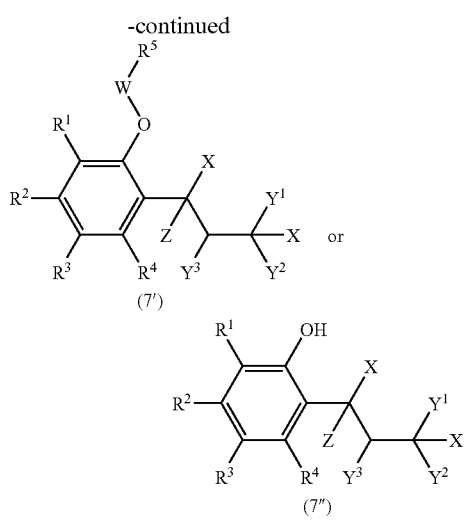

(7")

[wherein $R^1$, $R^2$, $R^3$, $R^4$, $R^5$, W, X, $Y^1$, $Y^2$, $Y^3$, and Z are the same as previously defined.]

Step B is a step to prepare an esterified dihalogenated compound represented by general formula (7') or a dihalogenated compound (7") by dihalogenation of alcohol derivatives represented by general formula (3) with acid anhydride (4) and hydrogen halide (5).

An acid anhydride (4) used in this step is not particularly limited provided it acylates hydroxyl group, examples of which include acetic anhydride, propionic anhydride, butyric anhydride, isobutyric anhydride, difluoroacetic anhydride, trifluoroacetic anhydride, benzoic anhydride, methanesulfonic anhydride, trifluoromethanesulfonic anhydride, more preferably acetic anhydride.

The amount of acid anhydride (4) to be used is usually 1.5 to 20 mol, preferably 2 to 5 mol based on 1 mol of compound (3).

A hydrogen halide (5) used in this step is not particularly limited provided it halogenates hydroxyl group and react with double bond to add halogen and hydrogen atom, examples of which include hydrogen fluoride, hydrogen chloride, hydrogen bromide, or hydrogen iodide, preferably hydrogen chloride, hydrogen bromide, more preferably hydrogen bromide.

The amount of hydrogen halide (5) to be used in this step is usually 2 to 30 mol, preferably 3 to 10 mol based on 1 mol of compound (3).

The solvent used in this step is not particularly limited provided it may not inhibit reactions, examples of which include hydrocarbons such as heptane, hexane, cycloheptane, cyclohexane; aromatic hydrocarbons such as benzene, toluene, xylene; halogenated hydrocarbons such as dichloromethane, dichloroethane, chloroform, tetrachloroethane; ethers such as dioxane, diethyl ether, tetrahydrofuran (THF), ethyleneglycol dimethyl ether; esters such as methyl acetate, ethyl acetate, propyl acetate; organic acids such as formic acid, acetic acid, propionic acid, trifluoroacetic acid, difluoroacetic acid, methanesulfonic acid, trifluoromethanesulfonic acid; or mixture solvent thereof, preferably aromatic hydrocarbons, halogenated hydrocarbons, organic acids, or mixture solvent thereof, more preferably toluene, dichloromethane, acetic acid or mixture solvent thereof, particularly preferably acetic acid, mixture solvent of acetic acid and toluene.

The reaction temperature varies depending on the raw material compounds, reaction reagents, solvents and the like, and is usually 0° C. to 200° C., preferably 20° C. to 80° C.

The reaction time varies depending on the raw material compounds, reaction reagents, solvents, reaction temperature and the like and is usually 1 hour to 100 hours, preferably 2 hours to 24 hours.

(Step C)

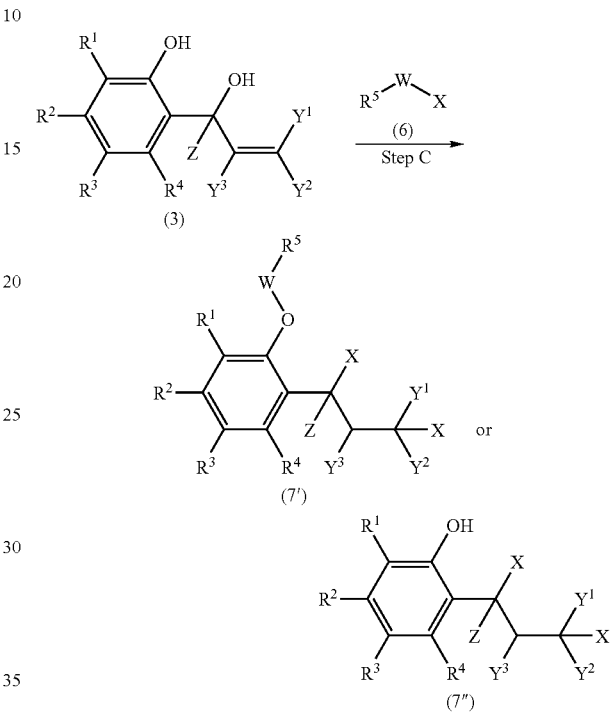

[wherein $R^1$, $R^2$, $R^3$, $R^4$, $R^5$, W, X, $Y^1$, $Y^2$, $Y^3$, and Z are the same as previously defined.]

Step C is a step to prepare an esterified dihalogenated compound (7') or dihalogenated compound (7") by reacting acid halide (6) with alcohol derivatives represented by general formula (3).

Acid halide (6) used in this step is not particularly limited provided it halogenates allyl alcohol, which may include acetyl chloride, acetyl bromide, acetyl iodide, propionyl bromide, pivaloyl chloride, trifluoroacetyl chloride, trichloroacetyl chloride, benzoyl chloride, methanesulfinyl chloride, methanesulfonyl chloride, benzenesulfonyl chloride, toluenesulfonyl chloride, chloro benzenesulfonyl chloride, trifluoromethanesulfonyl chloride, preferably acetyl chloride, acetyl bromide, methanesulfonyl chloride, toluenesulfonyl chloride, most preferably acetyl bromide.

The amount of acid halide (6) to be used in this step is usually 1 to 20 mol, preferably 1 to 4 mol based on 1 mol of compound (3).

The reaction may be carried out in the presence of acid. The acid to be used is not particularly limited, provided it does not inhibit reactions, which may include formic acid, acetic acid, propionic acid, pivalic acid, trifluoroacetic acid, trichloroacetic acid, benzoic acid, methanesulfonic acid, benzenesulfonic acid, toluenesulfonic acid, chlorobenzenesulfonic acid, trifluoromethanesulfonic acid, preferably formic acid, acetic acid, propionic acid, trifluoroacetic acid, methanesulfonic acid, trifluoromethanesulfonic acid, and most preferably acetic acid.

The solvent used in this step is not particularly limited, provided it does not inhibit reactions, examples of which include hydrocarbons such as heptane, hexane, cycloheptane, cyclohexane; aromatic hydrocarbons such as benzene, toluene, xylene; halogenated hydrocarbons such as dichloromethane, dichloroethane, chloroform, tetrachloroethane; ethers such as dioxane, diethyl ether, tetrahydrofuran (THF), ethyleneglycol dimethyl ether; esters such as methyl acetate, ethyl acetate, propyl acetate; organic acid such as formic acid, acetic acid, propionic acid, trifluoroacetic acid, difluoroacetic acid, methanesulfonic acid, trifluoromethanesulfonic acid; or mixture solvent thereof, preferably aromatic hydrocarbons, halogenated hydrocarbons, organic acids, or mixture solvent thereof, more preferably toluene, dichloromethane, acetic acid or mixture solvent thereof, and most preferably acetic acid, and mixture solvent of acetic acid and toluene.

The reaction temperature varies depending on the raw material compounds, reaction reagents, solvents and the like, and is usually 0° C. to 200° C., preferably 20° C. to 70° C.

The reaction time varies depending on the raw material compounds, reaction reagents, solvents, reaction temperature and the like and is usually 1 hour to 10 days, preferably 2 hours to 5 days.

(Step D)

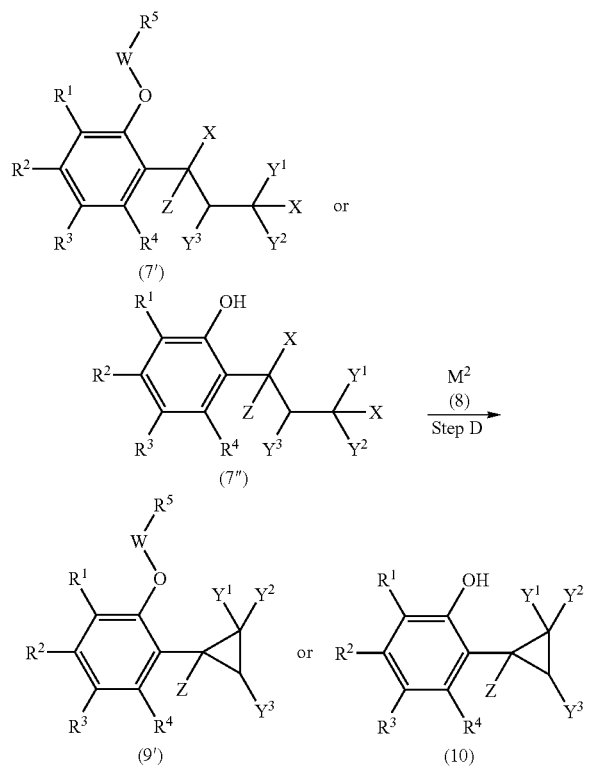

[wherein $R^1$, $R^2$, $R^3$, $R^4$, $R^5$, $M^2$, W, X, $Y^1$, $Y^2$, $Y^3$, and Z are the same as previously defined.]

Step D is a step to prepare cyclopropyl phenyl ester derivatives represented by general formula (9') or cyclopropyl phenol derivatives represented by general formula (10) by an intramolecular 3-membered ring forming reaction, which is carried out by reacting (1,3-dihaloalkyl)phenyl ester derivatives represented by general formula (7') or (1,3-dihaloalkyl) phenol derivatives represented by general formula (7") with metal (or metal salt) (8).

Metal, metal salt, or organic metal compound $M^2$ (8) used in this step is not particularly limited provided it converts halide to an organic metal compound by halogen-metal exchange reaction, examples of which include lithium, lithium alloy, sodium, magnesium, magnesium salt (e.g., magnesium chloride, magnesium bromide, magnesium iodide), potassium, nickel, nickel salt, copper, copper salt, zinc, zinc salt, zinc alloy (e.g., zinc-copper alloy, zinc-silver alloy), chromium, chromium salt, methyl lithium, butyl lithium, t-butyl lithium, phenyl lithium, methyl magnesium chloride, methyl magnesium bromide, phenyl magnesium chloride, phenyl magnesium bromide or calcium, preferably lithium, lithium alloy, sodium, magnesium, magnesium salt, potassium, nickel, nickel salt, copper, copper salt, zinc, zinc salt, zinc alloy (e.g., zinc-copper alloy), or t-butyl lithium, more preferably magnesium, zinc, or zinc-copper alloy, and even more preferably magnesium.

Metal magnesium used in this step may be activated using catalytic amount of iodine or dibromoethane and the like as necessary.

The amount of metal, metal salt, or organic metal compound (8) to be used in this step is usually 1 to 10 mol, preferably 1 to 4 mol based on 1 mol of compound (7') or (7").

The reaction temperature varies depending on the raw material compounds, reaction reagents, solvents and the like, and is usually 0° C. to 200° C., preferably 20° C. to 100° C.

The solvent used in this step is not particularly limited provided it does not inhibit reactions, examples of which include hydrocarbons such as heptane, hexane, cycloheptane, cyclohexane; aromatic hydrocarbons such as benzene, toluene, xylene; ethers such as dioxane, diethyl ether, tetrahydrofuran (THF), ethyleneglycol dimethyl ether; or mixture solvent thereof, preferably diethyl ether, tetrahydrofuran (THF), mixture solvent of tetrahydrofuran (THF) and toluene, most preferably tetrahydrofuran (THF), mixture solvent of tetrahydrofuran (THF) and toluene.

(Step E)

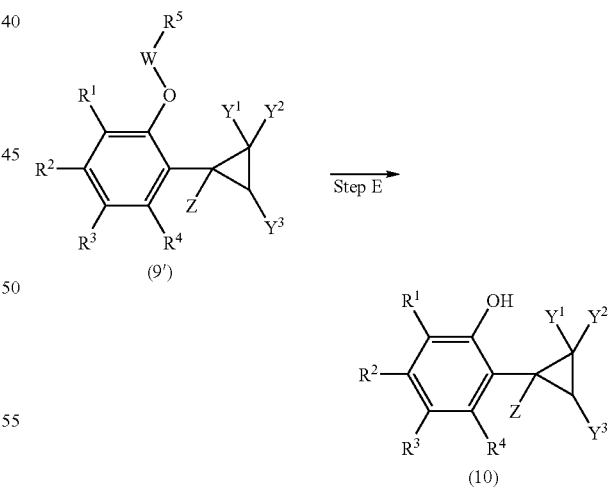

[wherein $R^1$, $R^2$, $R^3$, $R^4$, $R^5$, W, $Y^1$, $Y^2$, $Y^3$, and Z are the same as previously defined.]

Step E is a step to prepare cyclopropyl phenol derivatives represented by general formula (10) of the present invention by hydrolysis reaction of cyclopropylphenyl ester derivatives represented by general formula (9') obtained in Step D.

This step is carried out preferably in the presence of a base or acid.

The base used in this step is not particularly limited provided it hydrolyzes ester, examples of which include alkaline metal carbonate such as lithium carbonate, sodium carbonate, potassium carbonate, cesium carbonate; alkaline metal hydrogencarbonate such as sodium hydrogen carbonate, or potassium hydrogen carbonate; alkaline metal hydroxide or alkaline earth metal hydroxide such as lithium hydroxide, sodium hydroxide, potassium hydroxide, barium hydroxide; alkaline metal alkoxide such as sodium methoxide, sodium ethoxide, potassium-t-butoxide; organic base such as triethylamine, tributylamine, diisopropyl ethylamine, N-methylmorpholine, pyridine, 4-(N,N-dimethylamino)pyridine, N,N-dimethylaniline, N,N-diethylaniline, 1,5-diazabicyclo[4.3.0]non-5-ene, 1,4-diazabicyclo[2.2.2]octane (DABCO), 1,8-diazabicyclo[5.4.0]undec-7-ene (DBU), preferably alkaline metal carbonate, alkaline metal hydroxide, more preferably potassium carbonate, sodium hydroxide, and potassium hydroxide.

methyl isobutyl ketone, cyclohexanone; dimethylsulfoxide (DMSO); or mixture solvent thereof, preferably alcohols and water, and more preferably methanol and mixture solvent of methanol-water.

In the process of the present invention, a compound of general formula (7) can be obtained, as described above, by reacting a compound of general formula (3) with a mixture of compounds of general formula (4) and general formula (5) or by reacting it with acid halide of general formula (6). In this reaction, a compound of general formula (11) may be produced with a compound of formula (7). In such a case, a compound of general formula (11) can be converted to a compound of general formula (7) by further reacting it with hydrogen halide of general formula (5). This reaction can also be carried out by using a mixture of a compounds of general formula (11) and general formula (7). This step also constitutes a part of the process of present invention.

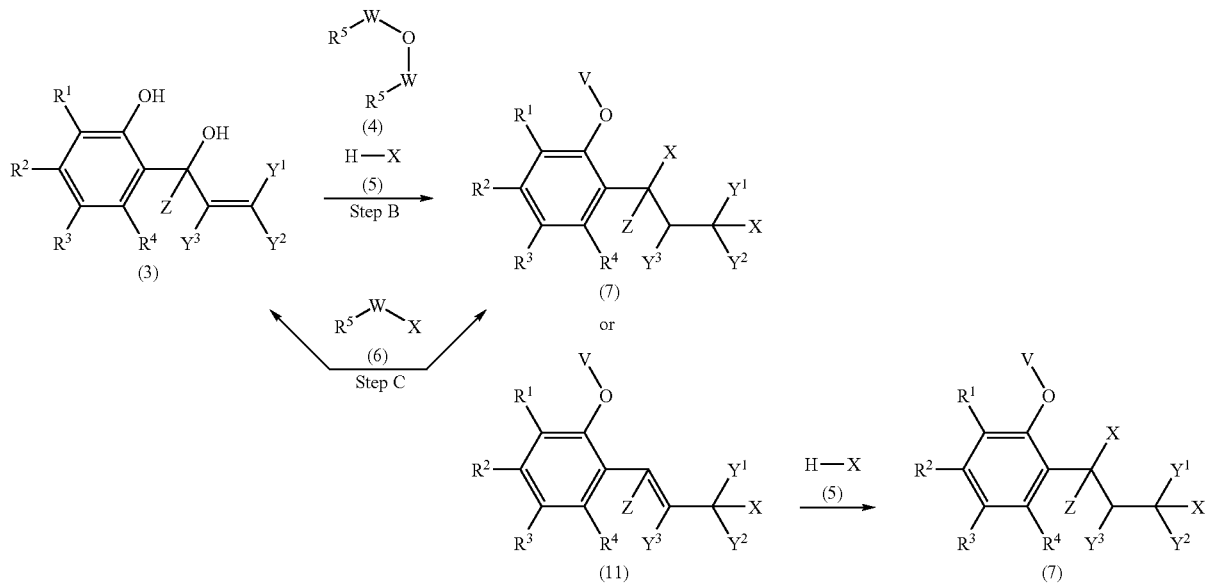

The amount of the base to be used is usually 1 to 20 mol, preferably 1.1 to 5 mol based on 1 mol of cyclopropylphenyl ester derivatives (9).

The acid used in this step is not particularly limited provided it hydrolyzes ester, examples of which include mineral acid such as hydrofluoric acid, hydrochloric acid, hydrobromic acid, hydroiodic acid, sulfuric acid, phosphoric acid; organic acid such as formic acid, acetic acid, propionic acid, trifluoroacetic acid, methanesulfonic acid, benzenesulfonic acid, more preferably hydrochloric acid.

The amount of the acid to be used is usually 1 to 20 mol, preferably 1.1 to 5 mol based on 1 mol of cyclopropylphenyl ester derivatives (9).

The reaction temperature varies depending on the raw material compound, reaction reagents, solvents and the like and is usually 0° C. to 200° C., preferably 0° C. to 50° C.

The solvent used in this step is not particularly limited provided it does not inhibit reactions, examples of which include alcohols such as methanol, ethanol, propanol; water; ethers such as dioxane, tetrahydrofuran, ethylene glycol dimethyl ether; ketones such as acetone, methyl ethyl ketone, This step is a step to produce a compound of general formula (7) by addition of hydrogen halide (5) to a compound of general formula (11), which is produced by Step B or Step C, and the addition is carried out by reacting a compound of general formula (11) with hydrogen halide (5).

Hydrogen halide (5) used in this step is not particularly limited provided it reacts with double bond to add halogen and hydrogen atom, examples of which include hydrogen fluoride, hydrogen chloride, hydrogen bromide, or hydrogen iodide, preferably hydrogen chloride, hydrogen bromide, more preferably hydrogen bromide.

The amount of hydrogen halide (5) to be used in this step is usually 1 to 100 mol, preferably 2 to 30 mol based on 1 mol of a compound (11).

The solvent used in this step is not particularly limited provided it does not inhibit reactions, examples of which include hydrocarbons such as heptane, hexane, cycloheptane, cyclohexane; aromatic hydrocarbons such as benzene, toluene, xylene; halogenated hydrocarbons such as dichloromethane, dichloroethane, chloroform, tetrachloroethane; ethers such as dioxane, diethyl ether, tetrahydrofuran (THF), ethyleneglycol dimethyl ether; esters such as methyl acetate, ethyl acetate, propyl acetate; organic acids such as formic acid, acetic acid, propionic acid, trifluoroacetic acid, difluoroacetic acid, methanesulfonic acid, trifluoromethanesulfonic acid; or mixture solvent thereof, preferably organic acids, and more preferably acetic acid.

The reaction temperature varies depending on the raw material compounds, reaction reagents, solvents and the like, and is usually 0° C. to 200° C., preferably 20° C. to 80° C.

The reaction time varies depending on the raw material compounds, reaction reagents, solvents, reaction temperature and the like and is usually 1 hours to 100 hours, preferably 2 hours to 24 hours.

The following provides a specific explanation of the present invention by examples. This invention is, however, not limited by these examples.

EXAMPLES

Example 1

2-(1-Hydroxyl-2-propenyl)-6-methylphenol

A 1 L four-necked round-bottomed flask was equipped with a magnetic stirrer bar, a thermometer and a pressure-equalizing dropping funnel. A 2-hydroxy-3-methylbenzaldehyde (30.0 g, 0.22 mol) and THF (300 ml) were added to it under a nitrogen atmosphere. After the mixture was cooled to 0° C., a solution of vinyl magnesium chloride in THF (1.9 M, 237 ml, 0.45 mol) was added thereto over 45 minutes while maintaining the mixture temperature of 15° C. or less. The mixture was gradually warmed to room temperature and stirred at room temperature for 18 hours. The mixture was cooled to 0° C. and a 20% aqueous ammonium chloride solution (600 ml) was added thereto at 0° C. After the mixture was stirred at room temperature for 30 minutes, the mixture was poured into water (500 ml). The mixture was extracted with ethyl acetate (3×500 ml). The organic layer was combined and successively washed with a 20% aqueous ammonium chloride solution (300 ml), water (2×300 ml) and a saturated aqueous NaCl solution (300 ml), followed by drying with anhydrous sodium sulfate (150 g). The solid was removed by filtration and the filtrate was concentrated to obtain 34.3 g of 2-(1-hydroxy-2-propenyl)-6-methylphenol as a brown gum.

$^1$H-NMR (500 MHz, CDCl$_3$)•ppm: 7.83 (1H, br-s), 7.06 (1H, d, J=7.1 Hz), 6.83 (1H, d, J=7.7 Hz), 6.75 (1H, t, J=7.4 Hz), 6.15 (1H, did, J=17, 9.9, and 6.0 Hz), 5.32-5.29 (2H, m), 5.22 (1H, d, J=9.9 Hz), 2.23 (3H, s).

Example 2

2-(1,3-Dibromopropyl)-6-methylphenyl acetate

A 1 L four-necked round-bottomed flask was equipped with a magnetic stirrer bar, a thermometer, a pressure-equalizing dropping funnel, a reflux condenser and a drying tube. A 25% hydrogen bromide-acetic acid solution (155 ml, 0.610 mol) and acetic anhydride (34.6 ml, 0.366 mol) were added to it. A solution of 2-(1-hydroxyallyl)-6-methylphenol (20.0 g, 0.122 mol) in acetic acid (30 ml) was added to the pressure-equalizing dropping funnel and added thereto over 4 minutes such that the temperature of the mixture did not exceed 43° C. After the mixture was stirred at room temperature for 2 hours, it was stirred at 50° C. for 4 hours. The mixture was cooled to room temperature and poured into water (1 L) such that the temperature did not exceed 23° C. The obtained mixture was extracted with a 10% ethyl acetate-90% hexane (V/V) solvent mixture (3×500 ml). The organic layer was combined and it was successively washed with water (4×800 ml) and a saturated aqueous NaCl solution (500 ml), followed by drying with anhydrous sodium sulfate (350 g). The solid was removed by filtration and the filtrate was concentrated to obtain 37.3 g of 2-(1,3-dibromopropyl)-6-methylphenyl acetate as a dark brown gum.

$^1$H-NMR (500 MHz, CDCl$_3$)•ppm: 7.41-7.38 (1H, m), 7.22-7.17 (2H, m), 5.35 (1H, dd, J=4.8 and 4.8 Hz), 3.60 (1H, td, J=9.8, 4.8 Hz), 3.49 (1H, quintet, J=4.8 Hz), 2.69 (1H, qd, J=9.6, 4.9 Hz), 2.48 (1H, qd, J=9.7, 4.9 Hz), 2.40 (3H, s), 2.17 (3H, s).

Example 3

2-Cyclopropyl-6-methylphenyl acetate

A 500 ml four-necked round-bottomed flask was equipped with a magnetic stirrer bar, a thermometer, a reflux condenser and a drying tube. Magnesium (2.50 g, 102.8 mmol) and anhydrous THF (30 ml) were added thereto under a nitrogen atmosphere. Iodine (63 mg) was added to the mixture and the mixture was stirred at room temperature for 30 minutes. Subsequently, 2-(1,3-dibromopropyl)-6-methylphenyl acetate (30.0 g, 85.7 mmol) and anhydrous THF (90 ml) were added to the mixture at 80° C. over 15 minutes. After the mixture was stirred at 80° C. for 30 minutes, the mixture was further stirred at room temperature for 1.5 hours. 1M Hydrochloric acid (100 ml) was added dropwise to the reaction mixture such that the temperature of the reaction mixture did not exceed 40° C. The mixture was diluted with water (100 ml) and extracted with a 10% ethyl acetate-90% hexane (V/V) solvent mixture (3×200 ml). The organic layer was combined and it was successively washed with water (2×200 ml) and a saturated aqueous NaCl solution (50 ml), followed by drying with anhydrous sodium sulfate (100 g). After the solid was removed by filtration, the filtrate was concentrated to obtain 18.5 g of 2-cyclopropyl-6-methylphenyl acetate as a brown gum.

$^1$H-NMR (500 MHz, CDCl$_3$)•ppm: 7.07-7.04 (2H, m), 6.86-6.83 (1H, m), 2.36 (3H, s), 2.17 (3H, s), 1.85-1.79 (1H, m), 0.87 (2H, dd, J=8.8, 1.6 Hz), 0.63 (2H, d, J=4.9 Hz).

Example 4

2-Cyclopropyl-6-methylphenol

A 500 ml three-necked round-bottomed flask was equipped with a magnetic stirrer bar, a thermometer and a drying tube. A solution of 2-cyclopropyl-6-methylphenyl acetate (18.3 g, 96.2 mmol) in methanol (100 ml) was added thereto. Potassium carbonate (26.5 g, 192 mmol) was added thereto at once and the mixture was stirred at room temperature for 75 minutes. After water (300 ml) was added to the reaction mixture, the resulting mixture was concentrated by an evaporator to remove most of methanol. The obtained mixture was cooled to 0° C. and 4M hydrochloric acid (100 ml) was added thereto such that the temperature of the mixture did not exceed 25° C. This was extracted with a 10% ethyl acetate-90% hexane (V/V) solvent mixture (3×200 ml). The organic layer was combined and successively washed with water (2×200 ml) and a saturated aqueous NaCl solution (50 ml), followed by drying with anhydrous sodium sulfate (90 g). After the solid was removed by filtration and the filtrate was concentrated to obtain 13.8 g of a crude product of 2-cyclopropyl-6-methylphenol as a brown oil. The crude product was distilled (7.6-7.8 mmHg, 94-98° C.) to obtain 9.64 g of 2-cyclopropyl-6-methylphenol as a light purple oil.

$^1$H-NMR (500 MHz, CDCl$_3$)•ppm: 7.00 (1H, d, J=7.1 Hz), 6.94 (1H, d, J=7.1 Hz), 6.75 (1H, t, J=7.4 Hz), 5.55 (1H, s), 2.26 (3H, s), 1.80-1.74 (1H, m), 0.96 (2H, ddd, J=9.1, 4.9, 3.3 Hz), 0.63 (2H, td, J=5.5, 3.8 Hz).

Example 5

2-(1,3-dibromopropyl)-6-methylphenyl acetate

A 5 ml pear shaped flask was equipped with a magnetic stirrer bar and a drying tube. 2-(1-Hydroxyallyl)-6-methylphenol (41 mg, 0.25 mmol) and acetic acid (0.6 ml) were added thereto and acetyl bromide (55 µl, 0.74 mmol) was added thereto with stirring. After the mixture was stirred at room temperature for 3 hours, it was concentrated. The obtained residue (70 mg) was purified by preparative thin layer chromatography (manufactured by MERCK, 1.05744, development by ethyl acetate:hexane=9:1) to obtain 35.8 mg of 2-(1,3-dibromopropyl)-6-methylphenyl acetate and 16.2 mg of 2-(3-bromo-1-propenyl)-6-methylphenyl acetate. 2-(3-bromo-1-propenyl)-6-methylphenyl acetate.

$^1$H-NMR (500 MHz, CDCl$_3$)•ppm: 7.37-7.35 (1H, m), 7.20-7.11 (2H, m), 6.61 (1H, d, J=15.8 Hz), 6.41-6.34 (1H, m), 4.13 (2H, d, J=7.6 Hz), 2.37 (3H, s), 2.16 (3H, s).

Example 6

2-Fluoro-6-(1-hydroxy-2-propenyl)phenol

After a solution of 3-fluoro-2-hydroxybenzaldehyde (600 mg, 4.28 mmol) in THF (10 ml) was cooled to 0° C., a solution of vinyl magnesium chloride in THF (1.9M, 5.42 ml, 10.3 mmol) was added thereto over 5 minutes. The mixture was gradually warmed to room temperature and stirred at room temperature overnight. The mixture was cooled to 0° C. and a saturated aqueous ammonium chloride solution was added thereto at 0° C. The mixture was extracted with ethyl acetate. The organic layer was combined and successively washed with water and a saturated aqueous NaCl solution, followed by drying with anhydrous sodium sulfate. The solid was removed by filtration and the filtrate was concentrated to obtain 772 mg of 2-fluoro-6-(1-hydroxy-2-propenyl)phenol as a pale yellow oil.

$^1$H-NMR (500 MHz, CDCl$_3$)•ppm: 7.16 (1H, s), 7.01 (1H, ddd, J=10.4, 8.2, and 1.6 Hz), 6.88 (1H, d, J=7.7 Hz), 6.80 (1H, td, J=7.7 and 4.9 Hz), 6.12 (1H, ddd, J=17.6, 10.4, and 6.0 Hz), 5.44 (1H, d, J=4.4 Hz), 5.35 (1H, dt, J=17.6 and 1.1 Hz), 5.26 (1H, dd, J=10.4 and 1.1 Hz), 2.77 (1H, d, J=3.2 Hz).

Example 7

2-(1,3-Dibromopropyl)-6-fluorophenyl acetate

Acetic anhydride (1.21 ml, 12.8 mmol) was added to a 25% hydrogen bromide-acetic acid solution (5.74 ml, 21.4 mmol). A solution of 2-fluoro-6-(1-hydroxy-2-propenyl)phenol (772 mg, 4.28 mmol) in acetic acid (0.4 ml) was added thereto at room temperature. The mixture was stirred at 50° C. for 6 hours. The mixture was cooled to room temperature and poured into water (100 ml). The obtained mixture was extracted with a 10% ethyl acetate-90% hexane (V/V) solvent mixture (50 ml). The organic layer was successively washed with water (4×50 ml) and a saturated aqueous NaCl solution (30 ml) and dried with anhydrous sodium sulfate. The solid was removed by filtration and the filtrate was concentrated to obtain 1.17 g of 2-(1,3-dibromopropyl)-6-fluorophenyl acetate as a dark brown oil.

$^1$H-NMR (500 MHz, CDCl$_3$)•ppm: 7.32 (1H, d, J=7.7 Hz), 7.24 (1H, td, J=8.2 and 4.9 Hz), 7.13 (1H, ddd, J=9.9, 8.2, and 1.1 Hz), 5.37 (1H, dd, J=8.8 and 4.9 Hz), 3.59 (1H, ddd, J=10.4, 8.8, and 4.9 Hz), 3.47 (1H, quintet, J=5.5 Hz), 2.71 (1H, qd, J=9.9 and 4.9 Hz), 2.53-2.46 (1H, m), 2.41 (3H, s).

Example 8

2-Cyclopropyl-6-fluorophenyl acetate

Iodine (catalytic amount) was added to a mixture of magnesium (95.2 mg, 3.96 mmol) and anhydrous THF (2 ml) under a nitrogen atmosphere and the mixture was stirred at room temperature for 30 minutes. Subsequently, a solution of 2-(1,3-dibromopropyl)-6-fluorophenyl acetate (1.17 g, 3.30 mmol) in anhydrous THF (6 ml) was added to the mixture over 10 minutes at 80° C. After the mixture was stirred at 80° C. for 1 hour, the mixture was further stirred at room temperature for 1 hour. The reaction mixture was ice-cooled and 1M hydrochloric acid (15 ml) was added thereto. The mixture was stirred at room temperature for 1 hour and extracted with a 10% ethyl acetate-90% hexane (V/V) solvent mixture (2×20 ml). The organic layer was combined and successively washed with water (3×20 ml) and a saturated aqueous NaCl solution (20 ml), followed by drying with anhydrous sodium sulfate. After the solid was removed by filtration, the filtrate was concentrated to obtain 645 mg of 2-cyclopropyl-6-fluorophenyl acetate as a brown oil.

$^1$H-NMR (500 MHz, CDCl$_3$)•ppm: 7.09 (1H, td, J=8.2 and 5.4 Hz), 6.96 (1H, td, J=8.2 and 1.6 Hz), 6.72 (1H, d, J=8.2 Hz), 2.38 (3H, s), 1.91-1.86 (1H, m), 0.94 (2H, ddd, J=8.2, 6.6, 4.9 Hz), 0.67 (2H, dt, J=6.6 and 4.9 Hz).

Example 9

2-Cyclopropyl-6-fluorophenol

Potassium carbonate (911 mg, 6.60 mmol) was added to a solution of 2-cyclopropyl-6-fluorophenyl acetate (640 mg, 3.30 mmol) in methanol (4 ml), and the mixture was stirred at room temperature for 1 hour. After 1M hydrochloric acid was added to the reaction mixture to adjust pH to 2, this was extracted with acetic acid. The organic layer was combined and washed with a saturated aqueous NaCl solution, followed by drying with anhydrous sodium sulfate. After the solid was removed by filtration, the filtrate was concentrated to obtain 497 mg of 2-cyclopropyl-6-fluorophenol.

$^1$H-NMR (500 MHz, CDCl$_3$)•ppm: 6.92-6.88 (1H, m), 6.74 (1H, td, J=8.2 and 5.4 Hz), 6.67 (1H, d, J=8.2 Hz), 5.32 (1H, d, J=3.8 Hz), 2.09-2.03 (1H, m), 0.98 (2H, ddd, J=8.8, 6.0, 4.4 Hz), 0.69 (2H, td, J=6.0 and 4.4 Hz).

Example 10

2-Chloro-6-(1-hydroxy-2-propenyl)phenol

After a solution of 3-chloro-2-hydroxybenzaldehyde (15.4 g, 98 mmol) in THF (100 ml) was cooled to 0° C., a solution of vinyl magnesium chloride in THF (1.9M, 126 ml, 240 mmol) was added thereto over 40 minutes. The mixture was gradually warmed to room temperature and stirred at room temperature for 14 hours. The mixture was cooled to 0° C. and a 20% aqueous ammonium chloride solution (200 ml) was added thereto at 0° C. The mixture was extracted with ethyl acetate. The organic layer was combined and successively washed with water and a saturated aqueous NaCl solution, followed by drying with anhydrous sodium sulfate. The solid was removed by filtration and the filtrate was concentrated to obtain a brown oil. This oil was purified by silica gel column chromatography (elution with hexane:ethyl acetate=5:1) to obtain 15.1 g of 2-chloro-6-(1-hydroxy-2-propenyl)phenol as a pale brown oil. $^1$H-NMR (500 MHz, CDCl$_3$)•ppm: 7.28 (1H, dd, J=7.7 and 1.1 Hz), 7.16 (1H, s), 7.08 (1H, dd, J=7.7 and 1.1 Hz), 6.84 (1H, t, J=7.7 Hz), 6.12 (1H, ddd, J=17.0, 10.4, and 6.0 Hz), 5.44 (1H, d, J=4.4 Hz), 5.36 (1H, dt, J=17.0 and 1.1 Hz), 5.26 (1H, dt, J=10.4 and 1.1 Hz), 2.63 (1H, d, J=3.3 Hz).

Example 11

2-Chloro-6-(1,3-dibromopropyl)phenyl acetate

A solution of 2-chloro-6-(1-hydroxy-2-propenyl)phenol (15.1 g, 82 mmol) in acetic acid (5 ml) was added to a mixture of a 30% hydrogen bromide-acetic acid solution (81.7 ml, 410 mmol) and acetic anhydride (23.3 ml, 246 mmol) over 15 minutes such that the temperature of the mixture did not exceed 43° C. After the mixture was stirred at room temperature for 30 minutes, it was stirred at 52° C. for 9 hours and at room temperature for 15 hours. The reaction mixture was poured to water (500 ml) over 10 minutes and the obtained mixture was extracted with a 10% ethyl acetate-90% hexane (V/V) solvent mixture (3×200 ml). The organic layer was combined and washed with water (4×500 ml), followed by drying with anhydrous sodium sulfate. The solid was removed by filtration and the filtrate was concentrated to obtain 28.5 g of 2-chloro-6-(1,3-dibromopropyl)phenyl acetate as a pale brown oil.

$^1$H-NMR (500 MHz, CDCl$_3$)•ppm: 7.48 (1H, dd, J=7.7 and 1.1 Hz), 7.41 (1H, dd, J=7.7 and 1.1 Hz), 7.24 (1H, t, J=7.7 Hz), 5.34 (1H, dd, J=9.3 and 4.9 Hz), 3.60 (1H, td, J=9.9, 4.4 Hz), 3.49 (1H, quintet, J=4.9 Hz), 2.67 (1H, dq, J=9.9, 4.9 Hz), 2.45 (1H, dq, J=9.9, 4.9 Hz), 2.42 (3H, s).

Example 12

2-Chloro-6-cyclopropylphenyl acetate

Iodine (catalytic amount) was added to a mixture of magnesium (1.97 g, 81 mmol) and anhydrous THF (30 ml) under a nitrogen atmosphere, and the mixture was stirred at room temperature for 30 minutes. Subsequently, a solution of 2-chloro-6-(1,3-dibromopropyl)phenyl acetate (28.5 g, 77 mmol) in anhydrous THF (90 ml) was added to the mixture at 80° C. over 45 minutes. After the mixture was stirred at 80° C. for 1 hour, the mixture was further stirred at room temperature for 2 hours. The reaction mixture was ice-cooled and 1M hydrochloric acid (80 ml) was added thereto. The mixture was extracted with ethyl acetate (2×100 ml). The organic layer was combined and successively washed with water and a saturated aqueous NaCl solution, followed by drying with anhydrous sodium sulfate. After the solid was removed by filtration, the filtrate was concentrated to obtain 16.3 g of 2-chloro-6-cyclopropylphenyl acetate as a brown oil.

$^1$H-NMR (500 MHz, CDCl$_3$)•ppm: 7.25 (1H, dd, J=7.7 and 1.1 Hz), 7.09 (1H, t, J=7.7 Hz), 6.88 (1H, dd, J=7.7 and 1.1 Hz), 2.39 (3H, s), 1.87 (1H, tt, J=8.2 and 5.0 Hz), 0.93 (2H, ddd, J=8.2, 6.0, and 4.4 Hz), 0.63 (2H, q, J=5.5 Hz).

Example 13

2-Chloro-6-cyclopropylphenol

Potassium carbonate (21.3 g, 154 mmol) was added to a solution of 2-chloro-6-cyclopropylphenyl acetate (16.3 g, 77 mmol) in methanol (80 ml) at once and the mixture was stirred at room temperature for 90 minutes. After water (240 ml) was added to the reaction mixture, the resulting mixture was concentrated by an evaporator to remove most of methanol. The obtained mixture was cooled to 0° C. and 4M hydrochloric acid was added thereto to make pH to 2 or lower such that the temperature of the mixture did not exceed 25° C. This was extracted with a 10% ethyl acetate-90% hexane (V/V) solvent mixture. The organic layer was combined and washed with a saturated aqueous NaCl solution, followed by drying with anhydrous sodium sulfate (90 g). After the solid was removed by filtration, the filtrate was concentrated to obtain a pale brown oil. This oil was purified by silica gel column chromatography (use of 120 g of Wakogel C-100E) to obtain 10.1 g of 2-chloro-6-cyclopropylphenol.

$^1$H-NMR (500 MHz, CDCl$_3$)•ppm: 7.14 (1H, dd, J=7.7 and 1.6 Hz), 6.80 (1H, dd, J=7.7 and 1.1 Hz), 6.77 (1H, t, J=7.7 Hz), 5.72 (1H, s), 2.08 (1H, tt, J=8.2 and 4.9 Hz), 0.97 (2H, ddd, J=8.2, 6.0, and 4.4 Hz), 0.67 (2H, ddd, J=6.0, 5.5 and 4.4 Hz).

Example 14

2-Bromo-6-(1-hydroxy-2-propenyl)phenol

After a solution of 3-bromo-2-hydroxybenzaldehyde (1.35 g, 6.7 mmol) in THF (10 ml) was cooled to 0° C., a solution of vinyl magnesium chloride in THF (2.0M, 8.05 ml, 16.1 mmol) was added thereto under a nitrogen atmosphere over 5 minutes. The mixture was gradually warmed to room temperature and stirred at room temperature for 3 hours. The mixture was cooled to 0° C. and a 20% aqueous ammonium chloride solution (30 ml) was added thereto at 0° C. After the mixture was stirred at room temperature for 30 minutes, it was poured to ice-water (30 ml). The mixture was extracted with ethyl acetate (2×50 ml). The organic layer was combined and successively washed with water (30 ml) and a saturated aqueous NaCl solution (30 ml), followed by drying with anhydrous sodium sulfate. The solid was removed by filtration and the filtrate was concentrated to obtain a pale brown oil. This oil was purified by silica gel column chromatography (use of 40 g of Wakogel C-100E, elution with hexane:ethyl acetate=5:1) to obtain 1.24 g of 2-bromo-6-(1-hydroxy-2-propenyl)phenol.

$^1$H-NMR (500 MHz, CDCl$_3$)•ppm: 7.43 (1H, dd, J=7.7 and 1.1 Hz), 7.32 (1H, s), 7.10 (1H, dd, J=7.7 and 1.1 Hz), 6.78 (1H, t, J=7.7 Hz), 6.11 (1H, ddd, J=17.0, 10.4, and 6.0 Hz), 5.42 (1H, dd, J=5.5 and 4.5 Hz), 5.36 (1H, dt, J=17.0 and 1.1 Hz), 5.25 (1H, dt, J=10.4 and 1.1 Hz), 2.72-2.71 (1H, m).

Example 15

2-Bromo-6-(1,3-dibromopropyl)phenyl acetate

A solution of 2-bromo-6-(1-hydroxy-2-propenyl)phenol (1.20 g, 5.24 mmol) in acetic acid (1 ml) was added to a mixture of 25% hydrogen bromide-acetic acid solution (6.60 ml, 26.2 mmol) and acetic anhydride (1.48 ml, 15.7 mmol) at room temperature. After the mixture was stirred at room temperature for 15 minutes, it was stirred at 50° C. for 5 hours. The mixture was cooled to room temperature and poured to water (50 ml). The obtained mixture was extracted with a 10% ethyl acetate-90% hexane (V/V) solvent mixture (2×50 ml). The organic layer was combined and successively washed with water (40 ml) and a saturated aqueous NaCl solution, followed by drying with anhydrous sodium sulfate. The solid was removed by filtration and the filtrate was concentrated to obtain 1.89 g of residue. This residue was purified by silica gel column chromatography (Wakogel C-100E, elution with hexane:ethyl acetate=20:1) to obtain 1.24 g of 2-bromo-6-(1,3-dibromopropyl)phenyl acetate.

$^1$H-NMR (500 MHz, CDCl$_3$)•ppm: 7.57 (1H, dd, J=7.7 and 1.1 Hz), 7.54 (1H, dd, J=7.7 and 1.1 Hz), 7.18 (1H, t, J=7.7 Hz), 5.34 (1H, dd, J=9.9 and 4.4 Hz), 3.60 (1H, td, J=10.4, 4.4 Hz), 3.50 (1H, quintet, J=4.9 Hz), 2.65 (1H, dq, J=9.9, 4.9 Hz), 2.45 (1H, dq, J=9.3, 4.9 Hz), 2.42 (3H, s).

Example 16

2-Bromo-6-cyclopropylphenyl acetate

Iodine (catalytic amount) was added to a mixture of magnesium (75.5 mg, 3.14 mmol) and anhydrous THF (1.5 ml) under a nitrogen atmosphere, and the mixture was stirred at room temperature for 30 minutes. Subsequently, a solution of 2-bromo-6-(1,3-dibromopropyl)phenyl acetate (1.24 g, 2.99 mmol) in anhydrous THF (4.5 ml) was added to the mixture at 80° C. over 2 minutes. After the mixture was stirred at 80° C. for 1 hour and 30 minutes, the mixture was further stirred at room temperature for 2 hours. The reaction mixture was ice-cooled and 1M hydrochloric acid was added thereto to make pH to 2 or lower. The mixture was extracted with ethyl acetate. The organic layer was combined and successively washed with water and a saturated aqueous NaCl solution, followed by drying with anhydrous sodium sulfate. After the solid was removed by filtration, the filtrate was concentrated to obtain a residue. This residue was purified by silica gel column chromatography to obtain 316 mg of 2-bromo-6-cyclopropylphenyl acetate.

$^1$H-NMR (500 MHz, CDCl$_3$)•ppm: 7.41 (1H, dd, J=7.7 and 1.1 Hz), 7.03 (1H, t, J=7.7 Hz), 6.93 (1H, dd, J=7.7 and 1.1 Hz), 2.39 (3H, s), 1.87 (1H, tt, J=8.2 and 4.9 Hz), 0.92 (2H, dd, J=8.8, and 1.6 Hz), 0.66 (2H, q, J=5.5 Hz).

Example 17

2-Bromo-6-cyclopropylphenol

Potassium carbonate (276 mg, 2.00 mmol) was added to a solution of 2-bromo-6-cyclopropylphenyl acetate (316 mg, purity: 80%, 1.00 mmol) in methanol (2 ml), and the mixture was stirred at room temperature for 4 hours. After water (15 ml) and 4M hydrochloric acid (15 ml) were added to the reaction mixture, the mixture was extracted with ethyl acetate. The organic layer was combined, washed with a saturated aqueous NaCl solution, followed by drying with anhydrous sodium sulfate. After the solid was removed by filtration, the filtrate was concentrated to obtain a pale brown oil. This oil was purified by preparative thin layer chromatography (manufactured by Merck Co., Ltd, 1.05744, use of two sheets, development by hexane:ethyl acetate=30:1) to obtain 118 mg of 2-bromo-6-cyclopropylphenol.

$^1$H-NMR (500 MHz, CDCl$_3$)•ppm: 7.29 (1H, dd, J=7.7 and 1.6 Hz), 6.85 (1H, t, J=7.7 Hz), 6.78 (1H, dd, J=7.7 and 1.1 Hz), 5.72 (1H, s), 2.09 (1H, tt, J=8.2 and 5.0 Hz), 0.97 (2H, ddd, J=8.2, 6.0, and 4.4 Hz), 0.67 (2H, ddd, J=6.0, 5.5 and 4.4 Hz).

Example 18

2-(1,3-Dibromopropyl)-6-methylphenyl acetate

A mixture of 2-(1,3-dibromopropyl)-6-methylphenyl acetate and 2-(3-bromo-1-propenyl)-6-methylphenyl acetate {970 mg, molar ratio=4:1, 2-(1,3-dibromopropyl)-6-methylphenyl acetate=2.32 mmol, 2-(3-bromo-1-propenyl)-6-methylphenyl acetate=0.58 mmol} was mixed with a 25% hydrogen bromide-acetic acid solution (3.7 ml, 14.5 mmol), and the mixture was stirred at room temperature overnight. The reaction mixture was concentrated and the residue was dissolved in ethyl acetate (50 ml). This solution was successively washed with water (3×30 ml) and a saturated aqueous NaCl solution (30 ml) and dried with anhydrous sodium sulfate. The solid was removed by filtration and the filtrate was concentrated to obtain 970 mg of a crude product of 2-(1,3-dibromopropyl)-6-methylphenyl acetate as a dark brown oil.

Example 19

2-(1-Hydroxyl-2-propenyl)-6-methylphenol

2-Hydroxy-3-methylbenzaldehyde (48.78 g, purity: 40.7%, 0.146 mol) was dissolved in toluene (100 ml), and the mixture was added to a reactor under a nitrogen atmosphere. After the mixture was cooled to 0° C. in ice-water, a solution of vinyl magnesium chloride in THF-toluene (1.77M, 182 ml, 0.32 mol, THF:toluene=1:1 (v:v)) was added thereto over 15 minutes such that the temperature of the mixture did not exceed 25° C. After the mixture was stirred at 15-20° C. for 2 hours, it was cooled to 0° C. A 20% aqueous ammonium chloride solution (250 ml) was added thereto. After the mixture was stirred at 25° C. for 1 hour, the solution was separated. The organic layer was concentrated to obtain 32.36 g (purity: 73.5%, 0.145 mol) of 2-(1-hydroxy-2-propenyl)-6-methylphenol as an orange-colored oil.

Example 20

2-(1,3-Dibromopropyl)-6-methylphenyl acetate

A 500 ml three-necked round-bottomed flask was equipped with a magnetic stirrer bar, a thermometer, a pressure-equalizing dropping funnel and a reflux condenser. A drying tube was mounted on the top of the reflux condenser. A 30% hydrogen bromide-acetic acid solution (48.4 ml, 0.247 mol) and acetic anhydride (14.0 ml, 0.148 mol) were added thereto. A solution of 2-(1-hydroxyallyl)-6-methylphenol (11.0 g, purity: 73.5%, 0.0493 mol) in toluene (20 ml) was added to the pressure-equalizing dropping funnel, and added to the flask over 20 minutes such that the temperature of the mixture did not exceed 35° C. The pressure-equalizing dropping funnel was removed and the mixture was stirred at 50-55° C. for 6.5 hours. The mixture was cooled in ice-water (temperature of the mixture was 0-2° C.) and an aqueous 4M NaOH solution (185 ml, 0.741 mol) was added thereto over 20 minutes such that the temperature did not exceed 40° C. The obtained mixture was stirred at 20° C. for 1 hour and extracted with toluene (100 ml). After the organic layer was washed with water (100 ml), it was concentrated to obtain 18.0 g (purity: 67%, 0.0343 mol) of 2-(1,3-dibromopropyl)-6-methylphenyl acetate as a dark brown oil.

Example 21

2-Cyclopropyl-6-methylphenyl acetate

A 300 ml four-necked round-bottomed flask was equipped with a magnetic stirrer bar, a thermometer, a reflux condenser and a drying tube. Magnesium (1.50 g, 61.7 mmol), toluene (15 ml) and anhydrous THF (15 ml) were added to the flask under a nitrogen atmosphere. The mixture was heated in an oil bath of 75° C. for 15 minutes (temperature of the mixture was 62-64° C.). Subsequently, the mixture was heated in an oil bath of 75° C. and a solution of 2-(1,3-dibromopropyl)-6-methylphenyl acetate (17.9 g, purity: 67%, 34.3 mmol) in toluene (60 ml) was added thereto over 30 minutes. The temperature of the mixture was raised to 89° C. After the mixture was stirred in an oil bath of 75° C. for 5.5 hours, the mixture was cooled and 6M hydrochloric acid (20.5 ml, 123 mmol) was added dropwise thereto over 15 minutes such that the temperature of the reaction mixture did not exceed 45° C. After the mixture was stirred at room temperature for 1 hour, it was diluted with water (20 ml) and it was stirred for 10 minutes. The solution was separated and the organic layer was successively washed with a saturated aqueous NaHCO$_3$ solution (50 ml) and water (50 ml) and concentrated to obtain 11.1 g (purity: 45.2%, 26.4 mmol) of 2-cyclopropyl-6-methylphenyl acetate as a brown gum.

Example 22

2-Cyclopropyl-6-methylphenol

A 200 ml four-necked round-bottomed flask was equipped with a magnetic stirrer bar, a thermometer and a drying tube. Magnesium (498 mg, 20.5 mmol) and anhydrous THF (7 ml) were added thereto under a nitrogen atmosphere. The mixture was heated in an oil bath of 75° C. for 15 minutes (temperature of the mixture was 62-64° C.). Subsequently, the mixture was heated in an oil bath of 75° C. and a solution of 2-(1,3-dibromopropyl)-6-methylphenyl acetate (6.00 g, 17.1 mmol or less) in THF (21 ml) was added thereto over 20 minutes. The temperature of the mixture was raised to 70° C. After the mixture was stirred in an oil bath of 75° C. for 3 hours, the mixture was cooled and 6M hydrochloric acid (7.13 ml, 42.8 mmol) was added thereto over 5 minutes. After the mixture was stirred at room temperature for 1 hour, it was transferred to a 200 ml round bottom flask and most of THF was distilled off under reduced pressure. Methanol (15 ml) was added to the residue and the obtained mixture was stirred under heating at reflux for 9 hours. The mixture was cooled and methanol was distilled off under reduced pressure. Water (8 ml) was added to the residue and it was extracted with toluene (25 ml and 15 ml). The organic layer was combined and washed with water (20 ml), followed by concentration to obtain 2.69 g of a crude product of 2-cyclopropyl-6-methylphenol.

Example 23

2-Cyclopropyl-6-methylphenol

A magnetic stirrer bar was attached to a 1 L round bottom flask. 2-Cyclopropyl-6-methylphenyl acetate (32.5 g), methanol (90 ml) and an aqueous 4M NaOH solution (90 ml) were added thereto, and the mixture was stirred at room temperature for 2 hours. After most of methanol was removed by concentration, the obtained mixture was cooled in ice-water and water (500 ml) and 4M hydrochloric acid (120 ml) were added thereto, followed by stirring of the mixture. This was extracted with a 10% ethyl acetate-90% hexane (V/V) solvent mixture (3×200 ml). The organic layer was combined and successively washed with water (3×200 ml) and a saturated aqueous NaCl solution (200 ml), followed by drying with anhydrous sodium sulfate. After the solid was removed by filtration, the filtrate was concentrated to obtain 27.09 g (purity: 54.6%) of a crude product of 2-cyclopropyl-6-methylphenol.

UTILIZABILITY IN INDUSTRY

According to the present invention, the cyclopropylphenol derivative can be stably prepared at a low cost and at a high yield using a carbonyl derivative as a raw material. Its utilization value is high as a process for preparing the cyclopropylphenols useful as a raw material of a pharmaceutical/agrochemicals and functional materials.

The invention claimed is:

1. A process for producing a cyclopropylphenol derivative represented by general formula (10):

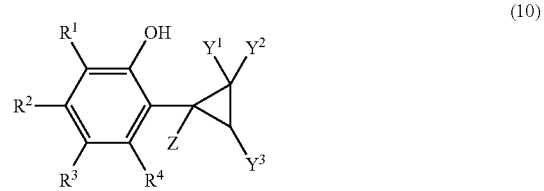

(10)

[wherein R$^1$, R$^2$, R$^3$ and R$^4$ each independently represent a hydrogen atom, halogen atom, optionally substituted C$_1$-C$_6$ alkyl group (wherein said substituent is a substituent selected from the following substituent group B), optionally substituted C$_2$-C$_6$ alkenyl group (wherein said substituent is a cyano group or nitro group), C$_2$-C$_6$ alkynyl group, optionally substituted C$_3$-C$_6$ cycloalkyl group (wherein said substituent is a substituent selected from the following substituent group C), C$_4$-C$_{10}$ bicycloalkyl group, cyano group, formyl group, C$_2$-C$_7$ alkylcarbonyl group, optionally substituted benzoyl group (wherein said substituent is a substituent selected from the following substituent group A), carboxyl group, C$_2$-C$_7$ alkoxycarbonyl group, carbamoyl group, di(C$_1$-C$_6$ alkyl)carbamoyl group, optionally substituted phenyl group (wherein said substituent is a substituent selected from the following substituent group A), optionally substituted 3 to 6 membered heterocyclic group (wherein said heterocyclic ring contains one nitrogen atom, oxygen atom or sulfur atom therein, may further contain 1 to 2 nitrogen atoms, may be condensed with a benzene ring, and said substituent is a substituent selected from the following substituent group E), optionally substituted amino group (wherein said substituent is a substituent selected from the following substituent group D), nitro group, hydroxyl group, C$_1$-C$_6$ alkoxy group, C$_1$-C$_6$ haloalkoxy group, (C$_1$-C$_6$ alkoxy)C$_1$-C$_6$ alkoxy group, optionally substituted phenoxy group (wherein said substituent is a hydroxyl group or a pyridazinyloxy group substituted with a halogen atom and/or C$_1$-C$_6$ alkoxy group), optionally substituted 5 to 6 membered heterocylooxy group (wherein said heterocyclic ring contains one nitrogen atom, oxygen atom or sulfur atom therein, may further contain 1 to 2 nitrogen atoms, and said substituent is a substituent selected from the following substituent group E), optionally substituted C$_2$-C$_7$ alkylcarbonyloxy group (wherein said substituent is a substituent selected from the following substituent group B), optionally substituted C$_2$-C$_7$ alkoxycarbonyloxy group (wherein said substituent is a substituent selected from the following substituent group B), optionally substituted benzoyloxy group (wherein said substituent is a substituent selected from the following substituent group A), optionally substituted phenylsulfonyloxy group (wherein said substituent is a substituent selected from the following substituent group A), C$_1$-C$_6$ alkylthio group, $C_1$-$C_6$ alkylsulfinyl group, $C_1$-$C_6$ alkylsulfonyl group or tri($C_1$-$C_6$ alkyl)silyl group, or two adjacent $R^1$, $R^2$, $R^3$ and $R^4$ may together with carbon atoms respectively bonded thereto form an optionally substituted 3 to 6 membered cyclic hydrocarbon group (wherein said cyclic hydrocarbon may be interrupted by 1 to 2 same or different heteroatoms selected from the group consisting of a nitrogen atom, oxygen atom and sulfur atom, said substituent is a halogen atom, $C_1$-$C_6$ alkyl group, hydroxy $C_1$-$C_6$ alkyl group, $C_1$-$C_6$ alkoxy group, oxo group, hydroxyimino group or $C_1$-$C_6$ alkoxyimino group, and in the case the cyclic hydrocarbon is substituted with a $C_1$-$C_6$ alkyl group, a new 3-membered ring may be formed by bonding with other $C_1$-$C_6$ alkyl groups or carbon atoms on the ring);

Z represents a hydrogen atom, optionally substituted $C_1$-$C_6$ alkyl group (wherein said substituent is a substituent selected from the following substituent group B), $C_2$-$C_6$ alkenyl group, $C_2$-$C_6$ alkynyl group, optionally substituted $C_3$-$C_6$ cycloalkyl group or optionally substituted phenyl group (wherein said substituent is a substituent selected from the following substituent group A);

$Y^1$, $Y^2$ and $Y^3$ each independently represent a hydrogen atom, halogen atom, optionally substituted $C_1$-$C_6$ alkyl group (wherein said substituent is a substituent selected from the following substituent group B), optionally substituted $C_2$-$C_6$ alkenyl group (wherein said substituent is a cyano group or nitro group), alkynyl group, optionally substituted $C_3$-$C_6$ cycloalkyl group (wherein said substituent is a substituent selected from the following substituent group C), optionally substituted phenyl group (wherein said substituent is a substituent selected from the following substituent group A), nitro group, $C_1$-$C_6$ alkoxy group, $C_1$-$C_6$ haloalkoxy group, ($C_1$-$C_6$ alkoxy) $C_1$-$C_6$ alkoxy group, $C_1$-$C_5$ alkylthio group, $C_1$-$C_6$ alkylsulfinyl group or $C_1$-$C_6$ alkylsulfonyl group;

substituent group A is a group consisting of a halogen atom, $C_1$-$C_6$ alkyl group, $C_1$-$C_6$ haloalkyl group, $C_3$-$C_6$ cycloalkyl group, cyano group and tri($C_1$-$C_6$ alkyl)silyl group;

substituent group B is a group consisting of a halogen atom, $C_3$-$C_6$ cycloalkyl group, cyano group, $C_2$-$C_7$ alkylcarbonyl group, $C_2$-$C_7$ alkoxycarbonyl group, phenyl group, $C_1$-$C_6$ alkoxy group, $C_1$-$C_6$ alkylthio group, $C_1$-$C_6$ alkylsulfinyl group, $C_1$-$C_6$ alkylsulfonyl group, $C_1$-$C_4$ alkylenedioxy group, hydroxyimino group and $C_1$-$C_6$ alkoxyimino group;

substituent group C is a group consisting of a halogen atom, optionally substituted $C_1$-$C_6$ alkyl group (wherein said substituent is a substituent selected from the aforementioned substituent group B), $C_3$-$C_6$ cycloalkyl group, $C_2$-$C_6$ alkenyl group, cyano group, $C_2$-$C_7$ alkylcarbonyl group, benzoyl group, carboxyl group, $C_2$-$C_7$ alkoxycarbonyl group, carbamoyl group, di($C_1$-$C_6$ alkyl)carbamoyl group, optionally substituted phenyl group (wherein said substituent is a substituent selected from the aforementioned substituent group A), 5- or 6-membered heterocyclic group (wherein said heterocyclic ring contains one nitrogen atom, oxygen atom or sulfur atom therein, and may further contain 1 to 2 nitrogen atoms), optionally substituted amino group (wherein said substituent is a substituent selected from the following substituent group D), nitro group, hydroxyl group, $C_1$-$C_6$ alkoxy group, $C_1$-$C_6$ haloalkoxy group, phenoxy group, $C_1$-$C_6$ alkylthio group, phenylthio group, $C_1$-$C_6$ alkylsulfinyl group and $C_1$-$C_6$ alkylsulfonyl group;

substituent group D is a group consisting of a $C_1$-$C_6$ alkyl group, $C_2$-$C_7$ alkylcarbonyl group, $C_2$-$C_7$ alkoxycarbonyl group, di($C_1$-$C_6$ alkyl)carbamoyl group and $C_1$-$C_6$ alkylsulfonyl group; and substituent group E is a group consisting of a halogen atom, $C_1$-$C_6$ alkyl group, $C_1$-$C_6$ haloalkyl group, hydroxyl group, optionally substituted phenylsulfonyl group (wherein said substituent is a substituent selected from the aforementioned substituent group A) and di($C_1$-$C_6$ alkyl)sulfamoyl group];

the process comprising reacting a compound represented by general formula (7):

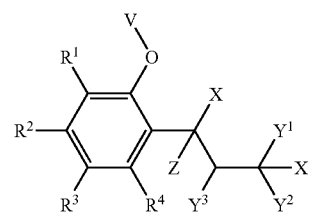

(7)

[wherein $R^1$, $R^2$, $R^3$, $R^4$, Z, $Y^1$, $Y^2$ and $Y^3$ are the same as previously defined; X represents a halogen atom; V represents a hydrogen atom or the group, —W—$R^5$, wherein $R^5$ represents a $C_1$-$C_6$ alkyl group, $C_1$-$C_6$ haloalkyl group, $C_3$-$C_6$ cycloalkyl group, $C_2$-$C_6$ alkenyl group, $C_2$-$C_6$ alkynyl group, optionally substituted phenyl group (wherein said substituent is a substituent selected from a halogen atom and $C_1$-$C_6$ alkyl group), $C_1$-$C_6$ alkoxy group or $C_1$-$C_6$ haloalkoxy group; and, W represents a CO, SO or $SO_2$ group], with a metal, metal salt or organometallic compound represented by general formula (8):

$$M^2 \qquad (8)$$

to obtain a compound represented by general formula (9):

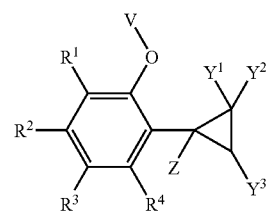

(9)

[wherein $R^1$, $R^2$, $R^3$, $R^4$, V, Z, $Y^1$, $Y^2$ and $Y^3$ are the same as previously defined] and obtaining a compound represented by general formula (10) by hydrolysis in the case V represents the group, —W—$R^5$.

2. The process according to claim 1, further comprising a step in which a compound of general formula (7) is obtained by reacting a compound represented by general formula (3):

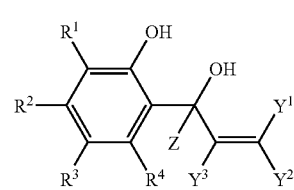

(3)

[wherein $R^1$, $R^2$, $R^3$, $R^4$, Z, $Y^1$, $Y^2$ and $Y^3$ are the same as defined in claim 1] with a mixture of a compound represented by general formula (4):

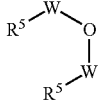

(4)

[wherein $R^5$ and W are the same as defined in claim 1] and a compound represented by general formula (5):

(5)

[wherein X is the same as defined in claim 1], or by reacting with an acid halide represented by general formula (6):

(6)

[wherein $R^5$, W and X are the same as previously defined].

3. The process according to claim 2, further comprising a step in which a compound represented by general formula (3) is obtained by reacting a compound represented by general formula (1):

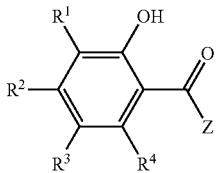

(1)

[wherein $R^1$, $R^2$, $R^3$, $R^4$ and Z are the same defined in claim 1], or salt thereof, with an organometallic compound represented by general formula (2):

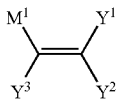

(2)

[wherein $Y^1$, $Y^2$ and $Y^3$ are the same as defined in claim 1; and $M^1$ represents a metal residue, metal salt residue or organometallic residue].

4. The process according to claim 1, further comprising a step in which a compound represented by general formula (7) is obtained by reacting a compound represented by general formula (11):

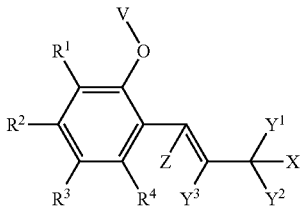

(11)

[wherein $R^1$, $R^2$, $R^3$, $R^4$, V, X, Z, $Y^1$, $Y^2$ and $Y^3$ are the same as defined in claim 1] with a hydrogen halide represented by general formula (5):

(5)

[wherein X is the same as previously defined].

5. The production process according to claim 1, wherein $R^1$, $R^2$, $R^3$ and $R^4$ are hydrogen atoms, halogen atoms or $C_1$-$C_6$ alkyl groups,
Z is a hydrogen atom,
$Y^1$, $Y^2$ and $Y^3$ are hydrogen atoms
$R^5$ is a $C_1$-$C_6$ alkyl group,
W is a CO group, and
X is a chlorine atom, bromine atom or iodine atom.

6. The production process according to claim 1, wherein $R^1$ is a halogen atom or $C_1$-$C_6$ alkyl group,
$R^2$, $R^3$ and $R^4$ are hydrogen atoms,
Z is a hydrogen atom,
$Y^1$, $Y^2$ and $Y^3$ are hydrogen atoms
$R^5$ is a $C_1$-$C_6$ alkyl group,
W is a CO group, and
X is a chlorine atom or bromine atom.

7. The production process according to claim 1, wherein $R^1$ is a fluorine atom, chlorine atom, bromine atom or methyl group,
$R^2$, $R^3$ and $R^4$ are hydrogen atoms,
Z is a hydrogen atom,
$Y^1$, $Y^2$ and $Y^3$ are hydrogen atoms
$R^5$ is a methyl group,
W is a CO group, and
X is a bromine atom.

8. The production process according to claim 3, wherein $M^1$ is lithium, boronic acid, sodium, magnesium, magnesium salt, aluminum, dialkyl aluminum, potassium, calcium, calcium salt, titanium, titanium salt, manganese, manganese salt, copper, copper salt, zinc, zinc salt, zinc alloy, tin, trialkyl tin, tellurium, alkyl tellurium, cerium, cerium salt, samarium, samarium salt, europium, europium salt, ytterbium or ytterbium salt, and
$M^2$ is lithium, lithium alloy, sodium, magnesium, magnesium salt, potassium, nickel, nickel salt, copper, copper salt, zinc, zinc salt, zinc alloy, chromium, chromium salt, methyl lithium, butyl lithium, t-butyl lithium, phenyl lithium, methyl magnesium chloride, methyl magnesium bromide, phenyl magnesium chloride, phenyl magnesium bromide or calcium.

9. The production process according to claim 3, wherein $M^1$ is lithium, boronic acid, magnesium, magnesium salt, aluminum, dialkyl aluminum, manganese, manganese salt, copper, copper salt, zinc, zinc salt, zinc alloy, tin, trialkyl tin, tellurium, alkyl tellurium, cerium or cerium salt, and
$M^2$ is lithium, lithium alloy, sodium, magnesium, magnesium salt, potassium, nickel, nickel salt, copper, copper salt, zinc, zinc salt, zinc alloy or t-butyl lithium.

10. The production process according to claim 3, wherein $M^1$ is magnesium, magnesium chloride, magnesium bromide or magnesium iodide, and
$M^2$ is magnesium, zinc, or zinc-copper alloy.

11. A compound or salt thereof represented by general formula (3):

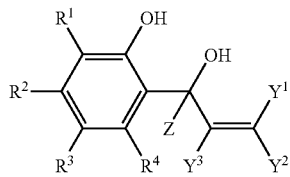

(3)

[wherein $R^1$, $R^2$, $R^3$ and $R^4$ are the same as defined in claim 1, and Z, $Y^1$, $Y^2$ and $Y^3$ represent hydrogen atoms, provided that $R^1$ is not a hydrogen atom].

12. The compound or salt thereof according to claim 11, wherein $R^1$ is a halogen atom or $C_1$-$C_6$ alkyl group, and $R^2$, $R^3$ and $R^4$ are hydrogen atoms.

13. A compound or salt thereof represented by the following general formula (7'):

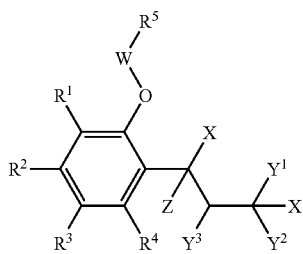

(7')

[wherein $R^1$, $R^2$, $R^3$, $R^4$, $R^5$, W, X, Z, $Y^1$, $Y^2$ and $Y^3$ are the same as defined in claim 1, provided that $R^5$ is neither a $C_1$-$C_6$ alkoxy group nor $C_1$-$C_6$ haloalkoxy group, and X is not a fluorine atom].

14. The compound or salt thereof according to claim 13, wherein $R^1$, $R^2$, $R^3$ and $R^4$ are hydrogen atoms, halogen atoms or $C_1$-$C_6$ alkyl groups, Z is a hydrogen atom, $Y^1$, $Y^2$ and $Y^3$ are hydrogen atoms, $R^5$ is a $C_1$-$C_6$ alkyl group, W is a CO group, and X is a chlorine atom, bromine atom or iodine atom.

15. The compound or salt thereof according to claim 13, wherein $R^1$ is a halogen atom or $C_1$-$C_6$ alkyl group, $R^2$, $R^3$ and $R^4$ are hydrogen atoms, Z is a hydrogen atom, $Y^1$, $Y^2$ and $Y^3$ are hydrogen atoms, $R^5$ is a $C_1$-$C_6$ alkyl group, W is a CO group, and X is a chlorine atom or bromine atom.

16. A compound or salt thereof represented by the following general formula (7'):

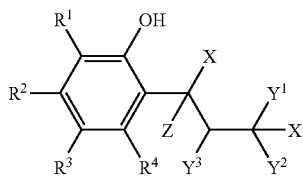

(7")

[wherein $R^1$, $R^2$, $R^3$, $R^4$, X, Z, $Y^1$, $Y^2$ and $Y^3$ are the same as defined in claim 1, provided that X is not a fluorine atom].

17. The compound or salt thereof according to claim 16, wherein $R^1$, $R^2$, $R^3$ and $R^4$ are hydrogen atoms, halogen atoms or $C_1$-$C_6$ alkyl groups, Z is a hydrogen atom, $Y^1$, $Y^2$ and $Y^3$ are hydrogen atoms, and X is a chlorine atom, bromine atom or iodine atom.

18. The compound or salt thereof according to claim 16, wherein $R^1$ is a halogen atom or $C_1$-$C_6$ alkyl group, $R^2$, $R^3$ and $R^4$ are hydrogen atoms, Z is a hydrogen atom, $Y^1$, $Y^2$ and $Y^3$ are hydrogen atoms, and X is a chlorine atom or bromine atom.

19. A compound or salt thereof represented by the following general formula (9'):

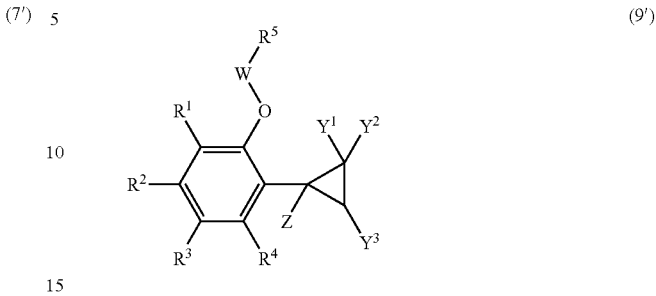

(9')

[wherein $R^1$, $R^2$, $R^3$, $R^4$, $R^5$, W, Z, $Y^1$, $Y^2$ and $Y^3$ are the same as defined in claim 1, provided that $R^1$ is neither a hydrogen atom nor acetoxy group].

20. The compound or salt thereof according to claim 19, wherein $R^1$ is a halogen atom or $C_1$-$C_6$ alkyl group, $R^2$, $R^3$ and $R^4$ are hydrogen atoms, Z is a hydrogen atom, $Y^1$, $Y^2$ and $Y^3$ are hydrogen atoms, $R^5$ is a $C_1$-$C_6$ alkyl group, and W is a CO group.

21. A compound or salt thereof represented by general formula (11'):

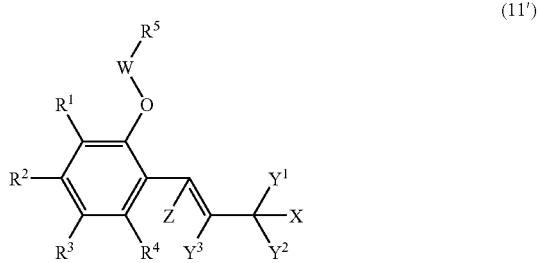

(11')

[wherein $R^1$, $R^2$, $R^3$, $R^4$, $R^5$, W, X, Z, $Y^1$, $Y^2$ and $Y^3$ are the same as defined in claim 1, provided that $R^1$ is neither a hydrogen atom nor acetoxy group, and X is not a fluorine atom].

22. The compound or salt thereof according to claim 21, wherein $R^1$, $R^2$, $R^3$ and $R^4$ are hydrogen atoms, halogen atoms or $C_1$-$C_6$ alkyl groups, Z is a hydrogen atom, $Y^1$, $Y^2$ and $Y^3$ are atoms, $R^5$ is a $C_1$-$C_6$ alkyl group, W is a CO group, and X is a chlorine atom, bromine atom or iodine atom, provided that $R^1$ is not hydrogen atom.

23. The compound or salt thereof according to claim 21, wherein $R^1$ is a halogen atom or $C_1$-$C_6$ alkyl group, $R^2$, $R^3$ and $R^4$ are hydrogen atoms, Z is a hydrogen atom, $Y^1$, $Y^2$ and $Y^3$ are hydrogen atoms, $R^5$ is a $C_1$-$C_6$ alkyl group, W is a CO group, and X is a chlorine atom or bromine atom.

24. A compound or salt thereof represented by general formula (11″):

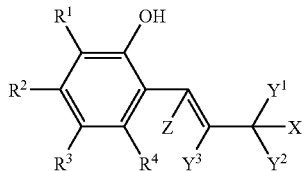
(11″)

[wherein $R^1$, $R^2$, $R^3$, $R^4$, X, Z and $Y^3$ are the same as defined in claim 1, and $Y^1$ and $Y^2$ represent hydrogen atoms, provided that X is not a fluorine atom].

25. The compound or salt thereof according to claim 24, wherein $R^1$, $R^2$, $R^3$ and $R^4$ are hydrogen atoms, halogen atoms or $C_1$-$C_6$ alkyl groups,
Z is a hydrogen atom,
$Y^1$, $Y^2$ and $Y^3$ are hydrogen atoms, and
X is a chlorine atom, bromine atom or iodine atom.

26. The compound or salt thereof according to claim 24, wherein $R^1$ is a halogen atom or $C_1$-$C_6$ alkyl group,
$R^2$, $R^3$ and $R^4$ are hydrogen atoms,
Z is a hydrogen atom,
$Y^1$, $Y^2$ and $Y^3$ are hydrogen atoms, and
X is a chlorine atom or bromine atom.

27. The production process according to claim 3, wherein $R^1$ is a fluorine atom, chlorine atom, bromine atom or methyl group,
$R^2$, $R^3$ and $R^4$ are hydrogen atoms,
Z is a hydrogen atom,
$Y^1$, $Y^2$ and $Y^3$ are atoms,
$R^5$ is a methyl group,
W is a CO group,
X is a bromine atom,
$M^1$ is magnesium chloride, and
$M^2$ is magnesium.

28. The compound according to claim 11, wherein $R^1$ is a fluorine atom, chlorine atom, bromine atom or methyl group,
$R^2$, $R^3$ and $R^4$ are hydrogen atoms,
Z is a hydrogen atom, and
$Y^1$, $Y^2$ and $Y^3$ are hydrogen atoms.

29. The compound according to claim 13, wherein $R^1$ is a fluorine atom, chlorine atom, bromine atom or methyl group,
$R^2$, $R^3$ and $R^4$ are hydrogen atoms,
Z is a hydrogen atom,
$Y^1$, $Y^2$ and $Y^3$ are hydrogen atoms,
$R^5$ is a methyl group,
W is a CO group, and
X is a bromine atom.

30. The compound according to claim 16, wherein $R^1$ is a fluorine atom, chlorine atom, bromine atom or methyl group,
$R^2$, $R^3$ and $R^4$ are hydrogen atoms,
Z is a hydrogen atom,
$Y^1$, $Y^2$ and $Y^3$ are hydrogen atoms, and
X is a bromine atom.

31. The compound according to claim 19, wherein $R^1$ is a fluorine atom, chlorine atom, bromine atom or methyl group,
$R^2$, $R^3$ and $R^4$ are hydrogen atoms,
Z is a hydrogen atom,
$Y^1$, $Y^2$ and $Y^3$ are hydrogen atoms,
$R^5$ is a methyl group, and
W is a CO group.

32. The compound according to claim 21, wherein $R^1$ is a fluorine atom, chlorine atom, bromine atom or methyl group,
$R^2$, $R^3$ and $R^4$ are hydrogen atoms,
Z is a hydrogen atom,
$Y^1$, $Y^2$ and $Y^3$ are hydrogen atoms,
$R^5$ is a methyl group,
W is a CO group, and
X is a bromine atom.

33. The compound according to claim 24, wherein $R^1$ is a fluorine atom, chlorine atom, bromine atom or methyl group,
$R^2$, $R^3$ and $R^4$ are hydrogen atoms,
Z is a hydrogen atom,
$Y^1$, $Y^2$ and $Y^3$ are hydrogen atoms, and
X is a bromine atom.

34. The compound according to claim 11, wherein the compound is 2-(1-hydroxyl-2-propenyl)-6-methylphenol.

35. The compound according to claim 13, wherein the compound is 2-(1,3-dibromopropyl)-6-methylphenyl acetate.

36. The compound according to claim 16, wherein the compound is 2-(1,3-dibromopropyl)-6-methylphenol.

37. The compound according to claim 19, wherein the compound is 2-cyclopropyl-6-methylphenyl acetate.

38. The compound according to claim 21, wherein the compound is 2-(3-bromo-1-propenyl)-6-methylphenyl acetate.

39. The compound according to claim 24, wherein the compound is 2-(3-bromo-1-propenyl)-6-methylphenol.

* * * * *